(12) United States Patent
Visintin et al.

(10) Patent No.: US 8,080,245 B2
(45) Date of Patent: Dec. 20, 2011

(54) ANTI-PATHOGEN IMMUNOADHESINS

(75) Inventors: Alberto Visintin, Worcester, MA (US); Douglas T. Golenbock, Wellesley, MA (US)

(73) Assignee: University of Massachusetts, Shrewsbury, MA (US)

( * ) Notice: Subject to any disclaimer, the term of this patent is extended or adjusted under 35 U.S.C. 154(b) by 193 days.

(21) Appl. No.: 11/659,154

(22) PCT Filed: Aug. 4, 2005

(86) PCT No.: PCT/US2005/027944
§ 371 (c)(1),
(2), (4) Date: Feb. 27, 2009

(87) PCT Pub. No.: WO2007/001332
PCT Pub. Date: Jan. 4, 2007

(65) Prior Publication Data
US 2009/0208501 A1 Aug. 20, 2009

Related U.S. Application Data

(60) Provisional application No. 60/598,774, filed on Aug. 4, 2004, provisional application No. 60/668,703, filed on Apr. 6, 2005.

(51) Int. Cl.
*A61K 39/395* (2006.01)
*A61K 39/00* (2006.01)
*C07K 1/00* (2006.01)
*C07K 16/00* (2006.01)
*C12P 21/08* (2006.01)

(52) U.S. Cl. ............... 424/134.1; 424/130.1; 424/131.1; 530/350; 530/387.1; 530/387.2; 530/388.2; 530/388.4

(58) Field of Classification Search .................. None
See application file for complete search history.

(56) References Cited

U.S. PATENT DOCUMENTS

| | | | | |
|---|---|---|---|---|
| 4,438,114 A | * | 3/1984 | Boberg et al. | 514/210.08 |
| 5,578,572 A | * | 11/1996 | Horwitz et al. | 514/12 |
| 5,643,570 A | * | 7/1997 | Theofan et al. | 424/134.1 |
| 6,107,076 A | * | 8/2000 | Tang et al. | 435/232 |
| 6,462,254 B1 | | 10/2002 | Vernachio et al. | |
| 6,569,112 B2 | | 5/2003 | Strahilevitz | |
| 6,660,843 B1 | * | 12/2003 | Feige et al. | 530/391.7 |
| 7,157,418 B1 | | 1/2007 | McDonald et al. | |
| 2003/0032090 A1 | * | 2/2003 | Hardiman et al. | 435/69.1 |
| 2003/0049648 A1 | | 3/2003 | Choi | |

FOREIGN PATENT DOCUMENTS

WO WO 2004/103294 * 12/2004
WO WO 2006/025995 A2 * 3/2006

OTHER PUBLICATIONS

Bassler et al. Current Opinion in Microbiology 1999, 2:582-587.*
Paul. Fundamental Immunology, 5th edition. 2003 Chapter 3 (p. 56-58): The Immunoglobulin Hinge.*
Chmura et al. Chest 2003; 124,379-382.*
Abrahamson et al., "Biochemical characterization of recombinant fusions of lipopolysaccharide binding protein and bactericidal/permeability-increasing protein. Implications in biological activity," Journal of Biological Chemistry, 272:2149-2155 (1997).
Ashkenazi et al., "Immunoadhesins as research tolls and therapeutic agents," Curr. Opin. Immunol., 9(2):195-200 (1997).
Bazil and Strominger, "Shedding as a mechanism of down-modulation of CD14 on stimulated human monocytes," J. Immunol., 147:1567-1574 (1991).
Bazil et al., "Biochemical characterization of a soluble form of the 53-kDa monocyte surface antigen," Eur. J. Immunol., 16:1583-1589 (1986).
Beamer et al., "The BPI/LBP family of proteins: a structural analysis of conserved regions," Protein Science, 7:906-914 (1998).
Bell et al., "The molecular structure of the Toll-like receptor 3 ligand-binding domain," Proc. Natl. Acad. Sci. USA, 102(31):10976-10980 (2005).
Bell et al., "Leucine-rich repeats and pathogen recognition in Toll-like receptors," TRENDS Immunology, 24(10):528-533 (2003).
Bufler et al., "Soluble lipopolysaccharide receptor (CD14) is released via two different mechanisms from human monocytes and CD14 transfectants," Eur. J. Immunol., 25:604-610 (1995).
Chamow et al., "Immunoadhesins: principles and applications," Trends Biotechnol., 14(2):52-60 (1996).
Froidevaux et al., "Anti-Toll-Like Receptor 4 (TLR4) Antibodies Protect from Lethal Endotoxemia but Not from Gram-Negative Septice Shock," Gateway to the National Library of Medicine, [printed from http://gateway.nlm.nih.gov/MeetingAbstracts/102265282.html on Jan. 25, 2008].
Gioannini et al., "Isolation of an endotoxin-MD-2 complex that produces Toll-like receptor 4-dependent cell activation at picomolar concentrations," Proc. Natl. Acad. Sci. USA, 101:4186-4191 (2004).
Goldbach-Mansky and Lipsky, "New Concepts in the Treatment of Rheumatoid Arthritis," Annu. Rev. Med., 55:197-216 (2003).
Haziot et al., "The monocyte differentiation antigen, CD14, is anchored to the cell membrane by a phosphatidylinositol linkage," J. Immunol., 141:547-552 (1988).
Haziot et al., "Neutrophil CD14: biochemical properties and role in the secretion of tumor necrosis factor-alpha in response to lipopolysaccharide," J. Immunol., 150:5556-5565 (1998).
Hyakushima et al., "Interaction of soluble form of recombinant extracellular TLR4 domain with MD-2 enables lipopolysaccharide binding and attenuates TLR4-mediated signaling," J. Immunol., 173(11):6949-6954 (2004).
Jit et al., "TNF-alpha neutralization in cytokine-driven diseases: a mathematical model to account for therapeutic success in rheumatoid arthritis but therapeutic failure in systemic inflammatory response syndrome," Rheumatology, 44:323-331 (2005).

(Continued)

*Primary Examiner* — Oluwatosin Ogunbiyi
(74) *Attorney, Agent, or Firm* — Fish & Richardson P.C.

(57) ABSTRACT

Chimeric molecules that include a pathogen recognition module derived from a pathogen binding domain of a pathogen recognition protein, e.g., a toll-like receptor (TLR), CD14, BPI, MD-2, scavenger receptors (SRs), surfactant proteins (SP), C-reactive protein (CRP), Mannan-binding lectin (MBL), or complement Clq globular binding domain, an optional linker, and an Fc portion of an antibody are described and are useful for, e.g., drug discovery and treatment of conditions related to TLR signaling.

16 Claims, 7 Drawing Sheets

OTHER PUBLICATIONS

Juan et al., "Soluble CD14 truncated at amino acid 152 binds lipopolysaccharide (LPS) and enables cellular response to LPS," J. Biol. Chem., 270:1382-1387 (1995).

Kennedy et al., "A complex of soluble MD-2 and lipopolysaccharide serves as an activating ligand for Toll-like receptor 4," J. Biol. Chem., 279:34698-34704 (2004).

LaBeta et al., "Release from a human monocyte-like cell line of two different soluble forms of the lipopolysaccharide receptor, CD14," Eur. J. Immunol, 23:2144-2151 (1993).

Landmann et al., "Increased circulating soluble CD14 is associated with high mortality in gram-negative septic shock," J. Infect. Dis., 171:639-644 (1995).

Latz et al., "TLR9 signals after translocating from the ER to CpG DNA in the lysosome," Nat. Immunol , 5(2):190-198 (2004).

Lawson et al., "Treatment of murine lupus with cDNA encoding IFN-γR/Fc," J. Clin. Invest., 106:207-215 (2000).

LeBouder et al., "Soluble forms of Toll-like receptor (TLR)2 capable of modulating TLR2 signaling are present in human plasma and breast milk," J. Immunol., 171(12):6680-6689 (2003).

Meng et al., "Antagonistic antibody prevents toll-like receptor 2-driven lethal shock-like syndromes," J. Clin. Invest., 113(10):1473-1481 (2004).

Navia et al., "Crystal structure of galactan-binding mouse immunoglobulin J539 Fab at 4.5-A resolution," Proc. Natl. Acad. Sci. USA, 76:4071-4074 (1979).

Pugin et al., "Soluble MD-2 activity in plasma from patients with severe sepsis and septic shock," Blood, 104(13):4071-4079 (2004).

R&D Systems, "Recombinant Mouse CD14/Fc Chimera," Catalog No. 982-CD (2001).

Ram et al., "C4bp binding to porin mediates stable serum resistance of *Neisseria gonorrhoeae*," Int. Immunopharmacol., 1:423-432 (2001).

Ram et al., "Binding of C4b-binding protein to porin: a molecular mechanism of serum resistance of *Neisseria gonorrhoeae*," J. Exp. Med., 193:281 (2001).

Robinson et al., "Optimizing the stability of single-chain proteins by linker length and composition mutagenesis," Proc. Natl. Acad. Sci. USA, 95:5929-5934 (1998).

Rothenfusser et al., "Recent advances in immunostimulatory CpG oligonucleotides," Curr. Opin. Mol. Ther., 5(2):98-106 (2003).

Shimazu et al., "MD-2, a molecule that confers lipopolysaccharide responsiveness on Toll-like receptor 4," J. Exp. Med., 189(11):1777-1782 (1999).

Takeuchi et al., "Discrimination of bacterial lipoproteins by Toll-like receptor 6," Int. Immunol., 13:933-940 (2001).

Takeuchi et al., "Cutting edge: role of Toll-like receptor 1 in mediating immune response to microbial lipoproteins," J. Immunol , 169:10-14 (2002).

Viriyakosol and Kirkland, "The N-terminal half of membrane CD14 is a functional cellular lipopolysaccharide receptor," Infect. Immun , 64(2):653-656 (1996).

Visintin et al., "Lysines 128 and 132 enable lipopolysaccharide binding to MD-2, leading to Toll-like receptor-4 aggregation and signal transduction," J. Biol. Chem., 278(48):48313-48320 (2003).

Froidevaux, R.T. et al., "Anti-Toll-Like Receptor 4 (TLR4) Antibodies Protect from Lethal Endotoxemia but Not from Gram-Negative Septic Shock," Abst Intersci Conf Antimicrob Agents Chemother Intersci Conf antimicro angents Chemother, Sep. 14-17, 2003 (Lusanee, Switzerland), abstract No. B-1506.

Akashi et al., "Lipopolysaccharide interaction with cell surface Toll-like receptor 4-MD 2: higher affinity than that with MD 2 or CD14," J. Exp. Med., 198:1035 (2003).

Beutler, "Inferences, questions and possibilities in Toll-like receptor signalling," Nature, 430:257 (2004).

Fitzgerald et al., "LPS-TLR4 signaling to IRF-3/7 and NR-kappaB involves the toll adapters TRAM and TRIF," J. Exp. Med., 198:1043 (2003).

Gangloff et al., "MD 2: the Toll 'gatekeeper' in endotoxin signalling," Trends Biochem. Sci., 29:294 (2004).

Gruber et al., "Structural model of MD 2 and functional role of its basic amino acid clusters involved in cellular lipopolysaccharide recognition," J. Biol. Chem., 279:28475 (2004).

Inohara et al., "ML—a conserved domain involved in innate immunity and lipid metabolism," Trends Biochem. Sci., 27:219 (2002).

Jack et al., "Lipopolysaccharide-binding protein is required to combat a murine gram-negative bacterial infection," Nature, 389:742 (1997).

Kennedy et al., "A complex of soluble MD 2 and lipopolysaccharide serves as an activating ligand for Toll-like receptor 4," J. Biol. Chem. 279:34698 (2004).

Latz et al., "Lipopolysaccharide rapidly traffics to and from the Golgi apparatus with the toll-like receptor 4-MD 2-CD14 complex in a process that is distinct from the initiation of signal transduction," J. Biol. Chem. 277:47834 (2002).

Latz et al., "The LPS receptor generates inflammatory signals from the cell surface," J. Endotoxin. Res., 9:375 (2003).

Lawton et al., "Novel therapeutic strategies based on toll-like receptor signaling," Current Opinion in Chem Biol. 7: 446-451, 2003.

Lien et al., "Toll-like receptor 4 imparts ligand-specific recognition of bacterial lipopolysaccharide," J. Clin. Invest., 105:497 (2000).

Mullarkey et al., "Inhibition of endotoxin response by e5564, a novel Toll-like receptor 4-directed endotoxin antagonist," J. Pharmacol. Exp. Ther., 304:1093 (2003).

Mullen et al,, "The role of disulfide bonds in the assembly and function of MD 2," Proc. Natl. Acad. Sci. USA, 100:3919 (2003).

Nagai et al,. "Essential role of MD 2 in LPS responsiveness and TLR4 distribution," Nat. Immunol., (2002).

Poltorak et al., "Physical contact between lipopolysaccharide and Toll-like receptor 4 revealed by genetic complementation," Proc. Natl. Acad, Sci. USA, 97:2163 (2000).

Re et al., "Monomeric recombinant MD 2 binds TLR4 tightly and confers LPS responsiveness," J. Biol. Chem., (2002).

Saitoh et al., "Lipid A antagonist, lipid IVa, is distinct from lipid A in interaction with Toll-like receptor 4 (TLR4)-MD 2 and ligand-induced TLR4 oligomerization," Int. Immunol., 16:961 (2004).

Schromm et al., "Molecular genetic analysis of an endotoxin nonresponder mutant cell line: a point mutation in a conserved region of MD 2 abolishes endotoxin-induced signaling," J. Exp. Med. 194:79 (2001).

Triantafilou et al., "Combinational clustering of receptors following stimulation by bacterial products determines lipopolysaccharide responses," Biochem. J., 381:527 (2004).

Ulevitch et al., "Recognition of Gram-negative bacteria and endotoxin by the innate immune system," Curr. Opin. in Immn. 11: 19-22, 1999.

Visintin et al., "Secreted MD 2 is a large polymeric protein that efficiently confers lipopolysaccharide sensitivity to Toll-like receptor 4," Proc. Natl. Acad. Sci, USA, 98:12156 (2001).

Weber et al., "Binding of the *Drosophila* cytokine Spatzle to Toll is direct and establishes signaling," Nat. Immunol., 4:794 (2003).

\* cited by examiner pathogen recognition module spacer

Fc

Supernatants | Whole cell lysates

Y. pestis 26°C  Y. pestis 37°C  P. aeruginosa  E. coli
(heat killed)  (heat killed)  (4°C)  (4°C)

S. pneumoniae  E. coli  L. monocytogenes

N. Meningitidis  N. Meningitidis  N. Meningitidis  Y. Pestis
(MC58 Capsule −)  (MC58 Capsule +)

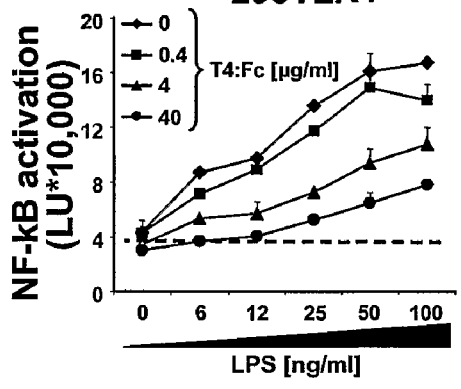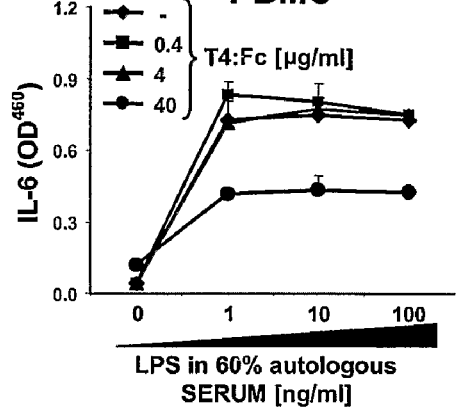
Figure 12A 293TLR4
Figure 12B PBMC
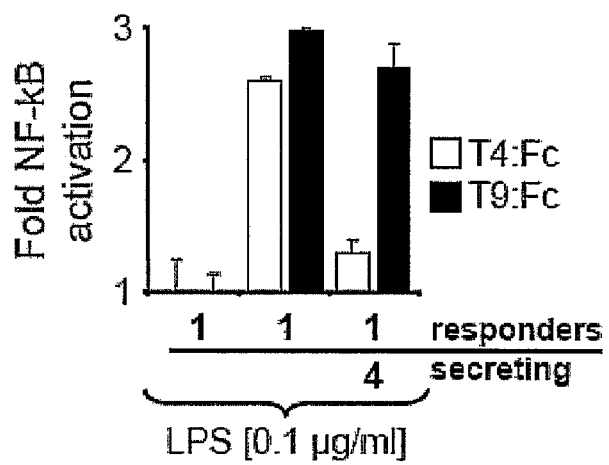
Figure 13
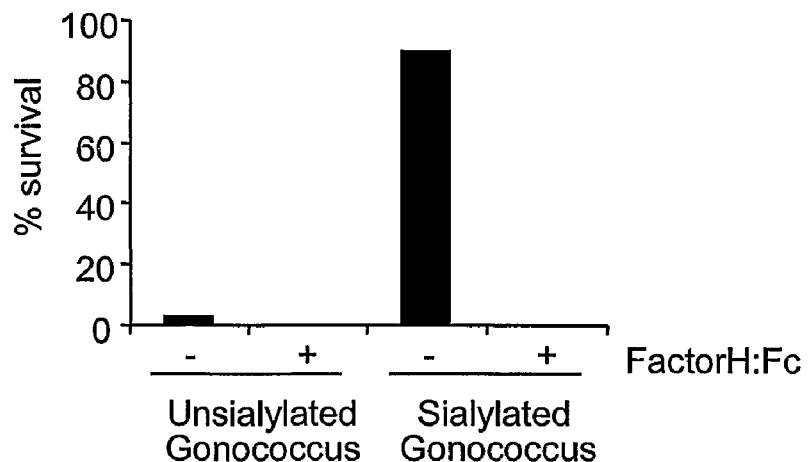
Figure 14

ID NO:22), V5 (GKPIPNPLLGLDST; SEQ ID NO:23), Myc

```
                          SEQUENCE LISTING

<160> NUMBER OF SEQ ID NOS: 35

<210> SEQ ID NO 1
<211> LENGTH: 5
<212> TYPE: DNA
<213> ORGANISM: Artificial Sequence
<220> FEATURE:
<223> OTHER INFORMATION: synthesized in laboratory

<400> SEQUENCE: 1 gaagg                                                                   5

<210> SEQ ID NO 2
<211> LENGTH: 5
<212> TYPE: DNA
<213> ORGANISM: Artificial Sequence
<220> FEATURE:
<223> OTHER INFORMATION: synthesized in laboratory

<400> SEQUENCE: 2 aaagg                                                                   5

<210> SEQ ID NO 3
<211> LENGTH: 62
<212> TYPE: DNA
<213> ORGANISM: Artificial Sequence
```

```
<220> FEATURE:
<223> OTHER INFORMATION: synthesized in laboratory

<400> SEQUENCE: 3
ggaattctgc agatatccat cacactggcg gccgcggggg gcgagcccag agggcccaca        60
at                                                                      62

<210> SEQ ID NO 4
<211> LENGTH: 16
<212> TYPE: DNA
<213> ORGANISM: Artificial Sequence
<220> FEATURE:
<223> OTHER INFORMATION: synthesized in laboratory

<400> SEQUENCE: 4
tcagatgaat aagacc                                                       16

<210> SEQ ID NO 5
<211> LENGTH: 20
<212> TYPE: DNA
<213> ORGANISM: Artificial Sequence
<220> FEATURE:
<223> OTHER INFORMATION: synthesized in laboratory

<400> SEQUENCE: 5
gagcccagag ggcccacaat                                                   20

<210> SEQ ID NO 6
<211> LENGTH: 31
<212> TYPE: DNA
<213> ORGANISM: Artificial Sequence
<220> FEATURE:
<223> OTHER INFORMATION: synthesized in laboratory

<400> SEQUENCE: 6
tcagatgaat aagaccgggg ccgcgggggg c                                      31

<210> SEQ ID NO 7
<211> LENGTH: 20
<212> TYPE: DNA
<213> ORGANISM: Artificial Sequence
<220> FEATURE:
<223> OTHER INFORMATION: synthesized in laboratory

<400> SEQUENCE: 7
gagcccagag ggcccacaat                                                   20

<210> SEQ ID NO 8
<211> LENGTH: 13
<212> TYPE: PRT
<213> ORGANISM: Artificial Sequence
<220> FEATURE:
<223> OTHER INFORMATION: synthesized in laboratory

<400> SEQUENCE: 8

Glu Cys His Arg Ala Ala Ala Gly Gly Glu Pro Arg Gly
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: synthesized in laboratory
```

```
<400> SEQUENCE: 9

Met Asn Lys Thr Gly Ala Ala Gly Gly Glu Pro Arg Gly
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: synthesized in laboratory

<400> SEQUENCE: 10

Trp Asp Cys Phe Ala Ala Ala Gly Gly Glu Pro Arg Gly
 1               5                  10

<210> SEQ ID NO 11
<211> LENGTH: 13
<212> TYPE: PRT
<213> ORGANISM: Artificial Sequence
<220> FEATURE:
<223> OTHER INFORMATION: synthesized in laboratory

<400> SEQUENCE: 11

Ala Cys Ala Arg Ala Ala Ala Gly Gly Glu Pro Arg Gly
 1               5                  10

<210> SEQ ID NO 12
<211> LENGTH: 25
<212> TYPE: DNA
<213> ORGANISM: Artificial Sequence
<220> FEATURE:
<223> OTHER INFORMATION: synthesized in laboratory

<400> SEQUENCE: 12
cgagctcgga tccatgggtt tctgc                                    25

<210> SEQ ID NO 13
<211> LENGTH: 34
<212> TYPE: DNA
<213> ORGANISM: Artificial Sequence
<220> FEATURE:
<223> OTHER INFORMATION: synthesized in laboratory

<400> SEQUENCE: 13
ccagcagcgc ggccgcgaaa cagtcccagg agag                          34

<210> SEQ ID NO 14
<211> LENGTH: 44
<212> TYPE: DNA
<213> ORGANISM: Artificial Sequence
<220> FEATURE:
<223> OTHER INFORMATION: synthesized in laboratory

<400> SEQUENCE: 14
tcacctgtgc ggccgcgggg ggcgagccca gagggcccac aatc               44

<210> SEQ ID NO 15
<211> LENGTH: 37
<212> TYPE: DNA
<213> ORGANISM: Artificial Sequence
<220> FEATURE:
<223> OTHER INFORMATION: synthesized in laboratory

<400> SEQUENCE: 15
ggatatctgc agaactcgag gtcgactcat ttacccg                       37
```

```
<210> SEQ ID NO 16
<211> LENGTH: 8
<212> TYPE: DNA
<213> ORGANISM: Artificial Sequence
<220> FEATURE:
<223> OTHER INFORMATION: synthesized in laboratory

<400> SEQUENCE: 16 gcggccgc                                                                   8

<210> SEQ ID NO 17
<211> LENGTH: 5
<212> TYPE: PRT
<213> ORGANISM: Artificial Sequence
<220> FEATURE:
<223> OTHER INFORMATION: synthesized in laboratory

<400> SEQUENCE: 17

Ala Ala Ala Gly Gly
 1               5

<210> SEQ ID NO 18
<211> LENGTH: 566
<212> TYPE: PRT
<213> ORGANISM: Artificial Sequence
<220> FEATURE:
<223> OTHER INFORMATION: synthesized in laboratory

<400> SEQUENCE: 18

Met Ser Ala Leu Leu Ile Leu Ala Leu Val Gly Ala Ala Val Ala Asp
 1               5                  10                  15

Tyr Lys Asp Asp Asp Asp Lys Leu Gly Ala Pro Cys Lys Ser Pro Pro
             20                  25                  30

Glu Ile Ser His Gly Val Val Ala His Met Ser Asp Ser Tyr Gln Tyr
         35                  40                  45

Gly Glu Glu Val Thr Tyr Lys Cys Phe Glu Gly Phe Gly Ile Asp Gly
     50                  55                  60

Pro Ala Ile Ala Lys Cys Leu Gly Glu Lys Trp Ser His Pro Pro Ser
 65                  70                  75                  80

Cys Ile Lys Thr Asp Cys Leu Ser Leu Pro Ser Phe Glu Asn Ala Ile
                 85                  90                  95

Pro Met Gly Glu Lys Lys Asp Val Tyr Lys Ala Gly Glu Gln Val Thr
            100                 105                 110

Tyr Thr Cys Ala Thr Tyr Tyr Lys Met Asp Gly Ala Ser Asn Val Thr
        115                 120                 125

Cys Ile Asn Ser Arg Trp Thr Gly Arg Pro Thr Cys Arg Asp Thr Ser
    130                 135                 140

Cys Val Asn Pro Pro Thr Val Gln Asn Ala Tyr Ile Val Ser Arg Gln
145                 150                 155                 160

Met Ser Lys Tyr Pro Ser Gly Glu Arg Val Arg Tyr Gln Cys Arg Ser
                165                 170                 175

Pro Tyr Glu Met Phe Gly Asp Glu Glu Val Met Cys Leu Asn Gly Asn
            180                 185                 190

Trp Thr Glu Pro Pro Gln Cys Lys Asp Ser Thr Gly Lys Cys Gly Pro
        195                 200                 205

Pro Pro Pro Ile Asp Asn Gly Asp Ile Thr Ser Phe Pro Leu Ser Val
    210                 215                 220

Tyr Ala Pro Ala Ser Ser Val Glu Tyr Gln Cys Gln Asn Leu Tyr Gln
225                 230                 235                 240
```

-continued

```
Leu Glu Gly Asn Lys Arg Ile Thr Cys Arg Asn Gly Gln Trp Ser Glu
                245                 250                 255
Pro Pro Lys Cys Leu His Pro Cys Val Ile Ser Arg Glu Ile Met Glu
            260                 265                 270
Asn Tyr Asn Ile Ala Leu Arg Trp Thr Ala Lys Gln Lys Leu Tyr Ser
        275                 280                 285
Arg Thr Gly Glu Ser Val Glu Phe Val Cys Lys Arg Gly Tyr Arg Leu
    290                 295                 300
Ser Ser Arg Ser His Thr Leu Arg Thr Cys Trp Asp Gly Lys Leu
305                 310                 315                 320
Glu Tyr Pro Thr Cys Ala Lys Arg Ala Ala Gly Gly Glu Pro Arg
                325                 330                 335
Gly Pro Thr Ile Lys Pro Cys Pro Pro Cys Lys Cys Pro Ala Pro Asn
            340                 345                 350
Leu Leu Gly Gly Pro Ser Val Phe Ile Phe Pro Pro Lys Ile Lys Asp
        355                 360                 365
Val Leu Met Ile Ser Leu Ser Pro Ile Val Thr Cys Val Val Val Asp
    370                 375                 380
Val Ser Glu Asp Asp Pro Asp Val Gln Ile Ser Trp Phe Val Asn Asn
385                 390                 395                 400
Val Glu Val His Thr Ala Gln Thr Gln Thr His Arg Glu Asp Tyr Asn
                405                 410                 415
Ser Thr Leu Arg Val Val Ser Ala Leu Pro Ile Gln His Gln Asp Trp
            420                 425                 430
Met Ser Gly Lys Glu Phe Lys Cys Lys Val Asn Asn Lys Asp Leu Pro
        435                 440                 445
Ala Pro Ile Glu Arg Thr Ile Ser Lys Pro Lys Gly Ser Val Arg Ala
    450                 455                 460
Pro Gln Val Tyr Val Leu Pro Pro Pro Glu Glu Glu Met Thr Lys Lys
465                 470                 475                 480
Gln Val Thr Leu Thr Cys Met Val Thr Asp Phe Met Pro Glu Asp Ile
                485                 490                 495
Tyr Val Glu Trp Thr Asn Asn Gly Lys Thr Glu Leu Asn Tyr Lys Asn
            500                 505                 510
Thr Glu Pro Val Leu Asp Ser Asp Gly Ser Tyr Phe Met Tyr Ser Lys
        515                 520                 525
Leu Arg Val Glu Lys Lys Asn Trp Val Glu Arg Asn Ser Tyr Ser Cys
    530                 535                 540
Ser Val Val His Glu Gly Leu His Asn His His Thr Thr Lys Ser Phe
545                 550                 555                 560
Ser Arg Thr Pro Gly Lys
                565

<210> SEQ ID NO 19
<211> LENGTH: 449
<212> TYPE: PRT
<213> ORGANISM: Artificial Sequence
<220> FEATURE:
<223> OTHER INFORMATION: synthesized in laboratory

<400> SEQUENCE: 19

Met Ser Ala Leu Leu Ile Leu Ala Leu Val Gly Ala Ala Val Ala Asp
 1               5                  10                  15
Tyr Lys Asp Asp Asp Asp Lys Leu Gly Ala Pro Cys Val Asn Pro Pro
                20                  25                  30
```

```
Thr Val Gln Asn Ala Tyr Ile Val Ser Arg Gln Met Ser Lys Tyr Pro
         35                  40                  45

Ser Gly Glu Arg Val Arg Tyr Gln Cys Arg Ser Pro Tyr Glu Met Phe
 50                  55                  60

Gly Asp Glu Glu Val Met Cys Leu Asn Gly Asn Trp Thr Glu Pro Pro
 65                  70                  75                  80

Gln Cys Lys Asp Ser Thr Gly Lys Cys Gly Pro Pro Pro Pro Ile Asp
                 85                  90                  95

Asn Gly Asp Ile Thr Ser Phe Pro Leu Ser Val Tyr Ala Pro Ala Ser
                100                 105                 110

Ser Val Glu Tyr Gln Cys Gln Asn Leu Tyr Gln Leu Glu Gly Asn Lys
            115                 120                 125

Arg Ile Thr Cys Arg Asn Gly Gln Trp Ser Glu Pro Pro Lys Cys Leu
        130                 135                 140

His Pro Cys Val Ile Ser Arg Glu Ile Met Glu Asn Tyr Asn Ile Ala
145                 150                 155                 160

Leu Arg Trp Thr Ala Lys Gln Lys Leu Tyr Ser Arg Thr Gly Glu Ser
                165                 170                 175

Val Glu Phe Val Cys Lys Arg Gly Tyr Arg Leu Ser Ser Arg Ser His
            180                 185                 190

Thr Leu Arg Thr Thr Cys Trp Asp Gly Lys Leu Glu Tyr Pro Thr Cys
        195                 200                 205

Ala Lys Arg Ala Ala Gly Gly Glu Pro Arg Gly Pro Thr Ile Lys
        210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys
```

```
<210> SEQ ID NO 20
<211> LENGTH: 638
<212> TYPE: PRT
<213> ORGANISM: Artificial Sequence
<220> FEATURE:
<223> OTHER INFORMATION: synthesized in laboratory

<400> SEQUENCE: 20

Met Ser Ala Leu Leu Ile Leu Ala Leu Val Gly Ala Ala Val Ala Asp
  1               5                  10                  15

Tyr Lys Asp Asp Asp Asp Lys Leu Gly Ala Pro Asn Cys Gly Pro Pro
                 20                  25                  30

Pro Thr Leu Ser Phe Ala Ala Pro Met Asp Ile Thr Leu Thr Glu Thr
             35                  40                  45

Arg Phe Lys Thr Gly Thr Thr Leu Lys Tyr Thr Cys Leu Pro Gly Tyr
 50                  55                  60

Val Arg Ser His Ser Thr Gln Thr Leu Thr Cys Asn Ser Asp Gly Glu
 65                  70                  75                  80

Trp Val Tyr Asn Thr Phe Cys Gly Ser Val Lys Cys Lys Pro Pro Pro
                 85                  90                  95

Asp Ile Arg Asn Gly Arg His Ser Gly Glu Glu Asn Phe Tyr Ala Tyr
                100                 105                 110

Gly Phe Ser Val Thr Tyr Ser Cys Asp Pro Arg Phe Ser Leu Leu Gly
            115                 120                 125

His Ala Ser Ile Ser Cys Thr Val Glu Asn Glu Thr Ile Gly Val Trp
130                 135                 140

Arg Pro Ser Pro Pro Thr Cys Glu Lys Ile Thr Cys Arg Lys Pro Asp
145                 150                 155                 160

Val Ser His Gly Glu Met Val Ser Gly Phe Gly Pro Ile Tyr Asn Tyr
                165                 170                 175

Lys Asp Thr Ile Val Phe Lys Cys Gln Lys Gly Phe Val Leu Arg Gly
                180                 185                 190

Ser Ser Val Ile His Cys Asp Ala Asp Ser Lys Trp Asn Pro Ser Pro
            195                 200                 205

Pro Ala Cys Glu Pro Asn Ser Cys Ile Asn Leu Pro Asp Ile Pro His
210                 215                 220

Ala Ser Trp Glu Thr Tyr Pro Arg Pro Thr Lys Glu Asp Val Tyr Val
225                 230                 235                 240

Val Gly Thr Val Leu Arg Tyr Arg Cys His Pro Gly Tyr Lys Pro Thr
                245                 250                 255

Thr Asp Glu Pro Thr Thr Val Ile Cys Gln Lys Asn Leu Arg Trp Thr
                260                 265                 270

Pro Tyr Gln Gly Cys Glu Ala Leu Cys Cys Pro Glu Pro Lys Leu Asn
            275                 280                 285

Asn Gly Glu Ile Thr Gln His Arg Lys Ser Arg Pro Ala Asn His Cys
290                 295                 300

Val Tyr Phe Tyr Gly Asp Glu Ile Ser Phe Ser Cys His Glu Thr Ser
305                 310                 315                 320

Arg Phe Ser Ala Ile Cys Gln Gly Asp Gly Thr Trp Ser Pro Arg Thr
                325                 330                 335

Pro Ser Cys Gly Asp Ile Cys Asn Phe Pro Pro Lys Ile Ala His Gly
                340                 345                 350

His Tyr Lys Gln Ser Ser Ser Tyr Ser Phe Phe Lys Glu Glu Ile Ile
            355                 360                 365

Tyr Glu Cys Asp Lys Gly Tyr Ile Leu Val Gly Gln Ala Lys Leu Ser
370                 375                 380
```

```
Cys Ser Tyr Ser His Trp Ser Ala Pro Ala Pro Gln Cys Lys Ala Leu
385                 390                 395                 400

Ala Ala Ala Gly Gly Glu Pro Arg Gly Pro Thr Ile Lys Pro Cys Pro
            405                 410                 415

Pro Cys Lys Cys Pro Ala Pro Asn Leu Leu Gly Gly Pro Ser Val Phe
        420                 425                 430

Ile Phe Pro Pro Lys Ile Lys Asp Val Leu Met Ile Ser Leu Ser Pro
        435                 440                 445

Ile Val Thr Cys Val Val Val Asp Val Ser Glu Asp Asp Pro Asp Val
    450                 455                 460

Gln Ile Ser Trp Phe Val Asn Asn Val Glu Val His Thr Ala Gln Thr
465                 470                 475                 480

Gln Thr His Arg Glu Asp Tyr Asn Ser Thr Leu Arg Val Val Ser Ala
            485                 490                 495

Leu Pro Ile Gln His Gln Asp Trp Met Ser Gly Lys Glu Phe Lys Cys
        500                 505                 510

Lys Val Asn Asn Lys Asp Leu Pro Ala Pro Ile Glu Arg Thr Ile Ser
        515                 520                 525

Lys Pro Lys Gly Ser Val Arg Ala Pro Gln Val Tyr Val Leu Pro Pro
    530                 535                 540

Pro Glu Glu Glu Met Thr Lys Lys Gln Val Thr Leu Thr Cys Met Val
545                 550                 555                 560

Thr Asp Phe Met Pro Glu Asp Ile Tyr Val Glu Trp Thr Asn Asn Gly
            565                 570                 575

Lys Thr Glu Leu Asn Tyr Lys Asn Thr Glu Pro Val Leu Asp Ser Asp
        580                 585                 590

Gly Ser Tyr Phe Met Tyr Ser Lys Leu Arg Val Glu Lys Lys Asn Trp
        595                 600                 605

Val Glu Arg Asn Ser Tyr Ser Cys Ser Val Val His Glu Gly Leu His
    610                 615                 620

Asn His His Thr Thr Lys Ser Phe Ser Arg Thr Pro Gly Lys
625                 630                 635

<210> SEQ ID NO 21
<211> LENGTH: 636
<212> TYPE: PRT
<213> ORGANISM: Artificial Sequence
<220> FEATURE:
<223> OTHER INFORMATION: synthesized in laboratory

<400> SEQUENCE: 21

Met Ser Ala Leu Leu Ile Leu Ala Leu Val Gly Ala Ala Val Ala Asp
1               5                   10                  15

Tyr Lys Asp Asp Asp Asp Lys Leu Gly Ala Pro Asn Cys Gly Pro Pro
            20                  25                  30

Pro Thr Leu Ser Phe Ala Ala Pro Met Asp Ile Thr Leu Thr Glu Thr
        35                  40                  45

Arg Phe Lys Thr Gly Thr Thr Leu Lys Tyr Thr Cys Leu Pro Gly Tyr
    50                  55                  60

Val Arg Ser His Ser Thr Gln Thr Leu Thr Cys Asn Ser Asp Gly Glu
65                  70                  75                  80

Trp Val Tyr Asn Thr Phe Cys Ile Tyr Lys Arg Cys Arg His Pro Gly
            85                  90                  95

Glu Leu Arg Asn Gly Gln Val Glu Ile Lys Thr Asp Leu Ser Phe Gly
        100                 105                 110
```

```
Ser Gln Ile Glu Phe Ser Cys Ser Glu Gly Phe Phe Leu Ile Gly Ser
        115                 120                 125
Thr Thr Ser Arg Cys Glu Val Gln Asp Arg Gly Val Gly Trp Ser His
        130                 135                 140
Pro Leu Pro Gln Cys Gly Ser Ile Thr Cys Arg Lys Pro Asp Val Ser
145                 150                 155                 160
His Gly Glu Met Val Ser Gly Phe Gly Pro Ile Tyr Asn Tyr Lys Asp
                165                 170                 175
Thr Ile Val Phe Lys Cys Gln Lys Gly Phe Val Leu Arg Gly Ser Ser
            180                 185                 190
Val Ile His Cys Asp Ala Asp Ser Lys Trp Asn Pro Ser Pro Pro Ala
        195                 200                 205
Cys Glu Pro Asn Ser Cys Ile Asn Leu Pro Asp Ile Pro His Ala Ser
210                 215                 220
Trp Glu Thr Tyr Pro Arg Pro Thr Lys Glu Asp Val Tyr Val Val Gly
225                 230                 235                 240
Thr Val Leu Arg Tyr Arg Cys His Pro Gly Tyr Lys Pro Thr Thr Asp
                245                 250                 255
Glu Pro Thr Thr Val Ile Cys Gln Lys Asn Leu Arg Trp Thr Pro Tyr
            260                 265                 270
Gln Gly Cys Glu Ala Leu Cys Cys Pro Glu Pro Lys Leu Asn Asn Gly
        275                 280                 285
Glu Ile Thr Gln His Arg Lys Ser Arg Pro Ala Asn His Cys Val Tyr
        290                 295                 300
Phe Tyr Gly Asp Glu Ile Ser Phe Ser Cys His Glu Thr Ser Arg Phe
305                 310                 315                 320
Ser Ala Ile Cys Gln Gly Asp Gly Thr Trp Ser Pro Arg Thr Pro Ser
                325                 330                 335
Cys Gly Asp Ile Cys Asn Phe Pro Pro Lys Ile Ala His Gly His Tyr
            340                 345                 350
Lys Gln Ser Ser Ser Tyr Ser Phe Phe Lys Glu Glu Ile Ile Tyr Glu
        355                 360                 365
Cys Asp Lys Gly Tyr Ile Leu Val Gly Gln Ala Lys Leu Ser Cys Ser
370                 375                 380
Tyr Ser His Trp Ser Ala Pro Ala Pro Gln Cys Lys Ala Leu Ala Ala
385                 390                 395                 400
Ala Gly Gly Glu Pro Arg Gly Pro Thr Ile Lys Pro Cys Pro Pro Cys
                405                 410                 415
Lys Cys Pro Ala Pro Asn Leu Leu Gly Gly Pro Ser Val Phe Ile Phe
            420                 425                 430
Pro Pro Lys Ile Lys Asp Val Leu Met Ile Ser Leu Ser Pro Ile Val
        435                 440                 445
Thr Cys Val Val Val Asp Val Ser Glu Asp Asp Pro Asp Val Gln Ile
        450                 455                 460
Ser Trp Phe Val Asn Asn Val Glu Val His Thr Ala Gln Thr Gln Thr
465                 470                 475                 480
His Arg Glu Asp Tyr Asn Ser Thr Leu Arg Val Val Ser Ala Leu Pro
                485                 490                 495
Ile Gln His Gln Asp Trp Met Ser Gly Lys Glu Phe Lys Cys Lys Val
            500                 505                 510
Asn Asn Lys Asp Leu Pro Ala Pro Ile Glu Arg Thr Ile Ser Lys Pro
        515                 520                 525
Lys Gly Ser Val Arg Ala Pro Gln Val Tyr Val Leu Pro Pro Pro Glu
530                 535                 540
```

Glu Glu Met Thr Lys Lys Gln Val Thr Leu Thr Cys Met Val Thr Asp
545                 550                 555                 560

Phe Met Pro Glu Asp Ile Tyr Val Glu Trp Thr Asn Asn Gly Lys Thr
            565                 570                 575

Glu Leu Asn Tyr Lys Asn Thr Glu Pro Val Leu Asp Ser Asp Gly Ser
        580                 585                 590

Tyr Phe Met Tyr Ser Lys Leu Arg Val Glu Lys Lys Asn Trp Val Glu
    595                 600                 605

Arg Asn Ser Tyr Ser Cys Ser Val Val His Glu Gly Leu His Asn His
610                 615                 620

His Thr Thr Lys Ser Phe Ser Arg Thr Pro Gly Lys
625                 630                 635

<210> SEQ ID NO 22
<211> LENGTH: 9
<212> TYPE: PRT
<213> ORGANISM: Artificial Sequence
<220> FEATURE:
<223> OTHER INFORMATION: synthesized in laboratory

<400> SEQUENCE: 22

Tyr Pro Tyr Asp Val Pro Asp Tyr Ala
1               5

<210> SEQ ID NO 23
<211> LENGTH: 14
<212> TYPE: PRT
<213> ORGANISM: Artificial Sequence
<220> FEATURE:
<223> OTHER INFORMATION: synthesized in laboratory

<400> SEQUENCE: 23

Gly Lys Pro Ile Pro Asn Pro Leu Leu Gly Leu Asp Ser Thr
1               5                   10

<210> SEQ ID NO 24
<211> LENGTH: 10
<212> TYPE: PRT
<213> ORGANISM: Artificial Sequence
<220> FEATURE:
<223> OTHER INFORMATION: synthesized in laboratory

<400> SEQUENCE: 24

Glu Gln Lys Leu Ile Ser Glu Glu Asp Leu
1               5                   10

<210> SEQ ID NO 25
<211> LENGTH: 9
<212> TYPE: PRT
<213> ORGANISM: Artificial Sequence
<220> FEATURE:
<223> OTHER INFORMATION: synthesized in laboratory

<400> SEQUENCE: 25

Asp Tyr Lys Asp Asp Asp Asp Lys Gly
1               5

<210> SEQ ID NO 26
<211> LENGTH: 11
<212> TYPE: PRT
<213> ORGANISM: Artificial Sequence
<220> FEATURE:
<223> OTHER INFORMATION: synthesized in laboratory

```
<400> SEQUENCE: 26

Gln Pro Glu Leu Ala Pro Glu Asp Pro Glu Asp
1               5                   10

<210> SEQ ID NO 27
<211> LENGTH: 11
<212> TYPE: PRT
<213> ORGANISM: Artificial Sequence
<220> FEATURE:
<223> OTHER INFORMATION: synthesized in laboratory

<400> SEQUENCE: 27

Tyr Thr Asp Ile Glu Met Asn Arg Leu Gly Lys
1               5                   10

<210> SEQ ID NO 28
<211> LENGTH: 6
<212> TYPE: PRT
<213> ORGANISM: Artificial Sequence
<220> FEATURE:
<223> OTHER INFORMATION: synthesized in laboratory

<400> SEQUENCE: 28

His His His His His His
1               5

<210> SEQ ID NO 29
<211> LENGTH: 11
<212> TYPE: PRT
<213> ORGANISM: Artificial Sequence
<220> FEATURE:
<223> OTHER INFORMATION: synthesized in laboratory

<400> SEQUENCE: 29

Ala Ser Met Thr Gly Gly Gln Gln Met Gly Arg
1               5                   10

<210> SEQ ID NO 30
<211> LENGTH: 870
<212> TYPE: PRT
<213> ORGANISM: Artificial Sequence
<220> FEATURE:
<223> OTHER INFORMATION: synthesized in laboratory

<400> SEQUENCE: 30

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
                20                  25                  30

Val Pro Asn Ile Thr Tyr Gln Cys Met Glu Leu Asn Phe Tyr Lys Ile
            35                  40                  45

Pro Asp Asn Leu Pro Phe Ser Thr Lys Asn Leu Asp Leu Ser Phe Asn
        50                  55                  60

Pro Leu Arg His Leu Gly Ser Tyr Ser Phe Phe Ser Phe Pro Glu Leu
65                  70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
    130                 135                 140
```

-continued

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
            165                 170                 175

Leu Glu His Leu Asp Leu Ser Ser Asn Lys Ile Gln Ser Ile Tyr Cys
        180                 185                 190

Thr Asp Leu Arg Val Leu His Gln Met Pro Leu Leu Asn Leu Ser Leu
    195                 200                 205

Asp Leu Ser Leu Asn Pro Met Asn Phe Ile Gln Pro Gly Ala Phe Lys
210                 215                 220

Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Gly Asn Leu Glu Lys Phe
            260                 265                 270

Asp Lys Ser Ala Leu Glu Gly Leu Cys Asn Leu Thr Ile Glu Glu Phe
        275                 280                 285

Arg Leu Ala Tyr Leu Asp Tyr Tyr Leu Asp Asp Ile Ile Asp Leu Phe
    290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Gly Asn Ala Phe Ser
        355                 360                 365

Glu Val Asp Leu Pro Ser Leu Glu Phe Leu Asp Leu Ser Arg Asn Gly
    370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
        435                 440                 445

Leu Ile Tyr Leu Asp Ile Ser His Thr His Thr Arg Val Ala Phe Asn
    450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
                485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
        515                 520                 525

His Asn Asn Phe Phe Ser Leu Asp Thr Phe Pro Tyr Lys Cys Leu Asn
    530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

```
            Thr Gln Asn Asp Phe Ala Cys Thr Cys Glu His Gln Ser Phe Leu Gln
                            580                 585                 590

Trp Ile Lys Asp Gln Arg Gln Leu Val Glu Val Glu Arg Met Glu
                        595                 600                 605

Cys Ala Thr Pro Ser Asp Lys Gln Gly Met Pro Val Leu Ser Leu Asn
                    610                 615                 620

Ile Thr Cys Gln Met Asn Lys Thr Gly Ala Ala Gly Gly Glu Pro Arg
            625                 630                 635                 640

Gly Pro Thr Ile Lys Pro Cys Pro Pro Cys Lys Cys Pro Ala Pro Asn
                            645                 650                 655

Leu Leu Gly Gly Pro Ser Val Phe Ile Phe Pro Pro Lys Ile Lys Asp
                        660                 665                 670

Val Leu Met Ile Ser Leu Ser Pro Ile Val Thr Cys Val Val Val Asp
                    675                 680                 685

Val Ser Glu Asp Asp Pro Asp Val Gln Ile Ser Trp Phe Val Asn Asn
                    690                 695                 700

Val Glu Val His Thr Ala Gln Thr Gln Thr His Arg Glu Asp Tyr Asn
            705                 710                 715                 720

Ser Thr Leu Arg Val Val Ser Ala Leu Pro Ile Gln His Gln Asp Trp
                            725                 730                 735

Met Ser Gly Lys Glu Phe Lys Cys Lys Val Asn Asn Lys Asp Leu Pro
                        740                 745                 750

Ala Pro Ile Glu Arg Thr Ile Ser Lys Pro Lys Gly Ser Val Arg Ala
                    755                 760                 765

Pro Gln Val Tyr Val Leu Pro Pro Glu Glu Glu Met Thr Lys Lys
                    770                 775                 780

Gln Val Thr Leu Thr Cys Met Val Thr Asp Phe Met Pro Glu Asp Ile
            785                 790                 795                 800

Tyr Val Glu Trp Thr Asn Asn Gly Lys Thr Glu Leu Asn Tyr Lys Asn
                            805                 810                 815

Thr Glu Pro Val Leu Asp Ser Asp Gly Ser Tyr Phe Met Tyr Ser Lys
                        820                 825                 830

Leu Arg Val Glu Lys Lys Asn Trp Val Glu Arg Asn Ser Tyr Ser Cys
                    835                 840                 845

Ser Val Val His Glu Gly Leu His Asn His His Thr Thr Lys Ser Phe
                    850                 855                 860

Ser Arg Thr Pro Gly Lys
            865                 870

<210> SEQ ID NO 31
<211> LENGTH: 825
<212> TYPE: PRT
<213> ORGANISM: Artificial Sequence
<220> FEATURE:
<223> OTHER INFORMATION: synthesized in laboratory

<400> SEQUENCE: 31

Met Pro His Thr Leu Trp Met Val Trp Val Leu Gly Val Ile Ile Ser
 1               5                  10                  15

Leu Ser Lys Glu Glu Ser Asn Gln Ala Ser Leu Ser Cys Asp Arg
                20                  25                  30

Asn Gly Ile Cys Lys Gly Ser Ser Gly Ser Leu Asn Ser Ile Pro Ser
            35                  40                  45

Gly Leu Thr Glu Ala Val Lys Ser Leu Asp Leu Ser Asn Asn Arg Ile
        50                  55                  60
```

```
Thr Tyr Ile Ser Asn Ser Asp Leu Gln Arg Cys Val Asn Leu Gln Ala
 65                  70                  75                  80

Leu Val Leu Thr Ser Asn Gly Ile Asn Thr Ile Glu Glu Asp Ser Phe
                 85                  90                  95

Ser Ser Leu Gly Ser Leu Glu His Leu Asp Leu Ser Tyr Asn Tyr Leu
                100                 105                 110

Ser Asn Leu Ser Ser Ser Trp Phe Lys Pro Leu Ser Ser Leu Thr Phe
            115                 120                 125

Leu Asn Leu Leu Gly Asn Pro Tyr Lys Thr Leu Gly Glu Thr Ser Leu
        130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
                180                 185                 190

Ser Leu Lys Ser Ile Gln Asn Val Ser His Leu Ile Leu His Met Lys
            195                 200                 205

Gln His Ile Leu Leu Glu Ile Phe Val Asp Val Thr Ser Ser Val
        210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
                260                 265                 270

Leu Asn Gln Ile Ser Gly Leu Leu Glu Leu Glu Phe Asp Asp Cys Thr
            275                 280                 285

Leu Asn Gly Val Gly Asn Phe Arg Ala Ser Asp Asn Asp Arg Val Ile
        290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
                340                 345                 350

Cys Leu Leu Ser Gln His Leu Lys Ser Leu Glu Tyr Leu Asp Leu Ser
            355                 360                 365

Glu Asn Leu Met Val Glu Glu Tyr Leu Lys Asn Ser Ala Cys Glu Asp
        370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
                420                 425                 430

Gln Trp Pro Glu Lys Met Lys Tyr Leu Asn Leu Ser Ser Thr Arg Ile
            435                 440                 445

His Ser Val Thr Gly Cys Ile Pro Lys Thr Leu Glu Ile Leu Asp Val
        450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495
```

```
Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
    530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Ala Ala Gly Gly
            580                 585                 590

Glu Pro Arg Gly Pro Thr Ile Lys Pro Cys Pro Pro Cys Lys Cys Pro
        595                 600                 605

Ala Pro Asn Leu Leu Gly Gly Pro Ser Val Phe Ile Phe Pro Pro Lys
    610                 615                 620

Ile Lys Asp Val Leu Met Ile Ser Leu Ser Pro Ile Val Thr Cys Val
625                 630                 635                 640

Val Val Asp Val Ser Glu Asp Asp Pro Asp Val Gln Ile Ser Trp Phe
                645                 650                 655

Val Asn Asn Val Glu Val His Thr Ala Gln Thr Gln Thr His Arg Glu
            660                 665                 670

Asp Tyr Asn Ser Thr Leu Arg Val Val Ser Ala Leu Pro Ile Gln His
        675                 680                 685

Gln Asp Trp Met Ser Gly Lys Glu Phe Lys Cys Lys Val Asn Asn Lys
    690                 695                 700

Asp Leu Pro Ala Pro Ile Glu Arg Thr Ile Ser Lys Pro Lys Gly Ser
705                 710                 715                 720

Val Arg Ala Pro Gln Val Tyr Val Leu Pro Pro Glu Glu Glu Met
                725                 730                 735

Thr Lys Lys Gln Val Thr Leu Thr Cys Met Val Thr Asp Phe Met Pro
            740                 745                 750

Glu Asp Ile Tyr Val Glu Trp Thr Asn Asn Gly Lys Thr Glu Leu Asn
        755                 760                 765

Tyr Lys Asn Thr Glu Pro Val Leu Asp Ser Asp Gly Ser Tyr Phe Met
    770                 775                 780

Tyr Ser Lys Leu Arg Val Glu Lys Lys Asn Trp Val Glu Arg Asn Ser
785                 790                 795                 800

Tyr Ser Cys Ser Val Val His Glu Gly Leu His Asn His His Thr Thr
                805                 810                 815

Lys Ser Phe Ser Arg Thr Pro Gly Lys
            820                 825

<210> SEQ ID NO 32
<211> LENGTH: 592
<212> TYPE: PRT
<213> ORGANISM: Artificial Sequence
<220> FEATURE:
<223> OTHER INFORMATION: synthesized in laboratory

<400> SEQUENCE: 32

Met Glu Arg Ala Ser Cys Leu Leu Leu Leu Leu Pro Leu Val His
1               5                  10                  15

Val Ser Ala Thr Thr Pro Glu Pro Cys Glu Leu Asp Asp Glu Asp Phe
                20                  25                  30
```

-continued

```
Arg Cys Val Cys Asn Phe Ser Glu Pro Gln Pro Asp Trp Ser Glu Ala
             35                  40                  45
Phe Gln Cys Val Ser Ala Val Glu Val Glu Ile His Ala Gly Gly Leu
         50                  55                  60
Asn Leu Glu Pro Phe Leu Lys Arg Val Asp Ala Asp Ala Asp Pro Arg
 65                  70                  75                  80
Gln Tyr Ala Asp Thr Val Lys Ala Leu Arg Val Arg Arg Leu Thr Val
                 85                  90                  95
Gly Ala Ala Gln Val Pro Ala Gln Leu Leu Val Gly Ala Leu Arg Val
            100                 105                 110
Leu Ala Tyr Ser Arg Leu Lys Glu Leu Thr Leu Glu Asp Leu Lys Ile
        115                 120                 125
Thr Gly Thr Met Pro Pro Leu Pro Leu Glu Ala Thr Gly Leu Ala Leu
    130                 135                 140
Ser Ser Leu Arg Leu Arg Asn Val Ser Trp Ala Thr Gly Arg Ser Trp
145                 150                 155                 160
Leu Ala Glu Leu Gln Gln Trp Leu Lys Pro Gly Leu Lys Val Leu Ser
                165                 170                 175
Ile Ala Gln Ala His Ser Pro Ala Phe Ser Cys Glu Gln Val Arg Ala
            180                 185                 190
Phe Pro Ala Leu Thr Ser Leu Asp Leu Ser Asp Asn Pro Gly Leu Gly
        195                 200                 205
Glu Arg Gly Leu Met Ala Ala Leu Cys Pro His Lys Phe Pro Ala Ile
    210                 215                 220
Gln Asn Leu Ala Leu Arg Asn Thr Gly Met Glu Thr Pro Thr Gly Val
225                 230                 235                 240
Cys Ala Ala Leu Ala Ala Ala Gly Val Gln Pro His Ser Leu Asp Leu
                245                 250                 255
Ser His Asn Ser Leu Arg Ala Thr Val Asn Pro Ser Ala Pro Arg Cys
            260                 265                 270
Met Trp Ser Ser Ala Leu Asn Ser Leu Asn Leu Ser Phe Ala Gly Leu
        275                 280                 285
Glu Gln Val Pro Lys Gly Leu Pro Ala Lys Leu Arg Val Leu Asp Leu
    290                 295                 300
Ser Cys Asn Arg Leu Asn Arg Ala Pro Gln Pro Asp Glu Leu Pro Glu
305                 310                 315                 320
Val Asp Asn Leu Thr Leu Asp Gly Asn Pro Phe Leu Val Pro Gly Thr
                325                 330                 335
Ala Leu Pro His Glu Gly Ser Met Asn Ser Gly Val Val Pro Ala Cys
            340                 345                 350
Ala Arg Ala Ala Ala Gly Gly Glu Pro Arg Gly Pro Thr Ile Lys Pro
        355                 360                 365
Cys Pro Pro Cys Lys Cys Pro Ala Pro Asn Leu Leu Gly Gly Pro Ser
    370                 375                 380
Val Phe Ile Phe Pro Pro Lys Ile Lys Asp Val Leu Met Ile Ser Leu
385                 390                 395                 400
Ser Pro Ile Val Thr Cys Val Val Val Asp Val Ser Glu Asp Asp Pro
                405                 410                 415
Asp Val Gln Ile Ser Trp Phe Val Asn Asn Val Glu Val His Thr Ala
            420                 425                 430
Gln Thr Gln Thr His Arg Glu Asp Tyr Asn Ser Thr Leu Arg Val Val
        435                 440                 445
Ser Ala Leu Pro Ile Gln His Gln Asp Trp Met Ser Gly Lys Glu Phe
    450                 455                 460
```

```
Lys Cys Lys Val Asn Asn Lys Asp Leu Pro Ala Pro Ile Glu Arg Thr
465                 470                 475                 480

Ile Ser Lys Pro Lys Gly Ser Val Arg Ala Pro Gln Val Tyr Val Leu
                485                 490                 495

Pro Pro Pro Glu Glu Glu Met Thr Lys Lys Gln Val Thr Leu Thr Cys
            500                 505                 510

Met Val Thr Asp Phe Met Pro Glu Asp Ile Tyr Val Glu Trp Thr Asn
            515                 520                 525

Asn Gly Lys Thr Glu Leu Asn Tyr Lys Asn Thr Glu Pro Val Leu Asp
            530                 535                 540

Ser Asp Gly Ser Tyr Phe Met Tyr Ser Lys Leu Arg Val Glu Lys Lys
545                 550                 555                 560

Asn Trp Val Glu Arg Asn Ser Tyr Ser Cys Ser Val Val His Glu Gly
                565                 570                 575

Leu His Asn His His Thr Thr Lys Ser Phe Ser Arg Thr Pro Gly Lys
                580                 585                 590

<210> SEQ ID NO 33
<211> LENGTH: 725
<212> TYPE: PRT
<213> ORGANISM: Artificial Sequence
<220> FEATURE:
<223> OTHER INFORMATION: synthesized in laboratory

<400> SEQUENCE: 33

Met Arg Glu Asn Met Ala Arg Gly Pro Cys Asn Ala Pro Arg Trp Val
1               5                   10                  15

Ser Leu Met Val Leu Val Ala Ile Gly Thr Ala Val Thr Ala Ala Val
                20                  25                  30

Asn Pro Gly Val Val Val Arg Ile Ser Gln Lys Gly Leu Asp Tyr Ala
            35                  40                  45

Ser Gln Gln Gly Thr Ala Ala Leu Gln Lys Glu Leu Lys Arg Ile Lys
50                  55                  60

Ile Pro Asp Tyr Ser Asp Ser Phe Lys Ile Lys His Leu Gly Lys Gly
65                  70                  75                  80

His Tyr Ser Phe Tyr Ser Met Asp Ile Arg Glu Phe Gln Leu Pro Ser
                85                  90                  95

Ser Gln Ile Ser Met Val Pro Asn Val Gly Leu Lys Phe Ser Ile Ser
            100                 105                 110

Asn Ala Asn Ile Lys Ile Ser Gly Lys Trp Lys Ala Gln Lys Arg Phe
        115                 120                 125

Leu Lys Met Ser Gly Asn Phe Asp Leu Ser Ile Glu Gly Met Ser Ile
130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
            180                 185                 190

Ile Glu Ser Ala Leu Arg Asn Lys Met Asn Ser Gln Val Cys Glu Lys
        195                 200                 205

Val Thr Asn Ser Val Ser Ser Glu Leu Gln Pro Tyr Phe Gln Thr Leu
210                 215                 220

Pro Val Met Thr Lys Ile Asp Ser Val Ala Gly Ile Asn Tyr Gly Leu
225                 230                 235                 240
```

-continued

```
Val Ala Pro Pro Ala Thr Thr Ala Glu Thr Leu Asp Val Gln Met Lys
            245                 250                 255

Gly Glu Phe Tyr Ser Glu Asn His His Asn Pro Pro Phe Ala Pro
        260                 265                 270

Pro Val Met Glu Phe Pro Ala Ala His Asp Arg Met Val Tyr Leu Gly
        275                 280                 285

Leu Ser Asp Tyr Phe Phe Asn Thr Ala Gly Leu Val Tyr Gln Glu Ala
        290                 295                 300

Gly Val Leu Lys Met Thr Leu Arg Asp Asp Met Ile Pro Lys Glu Ser
305                 310                 315                 320

Lys Phe Arg Leu Thr Thr Lys Phe Phe Gly Thr Phe Leu Pro Glu Val
                325                 330                 335

Ala Lys Lys Phe Pro Asn Met Lys Ile Gln Ile His Val Ser Ala Ser
            340                 345                 350

Thr Pro Pro His Leu Ser Val Gln Pro Thr Gly Leu Thr Phe Tyr Pro
            355                 360                 365

Ala Val Asp Val Gln Ala Phe Ala Val Leu Pro Asn Ser Ser Leu Ala
        370                 375                 380

Ser Leu Phe Leu Ile Gly Met His Thr Thr Gly Ser Met Glu Val Ser
385                 390                 395                 400

Ala Glu Ser Asn Arg Leu Val Gly Glu Leu Lys Leu Asp Arg Leu Leu
                405                 410                 415

Leu Glu Leu Lys His Ser Asn Ile Gly Pro Phe Pro Val Glu Leu Leu
            420                 425                 430

Gln Asp Ile Met Asn Tyr Ile Val Pro Ile Leu Val Leu Pro Arg Val
            435                 440                 445

Asn Glu Lys Leu Gln Lys Gly Phe Pro Leu Pro Thr Pro Ala Arg Val
            450                 455                 460

Gln Leu Tyr Asn Val Val Leu Gln Pro His Gln Asn Phe Leu Leu Phe
465                 470                 475                 480

Gly Ala Asp Val Val Tyr Lys Ala Ala Ala Gly Gly Glu Pro Arg Gly
                485                 490                 495

Pro Thr Ile Lys Pro Cys Pro Pro Cys Lys Cys Pro Ala Pro Asn Leu
            500                 505                 510

Leu Gly Gly Pro Ser Val Phe Ile Phe Pro Pro Lys Ile Lys Asp Val
            515                 520                 525

Leu Met Ile Ser Leu Ser Pro Ile Val Thr Cys Val Val Val Asp Val
            530                 535                 540

Ser Glu Asp Asp Pro Asp Val Gln Ile Ser Trp Phe Val Asn Asn Val
545                 550                 555                 560

Glu Val His Thr Ala Gln Thr Gln Thr His Arg Glu Asp Tyr Asn Ser
                565                 570                 575

Thr Leu Arg Val Val Ser Ala Leu Pro Ile Gln His Gln Asp Trp Met
            580                 585                 590

Ser Gly Lys Glu Phe Lys Cys Lys Val Asn Asn Lys Asp Leu Pro Ala
        595                 600                 605

Pro Ile Glu Arg Thr Ile Ser Lys Pro Lys Gly Ser Val Arg Ala Pro
        610                 615                 620

Gln Val Tyr Val Leu Pro Pro Glu Glu Glu Met Thr Lys Lys Gln
625                 630                 635                 640

Val Thr Leu Thr Cys Met Val Thr Asp Phe Met Pro Glu Asp Ile Tyr
                645                 650                 655
```

```
Val Glu Trp Thr Asn Asn Gly Lys Thr Glu Leu Asn Tyr Lys Asn Thr
            660                 665                 670

Glu Pro Val Leu Asp Ser Asp Gly Ser Tyr Phe Met Tyr Ser Lys Leu
        675                 680                 685

Arg Val Glu Lys Lys Asn Trp Val Arg Asn Ser Tyr Ser Cys Ser
    690                 695                 700

Val Val His Glu Gly Leu His Asn His His Thr Thr Lys Ser Phe Ser
705                 710                 715                 720

Arg Thr Pro Gly Lys
                725

<210> SEQ ID NO 34
<211> LENGTH: 238
<212> TYPE: PRT
<213> ORGANISM: Artificial Sequence
<220> FEATURE:
<223> OTHER INFORMATION: synthesized in laboratory

<400> SEQUENCE: 34

Ala Ala Ala Gly Gly Glu Pro Arg Gly Pro Thr Ile Lys Pro Cys Pro
 1               5                  10                  15

Pro Cys Lys Cys Pro Ala Pro Asn Leu Leu Gly Gly Pro Ser Val Phe
            20                  25                  30

Ile Phe Pro Pro Lys Ile Lys Asp Val Leu Met Ile Ser Leu Ser Pro
        35                  40                  45

Ile Val Thr Cys Val Val Asp Val Ser Glu Asp Asp Pro Asp Val
    50                  55                  60

Gln Ile Ser Trp Phe Val Asn Asn Val Glu Val His Thr Ala Gln Thr
65                  70                  75                  80

Gln Thr His Arg Glu Asp Tyr Asn Ser Thr Leu Arg Val Val Ser Ala
                85                  90                  95

Leu Pro Ile Gln His Gln Asp Trp Met Ser Gly Lys Glu Phe Lys Cys
            100                 105                 110

Lys Val Asn Asn Lys Asp Leu Pro Ala Pro Ile Glu Arg Thr Ile Ser
        115                 120                 125

Lys Pro Lys Gly Ser Val Arg Ala Pro Gln Val Tyr Val Leu Pro Pro
    130                 135                 140

Pro Glu Glu Glu Met Thr Lys Lys Gln Val Thr Leu Thr Cys Met Val
145                 150                 155                 160

Thr Asp Phe Met Pro Glu Asp Ile Tyr Val Glu Trp Thr Asn Asn Gly
                165                 170                 175

Lys Thr Glu Leu Asn Tyr Lys Asn Thr Glu Pro Val Leu Asp Ser Asp
            180                 185                 190

Gly Ser Tyr Phe Met Tyr Ser Lys Leu Arg Val Glu Lys Lys Asn Trp
        195                 200                 205

Val Glu Arg Asn Ser Tyr Ser Cys Ser Val Val His Glu Gly Leu His
    210                 215                 220

Asn His His Thr Thr Lys Ser Phe Ser Arg Thr Pro Gly Lys
225                 230                 235

<210> SEQ ID NO 35
<211> LENGTH: 330
<212> TYPE: PRT
<213> ORGANISM: Artificial Sequence
<220> FEATURE:
<223> OTHER INFORMATION: synthesized in laboratory
```

```
<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

ANTI-PATHOGEN IMMUNOADHESINS

CLAIM OF PRIORITY

This application is a National Phase Application of International Patent Application No. PCT/US2005/027944, filed on Aug. 4, 2005, and claims the benefit under 35 USC §119(e) of U.S. Provisional Patent Application Ser. Nos. 60/598,774, filed on Aug. 4, 2004, and 60/668,703, filed on Apr. 6, 2005, the entire contents of which are hereby incorporated by reference.

TECHNICAL FIELD

This invention relates to compounds for modulating immune responses, and methods of using them.

BACKGROUND

The human innate immune system makes use of a number of germ-line encoded transmembrane and cell-surface proteins that recognize highly conserved molecular determinants, known as pathogen-associated molecular patterns (PAMPs), in pathogens including bacteria, fingi, and viruses. These proteins include the transmembrane glycoprotein toll like receptors (TLRs) and other related molecules including CD14, a glycosylphosphatidylinositol (GPI)-anchored cell-surface glycoprotein. Upon encounter with their cognate pathogen-associated molecular pattern-containing ligands (PAMP ligands), these molecules trigger a potent proinflammatory activation program, culminating in the activation of the adaptive immune response and healing.

SUMMARY

The invention relates to the creation and use of recombinant chimeric proteins, referred to herein as anti-pathogen immunoadhesins (APIs), that include a pathogen recognition module (e.g., derived from the binding domain of a pathogen recognition protein, e.g., a Toll-Like Receptor (TLR), Factor H, Complement component C4-binding protein (C4BP), CD14, MD-2, bactericidal/permeability-increasing protein (BPI), scavenger receptors (SRs), surfactant proteins (SP), C-reactive protein (CRP), Mannan-binding lectin (MBL), or complement C1q globular binding domain), and the Fc (fragment crystallizable) portion of an immunoglobulin. In some embodiments, the APIs also include a linker, e.g., a sequence of amino acids between the pathogen recognition module and the Fc. In some embodiments, the linker includes about two to five amino acids, e.g., alanine or glycine.

In general, the API polypeptides described herein include an Fc region, a pathogen recognition module (PRM), and optionally a linker of at least two additional amino acids, e.g., at least three, four, or five amino acids, between the PRM and the Fc region. In some embodiments, the Fc region is derived from a human immunoglobulin or a murine immunoglobulin.

In some embodiments, the PRM is derived from a toll-like receptor (TLR), e.g., TLR4, TLR2, TLR5, TLR6, TLR7, TLR8, or TLR9, or a non-TLR, e.g., Factor H, C4BP, CD14, bacterial permeability increasing protein (BPI), or MD-2. Typically, the PRM includes all of the extracellular domain (ECD) of the protein from which it is derived, but can contain less or more, e.g., can be missing all or part of a signal sequence, subcellular localization sequence, or other non-antigen binding portions of the ECD. The PRM retains the ability to specifically bind to its cognate pathogen-derived PAMP ligand.

In some embodiments, the linker includes at least two amino acids, e.g., alanine and/or glycine. Exemplary linkers include GAAGG (SEQ ID NO:1) or AAAGG (SEQ ID NO:2). In some embodiments, the polypeptide includes a peptide tag, e.g., hemagglutinin (HA) (YPYDVPDYA; SEQ (EQKLISEEDL; SEQ ID NO:24), T7 (ASMTGGQQMGR; SEQ ID NO:29), or FLAG (DYKDDDDKG; SEQ ID NO:25); HSV (QPELAPEDPED; SEQ ID NO:26); VSV-G (YTDIEMNRLGK; SEQ ID NO:27); 6-HIS (HHHHHH; SEQ ID NO:28).

The invention also provides nucleic acids encoding the polypeptides described herein, vectors including the nucleic acids, and host cells including the vectors. Also included are pharmaceutical compositions including an API as described herein, and a pharmaceutically acceptable carrier.

Further, the invention includes an API as described herein, for use in the treatment of a disorder associated with a pathogen. In addition, the invention includes the use of an API as described herein in the manufacture of a medicament for the treatment of a disorder associated with a pathogen.

In another aspect, the invention provides methods for determining the activity of an API. The methods include obtaining a sample includes an API as described herein; contacting the sample with a ligand of a pathogen recognition protein from which the pathogen recognition module (PRM) of the API is derived (e.g., its cognate PAMP or binding portion thereof); and detecting binding of the ligand to the API. Binding of the ligand to the API indicates that the immunoadhesin is active.

Other methods for determining the activity of an API include obtaining a sample includes a test cell expressing the pathogen recognition protein from which the pathogen recognition module (PRM) of the API is derived, wherein the test cell can signal through (i.e., activate a signaling pathway that includes, e.g., begins at) the pathogen recognition protein in response to a ligand of the pathogen recognition protein; contacting the sample with a ligand of the pathogen recognition protein and the API; and determining the level of signaling through the pathogen recognition protein in the test cell compared to a reference. A reduction in the level of signaling in the test cell as compared to a reference indicates that the API is active.

Further, the invention provides methods for identifying and evaluating candidate APIs for use in treating disorders associated with a pathogen. The methods include obtaining a test API; obtaining a sample including a test cell expressing the pathogen recognition protein from which the pathogen recognition module (PRM) of the test API is derived, wherein the test cell can signal through the pathogen recognition protein in response to a ligand of the pathogen recognition protein; contacting the sample with a ligand of the pathogen recognition protein and the API in the presence of the test API; and determining the level of signaling through the pathogen recognition protein in the test cell compared to a reference. A decrease in signaling through the pathogen recognition protein in the test cell as compared to a reference indicates that the test API is a candidate API for treating a disorder associated with a pathogen.

In some embodiments, the reference is a level of signaling through the pathogen recognition protein in the test cell, or in a cell that is the same type as the test cell, in the absence of the test API.

The invention additionally provides methods for identifying candidate API therapeutic agents for use in treating disorders associated with a pathogen. The methods include obtaining a candidate API for treating a disorder associated with a pathogen; administering the candidate API to a model of the disorder (e.g., an animal model of a pathogen-associated infection); and evaluating an effect on the disorder in the model. An improvement in the disorder indicates that the candidate API is a candidate API therapeutic agent for treating a disorder associated with a pathogen.

Further, the invention includes methods for treating disorders associated with a pathogen in a subject, by administering a therapeutically effective amount of an API to the subject. The API can be administered alone (e.g., as a stand-alone treatment) or in combination with, e.g., an antibiotic, steroid, or other treatment. In general, the API can be administered in a therapeutic composition, with a pharmacologically acceptable carrier.

Further, the invention includes methods for removing pathogens, or soluble PAMP ligands, from a fluid, e.g., a liquid such as blood, serum, cell culture media, or beverages, or a gas, such as air. PAMP ligands are proteins that include pathogen-associated molecular patterns (PAMPs), which the pathogen recognition module (PRM) of the API recognizes and binds. PAMP ligands generally include those pathogen components that are given off by the pathogen, e.g., antigenic surface components liberated in a soluble form into the tissue fluids. In addition, PAMP ligands include pathogen components given off during cell death or replication. Exemplary PAMP ligands include LPS and peptidoglycans. The methods include contacting the fluid with an anti-pathogen immunoadhesin (API) under conditions and for a time sufficient to allow pathogen in the fluid to bind the API, thereby forming an API/pathogen complex; and removing the API/pathogen complex from the fluid, thereby removing the pathogen from the fluid. In some embodiments, the API is bound to a substrate, e.g., a collectible substrate or a solid substrate. These methods can be used, e.g., to purify the fluid, or to detect the presence of a pathogen or PAMP ligand in a sample. If the sample is from a subject (e.g., includes blood or urine), the methods can be used to diagnose the presence of a pathogen-associated condition, and identify the pathogen causing the condition.

Disorders associated with a pathogen include, but are not limited to, pathogen-associated infections and inflammatory conditions.

In some embodiments, the pathogen-associated infections are due to bacteria, e.g., *P. aeruginosa, S. pneumoniae, Y. pestis, E. coli, S. typhimurium, N. meningitidis, N. gonorrhoeae, H. influenzae* and *S. aureus*; fungi, e.g., *Aspergillus fumigatus, Candida albicans*, and other zymosan-containing organisms; viruses, e.g., Herpes simplex virus 1 (HSV1), Herpes simplex virus 2 (HSV2), respiratory syncytial virus, measles virus (MV), human cytomegalovirus (HCMV), vaccinia virus, human immunodeficiency virus type 1 (HIV-1), hepatitis A-C virus (HAV, HBV, HCV); spirochetes, e.g., *Borrelia burgdorferi* or *Treponema pallidum*; or parasites, e.g., *Plasmodium* spp. (e.g., *P. bergei* or *P. falciparum*).

As used herein, a "pathogen recognition module derived from the binding domain of a pathogen recognition protein" is an amino acid sequence that is derived from (i.e., is identical to, or at least 80% identical (e.g., 85%, 90%, 95% or more identical) to a portion of) the sequence of a pathogen binding domain of a pathogen recognition protein, and retains the ability to bind to cognate pathogen-associated molecular patterns (PAMPs) with at least 30% of the binding affinity of the native pathogen recognition protein. Alternatively, an API as described herein can include a "synthetic pathogen recognition module," i.e., a peptidomimetic or other synthetic structure that corresponds to, and has a substantially similar three-dimensional structure as, all or a portion of the pathogen binding domain of the pathogen recognition protein, sufficient to retain at least 30% binding affinity of the native protein. In some embodiments, the pathogen recognition module binds to its cognate PAMP with at least about 40%, 50%, 60%, 70%, 80%, 90%, 95%, or 100% of the affinity of the native pathogen recognition protein.

In some embodiments, the sequence of the pathogen recognition module can differ from the sequence of the parent pathogen recognition protein by the addition, deletion, substitution or insertion of amino acids, such that up to about 2%, 5%, 7%, or 10% of the sequence is changed. These changes can be made at the nucleotide or protein level. These variants can, for example, lack a signal sequence, or have an altered signal sequence, that affects the subcellular localization or trafficking of an API of which the variant is a part, e.g., to cause the API to be secreted.

Also within the invention is the use of an API as described herein in the manufacture of a medicament for the treatment of a disorder associated with a pathogen. The medicament can be in any form described herein, and can be administered alone or in combination with, e.g., an antibiotic, steroid, or other treatment.

The present invention has a number of advantages. For example, the APIs described herein are particularly useful anti-pathogen therapeutics because pathogens generally cannot mutate the pathogen-associated molecular patterns (PAMPs), e.g., lipopolysaccharide (LPS) that are recognized by the pathogen recognition proteins. Thus, APIs can be used as anti-pathogenic agents to which the targeted pathogen cannot develop resistance. APIs are also useful as reagents for assays related to the pathogen recognition protein from which the pathogen recognition module of the APIs is derived (e.g., tollbodies, for an assay for a compound that binds to a TLR). In addition, the APIs described herein can be used to purify large amounts of the pathogen-binding domain, e.g., using methods that involve binding the Fc region of the API to a substrate.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, nucleotide and amino acid sequences and other references mentioned herein are incorporated by reference in their entirety. In addition, the materials, methods, and examples are illustrative only and not intended to be limiting.

Other features and advantages of the invention will be apparent from the detailed description, drawings, and from the claims.

DESCRIPTION OF DRAWINGS

FIG. 11A-11C, Heat-killed bacteria were incubated with the TLR2:Fc and CD14:Fc, and subjected to FACS analysis. Note that CD14:Fc bound more efficiently to a Gram+ bacterium (*S. pneumoniae*, FIG. 11A), while TLR2: Fc bound effectively to an intracellular parasite (*L. monocytogenes*, FIG. 11C). TLR2 and CD14 chimeras bound equally well to *E. coli* (DH5α, FIG. 11B). In FIGS. 11D-G, TLR2:Fc was incubated with *N. Meningitidis* (MC58 Capsule-; 11D) or *N. Meningitidis* (MC58 Capsule+; 11E), Factor H:Fc was incubated with *N. Meningitidis* (11F); and BPI:Fc was incubated with *Y. Pestis* (11G). Controls are shown as dashed (11D-E) or solid (11F-G) lines.

FIG. 12A is a line graph illustrating NF-κB expression, monitored as a function of luciferase activity, in HEK 293 cells expressing TLR4 and an NF-κB-luciferase reporter gene. The cells were incubated with titrated amounts of LPS (x-axis), in the presence of increasing amounts of T4:Fc, as shown.

FIG. 12B is a line graph illustrating LPS activation, monitored as a function of IL-6 levels, in cell supernatants from human peripheral blood monocytes (PBMCs), in the presence of autologous serum as a source of soluble MD-2 and in the presence of increasing amounts of T4:Fc, as shown.

FIG. 13 is bar graph illustrating the aggregate results of the experiment in FIG. 4.

FIG. 14 is a bar graph illustrating the effects of Factor H:Fc fusion proteins on complement-mediated killing of sialylated and unsialylated gonococci.

DETAILED DESCRIPTION

Figure 1A:
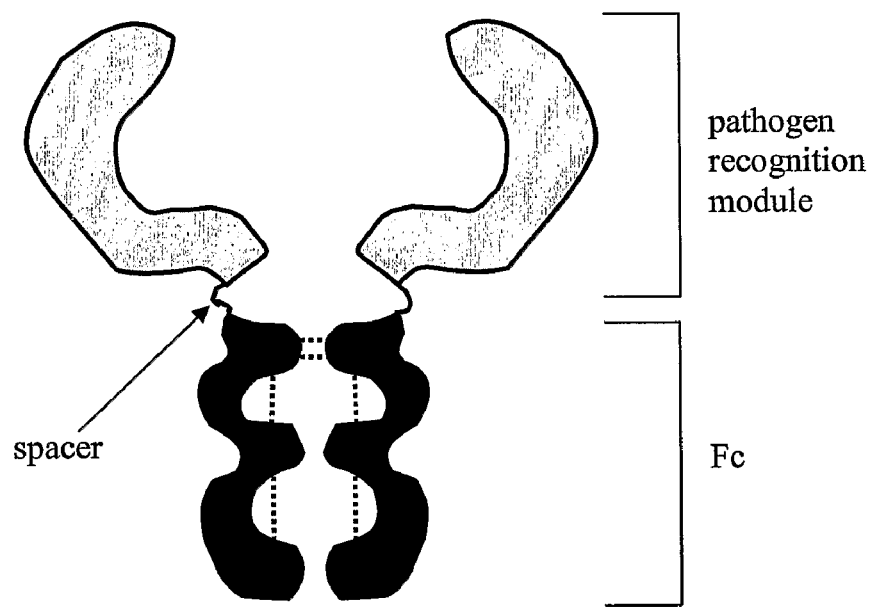
FIG. 1A is a schematic structure of two exemplary anti-pathogen immunoadhesins (APIs), shown as a dimer (gray area, pathogen recognition module; black, Fc portion). Note the disulfide bridges (represented by dashed lines), which include intrachain bridges that stabilize the Ig domains and the interchain bridges that covalently link two immunoadhesin molecules.

Hybrid proteins have been developed that contain a pathogen recognition module (e.g., derived from a sufficient portion of the binding domain of a pathogen recognition protein, e.g., a Toll-Like Receptor (TLR), Factor H, C4BP, CD14, MD-2, or bactericidal/permeability-increasing protein (BPI)) and an immunoglobulin module including the Fc portion of an immunoglobulin (e.g., a murine IgG2a). The molecules are referred to herein as anti-pathogen immunoadhesins (APIs), a subset of which is tollbodies, which have a pathogen recognition module derived from the binding domain of a Toll-Like Receptor (TLR). A schematic illustration of an exemplary API is shown in FIG. 1. As demonstrated herein, APIs can be expressed in cells and can bind to their cognate ligands, i.e., the cognate ligands of the binding domains of their corresponding pathogen recognition proteins.

APIs recognize and can directly interact with pathogen-associated molecular patterns (PAMPs). Ligands that contain these PAMPS are known as PAMP ligands and include pathogen-derived substances such as lipopolysaccharide (LPS) (see Examples 3 and 6-8). APIs are useful, for example, for targeting bacterial, viral, and fungal pathogens, and for producing large quantities of the pathogen recognition molecule. Thus, APIs can be used as therapeutics, e.g., for treating pathogen-associated disorders, e.g., infections and inflammatory conditions (e.g., inflammatory conditions associated with a pathogen-associated infection) and other disorders in which it is desirable to inhibit signaling pathways associated with the pathogen recognition protein from which the extracellular domain of the API is derived. These APIs are particularly useful therapeutics because pathogens generally cannot mutate the PAMPs (e.g., LPS) that are recognized by the pathogen recognition proteins. Thus, APIs can be used as anti-pathogenic agents to which the targeted pathogen cannot develop resistance. APIs are also useful as reagents for assays related to the pathogen recognition protein from which the pathogen recognition module of the API is derived (e.g., tollbodies, for an assay for a compound that binds to a TLR). The APIs described herein can be used for one or more of the following: (1) to neutralize PAMP ligands, e.g., in a fluid, e.g., blood or water; (2) to bind to and activate complement on the surface of a pathogen, thereby accelerating the immune response to the pathogen; and (3) to bind to bacteria and act as a synthetic opsonin, triggering opsonophagocytosis of the pathogen. The APIs can thus be used both in vivo and in vitro/ex vivo, e.g., to remove pathogens from blood or a water supply, or other liquids to be consumed, e.g., beverages, or even in the air, e.g., to combat a weapon of biological warfare.

Without committing to a particular theory, it appears that certain of the APIs described herein can bind to and neutralize soluble proinflammatory mediators (such as lipopolysaccharide (LPS), double-stranded nucleic acid, or coat protein from an invading pathogen). For example, administration of an API to a subject infected with a pathogen that activates signaling through the pathogen recognition protein from which the extracellular domain of the API is derived (e.g., a subject infected with a pathogen that makes a soluble proinflammatory mediator, double-stranded nucleic acid, or a coat protein from an invading pathogen) results in the attenuation of inflammatory and other responses related to the pathogen recognition protein associated with the infection. Alternatively, the immunoadhesin structure should allow for Fc receptor-mediated binding of the chimeric constructs. The Fc portion of the API (e.g., from an IgG or IgM) may be able to act by fixing complement, thus killing the bound pathogen (e.g., a bacterium). Alternatively or in addition, opsonophagocytosis of API-coated pathogens (e.g., bacteria) by professional phagocytes may also occur.

Several types of exemplary APIs were produced and are described in the Examples. These include tollbodies such as a chimeric TLR4:Fc (wild type), TLR9:Fc (wild type), and TLR2:Fc (FLAG epitope and the N terminus), inter alia. All the APIs bound to their respective ligands (LPS, CpG DNA, and MALP2), as evidenced by the data shown in FIGS. 6, 7 and 8. These examples demonstrate that an API can be active (e.g., inhibit the effects of a TLR ligand by binding to the ligand). Since most APIs retain their original leader sequence and have no transmembrane domain, in the absence of additional retention signals they are expected to go through the secretory pathway, and to be secreted into the cell supernatant (e.g., TLR4:Fc as described infra), which can facilitate harvesting and purification of the API. The two cassettes encoding the TLR4:Fc and TLR9:Fc fusion proteins were also subcloned into a retroviral vector, which was used to generate stably transduced cell lines. The ability to stably express an API is useful for producing the same molecule, reproducibly over long periods of time and in quantities that can permit preparation of purified tollbodies.

Additional APIs were engineered and are referred to herein as Factor H:Fc, BPI:Fc, and CD14:Fc. Two forms of the CD14:Fc were made, the CD14:Fc, which includes the first 320 amino acids of CD14; and ΔCD14:Fc, which includes the first 151 amino acids of CD14 (representing the reported minimal LPS binding sequence).

An API referred to as MD-2:Fc was engineered that includes the entire MD-2 protein and the Fc portion of the murine IgG, isotype 2a. In a cell, MD-2 is associated with the ECD of TLR4, and, together with TLR4, acts to activate a TLR associated signaling pathway. MD-2 can bind to LPS without interacting with TLR4. TLR4 (or TLR4:Fc) can bind to LPS only in the presence of MD-2. Molecules that include a polypeptide involved in TLR signaling such as MD-2 can be useful for purposes similar to those of tollbodies or used in conjunction with a tollbody. Since MD-2 binds to LPS, the MD-2:Fc can be used as a sink for LPS, as can the TLR2:Fc. As one theory, not meant to be limiting, the mechanism by which the TLR4:Fc exerts its effect is by sequestrating soluble MD-2 from the supernatant, thereby making LPS unavailable to the surface LPS receptor. Only the monomeric form of MD-2 binds to LPS.

APIs and Pathogen Recognition Modules

An API as described herein is a fusion protein that includes a pathogen recognition module (PRM) derived from all or a portion of the binding domain of a pathogen recognition protein (PRP), e.g., the extracellular domain of a Toll-Like Receptor (TLR), Factor H, C4BP, CD14, MD-2, or bactericidal/permeability-increasing protein (BPI), linked, e.g., covalently fused to an Fc region of an immunoglobulin, with or without an intervening linker as described herein. The portion of the binding domain can be the entire binding domain or a portion thereof sufficient to enable the resulting PRM to bind to the cognate ligand (e.g., the pathogen associated molecular pattern, PAMP) of the PRP with at least 30% of the binding affinity of the PRP.

An API as described herein is generally produced by generating a nucleic acid construct that includes the API, and inserting the construct into an expression vector. The expression vector is then transfected into a suitable cell or cell type for expression, either in vitro or in vivo. The expressed API can be harvested from the cell, either in a crude homogenate or from the supernatant (if the API is secreted). The API can be purified using methods known in the art. In particular, an advantage of using an API is that the protein can be purified using methods that involve binding the Fc region of the API to a substrate.

Figure 1B:
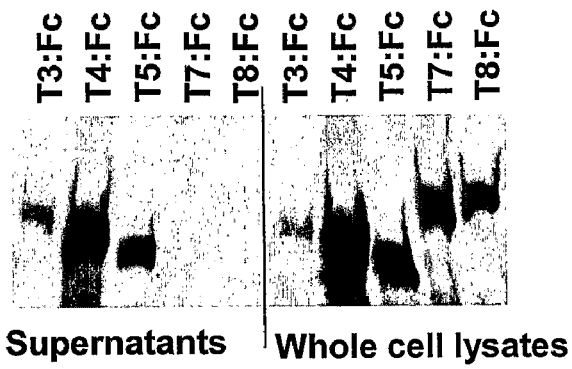
FIGS. 1B and 1C are Western Blots illustrating that some Tollbodies are secreted proteins. The indicated APIs were purified from cell supernatants or whole cell lysates as indicated using protein A Sepharose (PAS) or LPS beads and subjected to PAGE and anti mouse Western blot, followed by ECL.

In general, a construct that can be used to produce an API can be made by PCR amplification of a selected pathogen recognition module using methods known to those in the art, and directional cloning into an Fc acceptor plasmid. The acceptor plasmid generally contains a strong viral eukaryotic promoter (e.g., CMV) and the Fc cDNA. At the N terminus (5') of the Fc acceptor plasmid, there are generally two restriction sites into which the extracellular domain (ECD) can be directionally cloned. The DNA coding for the API that results from cloning the pathogen recognition module into the Fc acceptor plasmid is then sequenced to verify that it is the correct sequence, tested for expression/secretion in a transient expression system, and finally spliced into a retroviral vector using recombinant techniques, to generate a stable expression system. The resulting API molecule is schematically represented in FIG. 1A, which illustrates a typical dimeric form. The binding domain of a pathogen recognition protein is shown in gray, and the Fc portion is shown in black. The dashed lines represent disulfide bridges, which include the intrachain bridges that stabilize the Ig domains and the interchain bridges that covalently link two immunoadhesin molecules.

Tollbodies

APIs including pathogen recognition modules derived from the extracellular domain (ECD) of a Toll-Like Receptor (TLR) are referred to herein as tollbodies. Pathogen recognition modules derived from the ECD of a TLR can be identified by the presence of highly conserved leucine rich repeats (LRR) (see, e.g., Bell et al., TRENDS in Immunology 24:10: 528-533 (2003), i.e., common motifs of about twenty amino acids with several leucine residues located at fixed intervals; the pathogen recognition module will typically consist of several LRR, including several glycosylation consensus sequences, and can consist of the whole ECD of a given toll-like receptor. It is thought that the LRRs are also responsible for protein-protein interactions. Stretches of LRRs confer a horseshoe shape to the LRR-containing polypeptide, by forming alpha helices facing the external surface and beta sheets defining a hydrophobic core. The structure of TLR3 was published in Bell et al., Proc Natl Acad Sci USA. 102 (31):10976-10980 (2005). Intervening amino acid sequences interspersed among the LRR are thought to be responsible for conferring ligand binding specificity; they usually reside in the beta sheet side of the molecule.

Figure 1C:
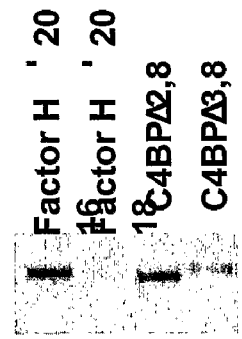

TLR ECDs are heavily N-glycosylated and possess a high number of cysteine residues. Both these characteristics are thought to stabilize the horseshoe fold and contribute to the ligand binding specificities. TLRs 1-4 are thought to be glycosylated in the Golgi apparatus and exposed on the cell surface, and TLR2:Fc and TLR4:Fc are readily secreted (FIG. 1B), as are Factor H:Fc and C4BP:Fc (FIG. 1C). A few APIs (e.g., TLR3:Fc, TLR5:Fc, and TLR7-9:Fc) were not readily secreted into the supernatant, despite the fact their predicted transmembrane region was removed. The ECD is responsible for the homophilic aggregation that is observed after LPS-induced clustering of TLR4 and for the heterodimerization thought to occur between TLR2 and either TLR1 or TLR6. As shown in the examples, below, TLR2:Fc pairing with a different TLR is not necessary to bind to the cognate ligand: the API can specifically bind to MALP-2, Pam3CysK, and Neisserial porin without another TLR.

The pathogen recognition module can be derived from toll-like receptors including, but not limited to, toll-like receptor 1, *Homo sapiens* (GeneID: 7096; UniGene Cluster Hs.111805; NCBI Accession #NP_003254.2, AAC34137.1); toll-like receptor 2, *Homo sapiens* (GeneID: 7097; UniGene Cluster Hs.519033; NCBI Accession #AAH33756.1, AAM23001.1, AAC34133.1); toll-like receptor 3, *Homo sapiens* (GeneID: 7098; UniGene Cluster Hs.29499; NCBI Accession #AAC34134.1, NP_003256.1); toll-like receptor 4, *Homo sapiens* (GeneID: 7099 (var. C); UniGene Cluster Hs.174312; NCBI Accession #AAC34135.1, AAF89753.1, AAF07823.1, AAF05316.1); toll-like receptor 5, *Homo sapiens* (GeneID: 7100; UniGene Cluster Hs.114408; NCBI Accession #AAC34136.1, BAB43955.1); toll-like receptor 6, *Homo sapiens* (GeneID: 10333; UniGene Cluster Hs.366986; NCBI Accession #NP_006059.2, BAA78631.1); toll-like receptor 7, *Homo sapiens* (GeneID: 51284; UniGene Cluster Hs.179152; NCBI Accession #AAF60188.1, AAF78035.1, NP_057646.1, AAH33651.1); toll-like receptor 8, *Homo sapiens* (GeneID: 51311; UniGene Cluster Hs.272410; NCBI Accession #AAF64061, AAF78036.1); toll-like receptor 9 *Homo sapiens* (GeneID: 54106; UniGene Cluster Hs.87968; NCBI Accession # AAG01734.1, AAG01735.1, AAG01736.1, BAB19259.1); toll-like receptor 10, *Homo sapiens* (GeneID: 81793; UniGene Cluster Hs.120551; NCBI Accession #AAK26744.1, NP_112218.2); toll-like receptor 1, *Mus musculus* (GeneID: 21897; UniGene Cluster Mm.273024; NCBI Accession #AAG35062.1, AAG37302.1, NP_109607.1); toll-like receptor 2, *Mus musculus* (GeneID: 24088; UniGene Cluster Mm.87596; NCBI Accession #AAD46481.1, AAF04277.1, AAD49335.1, NP_036035.2, AAF28345.1); toll-like receptor 3, *Mus musculus* (GeneID: 142980; UniGene Cluster Mm.33874; NCBI Accession #AAK26117.1, AAL27007.1, NP_569054.2); toll-like receptor 4, *Mus musculus* (GeneID: 21898; UniGene Cluster Mm.38049; NCBI Accession #AAD29272.1, AAF04278.1, AAF05317.1, NP_067272.1, AAH29856.1); toll-like receptor 5, *Mus musculus* (GeneID: 53791; UniGene Cluster Mm.116894, Mm.347908; NCBI Accession #AAF65625.1, NP_058624.1); toll-like receptor 6, *Mus musculus* (GeneID: 21899; UniGene Cluster Mm.42146, Mm.347552; NCBI Accession #BAA78632.1, AAG38563.1, NP_035734.2); toll-like receptor 7, *Mus musculus* (GeneID: 170743; Uni-Gene Cluster Mm.23979; NCBI Accession #AAK62676.1, NP_573474.1, AAL73191.1, AAL73192.1); toll-like receptor 8, *Mus musculus* (GeneID: 170744; UniGene Cluster Mm.196676; NCBI Accession #NP_573475.1, AAK62677.1); and toll-like receptor 9, *Mus musculus* (GeneID: 81897; UniGene ClusterMm.44889; NCBI Accession#BAB19260.1, AAK29625.1, AAK28488.1, NP_112455.1); and homologs thereof. A pathogen-induced product-detection domain can also be isolated from a molecule that binds to, is activated by, or is inhibited by toll-like-receptor-pathway-related molecules.

In some embodiments, the complete TLR4:Fc API comprises SEQ ID NO:30:

(SEQ ID NO: 30)
MMSASRLAGTLIPAMAFLSCVRPESWEPCVEVVPNITYQCMELNFYKIPD

NLPFSTKNLDLSFNPLRHLGSYSFFSFPELQVLDLSRCEIQTIEDGAYQS

LSHLSTLILTGNPIQSLALGAFSGLSSLQKLVAVETNLASLENFPIGHLK

TLKELNVAHNLIQSEKLPEYFSNLTNLEHLDLSSNKIQSIYCTDLRVLHQ

MPLLNLSLDLSLNPMNFIQPGAFKEIRLHKLTLRNNFDSLNVMKTCIQGL

AGLEVHRLVLGEFRNEGNLEKFDKSALEGLCNLTIEEFRLAYLDYYLDDI

IDLFNCLTNVSSFSLVSVTIERVKDFSYNFGWQHLELVNCKFGQFPTLKL

KSLKRLTFTSNKGGNAFSEVDLPSLEFLDLSRNGLSFKGCCSQSDFGTTS

LKYLDLSFNGVITMSSNFLGLEQLEHLDFQHSNLKQMSEFSVFLSLRNLI

YLDISHTHTRVAFNGIFNGLSSLEVLKMAGNSFQENFLPDIFTELRNLTF

LDLSQCQLEQLSPTAFNSLSSLQVLNMSHNNFFSLDTFPYKCLNSLQVLD

YSLNHIMTSKKQELQHFPSSLAFLNLTQNDFACTCEHQSFLQWIKDQRQL

LVEVERMECATPSDKQGMPVLSLNITCQMNKTGAAGGEPRGPTIKPCPPC

KCPAPNLLGGPSVFIFPPKIKDVLMISLSPIVTCVVVDVSEDDPDVQISW

FVNNVEVHTAQTQTHREDYNSTLRVVSALPIQHQDWMSGKEFKCKVNNKD

LPAPIERTISKPKGSVRAPQVYVLPPPEEEMTKKQVTLTCMVTDFMPEDI

YVEWTNNGKTELNYKNTEPVLDSDGSYFMYSKLRVEKKNWVERNSYSCSV

VHEGLHNHHTTKSFSRTPGK.

In some embodiments, the complete TLR2:Fc API comprises SEQ ID NO:31:

(SEQ ID NO: 31)
MPHTLWMVWVLGVIISLSKEESSNQASLSCDRNGICKGSSGSLNSIPSGL

TEAVKSLDLSNNRITYISNSDLQRCVNLQALVLTSNGINTIEEDSFSSLG

SLEHLDLSYNYLSNLSSSWFKPLSSLTFLNLLGNPYKTLGETSLFSHLTK

LQILRVGNMDTFTKIQRKDFAGLTFLEELEIDASDLQSYEPKSLKSIQNV

SHLILHMKQHILLLEIFVDVTSSVECLELRDTDLDTFHFSELSTGETNSL

IKKFTFRNVKITDESLFQVMKLLNQISGLLELEFDDCTLNGVGNFRASDN

DRVIDPGKVETLTIRRLHIPRFYLFYDLSTLYSLTERVKRITVENSKVFL

VPCLLSQHLKSLEYLDLSENLMVEEYLKNSACEDAWPSLQTLILRQNHLA

SLEKTGETLLTLKNLTNIDISKNSFHSMPETCQWPEKMKYLNLSSTRIHS

VTGCIPKTLEILDVSNNNLNLFSLNLPQLKELYISRNKLMTLPDASLLPM

LLVLKISRNAITTFSKEQLDSFHTLKTLEAGGNNFICSCEFLSFTQEQQA

```
LAKVLIDWPANYLCDSPSHVRGQQVQDVRLSVSECHRAAAGGEPRGPTIK

PCPPCKCPAPNLLGGPSVFIFPPPKIKDVLMISLSPIVTCVVVDVSEDDPD

VQISWFVNNVEVHTAQTQTHREDYNSTLRVVSALPIQHQDWMSGKEFKCK

VNNKDLPAPIERTISKPKGSVRAPQVYVLPPPEEEMTKKQVTLTCMVTDF

MPEDIYVEWTNNGKTELNYKNTEPVLDSDGSYFMYSKLRVEKKNWVERNS

YSCSVVHEGLHNHHTTKSFSRTPGK.
```

CD14 Immunoadhesins

Pathogen recognition modules derived from CD14 can include all or part of the N-terminal portion of either the soluble or membrane form of the molecule. For example, fragments including amino acids 1-152 of the soluble form or 1-151 of the membrane form have been shown to be functional LPS receptors (see, e.g., Viriyakosol and Kirkland, Infect. Immun. 64(2):653-6 (1996); Juan et al., J. Biol. Chem. 270:1382-1387 (1995)). Larger fragments can also be used, e.g., about the first 200, 300, 320, 340 or more amino acids. The mature CD14 membrane protein is composed of 356 amino acids, with four N-linked glycosylation sites. A nineteen amino acid signal sequence is removed during processing. The membrane form of CD14 is anchored to the cell surface via a glycosylphosphatidyl-inositol (GPI) linkage. At least two soluble forms of CD14 have been described; one soluble form is produced by shedding of a portion of the membrane form, resulting in an approximately 48 kDa molecule (Bazil and Strominger, J. Immunol. 147:1567-1574 (1991); Bazil et al., Eur. J. Immunol. 16:1583-1589 (1986); Haziot et al., J. Immunol. 141:547-552 (1988); Haziot et al., J. Immunol. 150:5556-65 (1993)), and a second soluble form is released from cells before addition of the GPI anchor, which results in a higher molecular weight form (LaBeta et al., Eur. J. Immunol. 23:2144-2151 (1993), Landmann et al., J. Infect. Dis. 171:639-644 (1995), Bufler et al., Eur. J. Immunol. 25:604-610 (1995)). The crystal structure of CD14 was published by Kim et al., J Biol. Chem. 280(12):11347-51 (2005).

For example, the CD14 pathogen recognition modules can be derived from, e.g., *Mus musculus* CD14 (GeneID: 929; UniGene Cluster Hs.163867; NCBI Accession #CAA32166.1, BAB68578.1, NP_033971.1) or *Homo sapiens* CD14 (GeneID: 12475; UniGene Cluster Mm.3460; NCBI Accession #AAH10507.1, AAL02401.1, CAD36116.1). In some embodiments, the pathogen recognition module contains only the extracellular domain of CD14.

In some embodiments, the complete CD14:Fc API comprises SEQ ID NO:32:

```
                                    (SEQ ID NO: 32)
MERASCLLLLLLPLVHVSATTPEPCELDDEDFRCVCNFSEPQPDWSEAFQ

CVSAVEVEIHAGGLNLEPFLKRVDADADPRQYADTVKALRVRRLTVGAAQ

VPAQLLVGALRVLAYSRLKELTLEDLKITGTMPPLPLEATGLALSLRLRN

VSWATGRSWLAELQQWLKPGLKVLSIAQAHSPAFSCEQVRAFPALTSLDL

SDNPGLGERGLMAALCPHKFPAIQNLALRNTGMETPTGVCAALAAAGVQP

HSLDLSHNSLRATVNPSAPRCMWSSALNSLNLSFAGLEQVPKGLPAKLRV

LDLSCNRLNRAPQPDELPEVDNLTLDGNPFLVPGTALPHEGSMNSGVVPA

CARAAAGGEPRGPTIKPCPPCKCPAPNLLGGPSVFIFPPPKIKDVLMISLS

PIVTCVVVDVSEDDPDVQISWFVNNVEVHTAQTQTHREDYNSTLRVVSAL

PIQHQDWMSGKEFKCKVNNKDLPAPIERTISKPKGSVRAPQVYVLPPPEE

EMTKKQVTLTCMVTDFMPEDIYVEWTNNGKTELNYKNTEPVLDSDGSYFM

YSKLRVEKKNWVERNSYSCSVVHEGLHNHHTTKSFSRTPGK.
```

MD-2 Immunoadhesins

MD-2 (also known as LY96 (lymphocyte antigen 96)) is believed to act in concert with TLR4, to bind to LPS and initiate LPS-induced signaling (Shimazu et al., J. Exp. Med. 189(11):1777-1782 (1999)). MD-2 is believed to physically associate with TLR4 on the cell surface, forming a multimeric receptor complex.

The MD-2 pathogen recognition modules can be derived from, e.g., *Homo sapiens* MD-2 (GeneID: 23643; UniGene Cluster Hs.69328; NCBI Accession #NP_056179.1, BAA78717.1, AAH20690.1), or *Mus musculus* MD-2 (GeneID: 17087; UniGene Cluster Mm.116844; NCBI Accession #BAA93619.1).

BPI Immunoadhesins

Bactericidal/permeability-increasing protein (BPI) is a natural LPS binding protein that kills cells. The BPI pathogen recognition modules can be derived from, e.g., *Homo sapiens* BPI (GeneID: 671; UniGene Cluster Hs.303523; NCBI Accession #NM_001725.1), and can include, e.g., the LPS-binding domain from BPI (amino acids 1-199) (Abrahamson et al. (1997) Journal of Biological Chemistry 272, 2149-2155; Beamer et al. (1998) Protein Science 7, 906-914).

In some embodiments, the complete BPI:Fc API comprises SEQ ID NO:33:

```
                                    (SEQ ID NO: 33)
MRENMARGPCNAPRWVSLMVLVAIGTAVTAAVNPGVVVRISQKGLDYASQ

QGTAALQKELKRIKIPDYSDSFKIKHLGKGHYSFYSMDIREFQLPSSQIS

MVPNVGLKFSISNANIKISGKWKAQKRFLKMSGNFDLSIEGMSISADLKL

GSNPTSGKPTITCSSCSSHINSVHVHISKSKVGWLIQLFHKKIESALRNK

MNSQVCEKVTNSVSSELQPYFQTLPVMTKIDSVAGINYGLVAPPATTAET

LDVQMKGEFYSENHHNPPPFAPPVMEFPAAHDRMVYLGLSDYFFNTAGLV

YQEAGVLKMTLRDDMIPKESKFRLTTKFFGTFLPEVAKKFPNMKIQIHVS

ASTPPHLSVQPTGLTFYPAVDVQAFAVLPNSSLASLFLIGMHTTGSMEVS

AESNRLVGELKLDRLLLELKHSNIGPFPVELLQDIMNYIVPILVLPRVNE

KLQGKFPLPTPARVQLYNVVLQPHQNFLLFGADVVYKAAAGGEPRGPTIK

PCPPCKCPAPNLLGGPSVFIFPPPKIKDVLMISLSPIVTCVVVDVSEDDPD

VQISWFVNNVEVHTAQTQTHREDYNSTLRVVSALPIQHQDWMSGKEFKCK

VNNKDLPAPIERTISKPKGSVRAPQVYVLPPPEEEMTKKQVTLTCMVTDF

MPEDIYVEWTNNGKTELNYKNTEPVLDSDGSYFMYSKLRVEKKNWVERNS

YSCSVVHEGLHNHHTTKSFSRTPGK.
```

RP105

RP105 (also known as Ly78 (lymphocyte antigen 78)) is believed to be involved in LPS recognition in B cells. The RP105 pathogen recognition modules can be derived from, e.g., *Mus musculus* (GeneID: 17079; UniGene Cluster Mm.3300; NCBI Accession #BAA07043.1).

LPS-binding Protein (LBP)

LPS is transferred from the bacterium to MD-2 by the enzymatic activities of LBP and CD14. LPB pathogen recognition domain can be derived from, e.g., amino acids 1-197 of LPS-binding protein (LBP) (S. L. Abrahamson et al. (1997) Journal of Biological Chemistry 272, 2149-2155; L. J. Beamer et al. (1998) Protein Science 7, 906-914). The LPB pathogen recognition modules can be derived from, e.g., *Homo sapiens* LBP (GeneID: 3929; UniGene Hs.154078; NCBI Accession #NP_004130.2).

Factor H and C4 Binding Protein (C4BP)

Factor H and C4BP are complement-regulatory molecules whose main role is to limit the conversion of active C3b to inhibit the lytic effector system. The binding of Factor H and C4BP to the surface of some bacteria confer them a "protective" effect against the C-dependent lysis. Factor H and C4BP APIs possess enzymatic activity or multimerizing domains that might limit their use as bacteria recognition modules. Therefore, in some embodiments these functional domains are deleted, and only the combinations of those domains known to be required for binding to bacteria are used for the PRM (Ram et al., Int Immunopharmacol 1:423-32 (2001); Ram et al., J Exp Med 193:281 (2001)).

Factor H pathogen recognition molecules can be derived from, e.g., *Homo sapiens* (GeneID: 3075; UniGene Hs.363396; NCBI Accession #NP_000177.2 or P08603). In some embodiments, the Factor H PRM includes one or more CCP/Sushi domains described in Table 1, which form the PAMP binding domain; the numbers refer to the amino acids of NCBI Accession #NP_000177.2. For example, the Factor H PRM may include CCP/Sushi domains 6-20, or 18-20, or other combinations of CCP/Sushi domains sufficient to bind to the cognate PAMP.

TABLE 1

CCP/Sushi domains of human complement factor H

| Description | Begin Position | End Position |
|---|---|---|
| CCP/Sushi 1 | 19 | 82 |
| CCP/Sushi 2 | 83 | 143 |
| CCP/Sushi 3 | 144 | 207 |
| CCP/Sushi 4 | 208 | 264 |
| CCP/Sushi 5 | 265 | 322 |
| CCP/Sushi 6 | 324 | 386 |
| CCP/Sushi 7 | 387 | 444 |
| CCP/Sushi 8 | 446 | 507 |
| CCP/Sushi 9 | 515 | 566 |
| CCP/Sushi 10 | 567 | 625 |
| CCP/Sushi 11 | 628 | 686 |
| CCP/Sushi 12 | 689 | 746 |
| CCP/Sushi 13 | 751 | 805 |
| CCP/Sushi 14 | 809 | 866 |
| CCP/Sushi 15 | 868 | 928 |
| CCP/Sushi 16 | 929 | 986 |
| CCP/Sushi 17 | 987 | 1045 |
| CCP/Sushi 18 | 1046 | 1104 |
| CCP/Sushi 19 | 1107 | 1165 |
| CCP/Sushi 20 | 1170 | 1230 |

In some embodiments, the complete Factor H:Fc API comprises SEQ ID NO:18 or 19:

(SEQ ID NO: 18)

MSALLILALVGAAVADYKDDDDKLGAPCKSPPEISHGVVAHMSDSYQYGE

EVTYKCFEGFGIDGPAIAKCLGEKWSHPPSCIKTDCLSLPSFENAIPMGE

KKDVYKAGEQVTYTCATYYKMDGASNVTCINSRWTGRPTCRDTSCVNPPT

VQNAYIVSRQMSKYPSGERVRYQCRSPYEMFGDEEVMCLNGNWTEPPQCK

DSTGKCGPPPPIDNGDITSFPLSVYAPASSVEYQCQNLYQLEGNKRITCR

NGQWSEPPKCLHPCVISREIMENYNIALRWTAKQKLYSRTGESVEFVCKR

-continued

GYRLSSRSHTLRTTCWDGKLEYPTCAKRAAAGGEPRGPTIKPCPPCKCPA

PNLLGGPSVFIFPPKIKDVLMISLSPIVTCVVVDVSEDDPDVQISWFVNN

VEVHTAQTQTHREDYNSTLRVVSALPIQHQDWMSGKEFKCKVNNKDLPAP

IERTISKPKGSVRAPQVYVLPPPEEEMTKKQVTLTCMVTDFMPEDIYVEW

TNNGKTELNYKNTEPVLDSDGSYFMYSKLRVEKKNWVERNSYSCSVVHEG

LHNHHTTKSFSRTPGK (SEQ ID NO: 19)

MSALLILALVGAAVADYKDDDDKLGAPCVNPPTVQNAYIVSRQMSKYPSG

ERVRYQCRSPYEMFGDEEVMCLNGNWTEPPQCKDSTGKCGPPPPIDNGDI

TSFPLSVYAPASSVEYQCQNLYQLEGNKRITCRNGQWSEPPKCLHPCVIS

REIMENYNIALRWTAKQKLYSRTGESVEFVCKRGYRLSSRSHTLRTTCWD

GKLEYPTCAKRAAAGGEPRGPTIKPCPPCKCPAPNLLGGPSVFIFPPKIK

DVLMISLSPIVTCVVVDVSEDDPDVQISWFVNNVEVHTAQTQTHREDYNS

TLRVVSALPIQHQDWMSGKEFKCKVNNKDLPAPIERTISKPKGSVRAPQV

YVLPPPEEEMTKKQVTLTCMVTDFMPEDIYVEWTNNGKTELNYKNTEPVL

DSDGSYFMYSKLRVEKKNWVERNSYSCSVVHEGLHNHHTTKSFSRTPGK

Complement 4 bp (C4BP) pathogen recognition molecules can be derived from, e.g., *Homo sapiens* (GeneID: 722; UniGene Hs.1012; NCBI Accession #NP_000706). In some embodiments, the complete C4BP:Fc comprises SEQ ID NO:20 (CCP 1+3−7) or 21 (CCP 1−2+4−7):

(SEQ ID NO: 20)

MSALLILALVGAAVADYKDDDDKLGAPNCGPPPTLSFAAPMDITLTETRF

KTGTTLKYTCLPGYVRSHSTQTLTCNSDGEWVYNTFCGSVKCKPPPDIRN

GRHSGEENFYAYGFSVTYSCDPRFSLLGHASISCTVENETIGVWRPSPPT

CEKITCRKPDVSHGEMVSGFGPIYNYKDTIVFKCQKGFVLRGSSVIHCDA

DSKWNPSPPACEPNSCINLPDIPHASWETYPRPTKEDVYVVGTVLRYRCH

PGYKPTTDEPTTVICQKNLRWTPYQGCEALCCPEPKLNNGEITQHRKSRP

ANHCVYFYGDEISFSCHETSRFSAICQGDGTWSPRTPSCGDICNFPPKIA

HGHYKQSSSYSFFKEEIIYECDKGYILVGQAKLSCSYSHWSAPAPQCKAL

AAAGGEPRGPTIKPCPPGKCPAPNLLGGPSVFIFPPKIKDVLMISLSPIV

TCVVVDVSEDDPDVQISWFVNNVEVHTAQTQTHREDYNSTLRVVSALPIQ

HQDWMSGKEFKCKVNNKDLPAPIERTISKPKGSVRAPQVYVLPPPEEEMT

KKQVTLTCMVTDFMPEDIYVEWTNNGKTELNYKNTEPVLDSDGSYFMYSK

LRVEKKNWVERNSYSCSVVHEGLHNHHTTKSFSRTPGK (SEQ ID NO: 21)

MSALLILALVGAAVADYKDDDDKLGAPNCGPPPTLSFAAPMDITLTETRF

KTGTTLKYTCLPGYVRSHSTQTLTCNSDGEWVYNTFCIYKRCRHPGELRN

GQVEIKTDLSFGSQIEFSCSEGFFLIGSTTSRCEVQDRGVGWSHPLPQCG

SITCRKPDVSHGEMVSGFGPIYNYKDTIVFKCQKGFVLRGSSVIHCDADS

KWNPSPPACEPNSCINLPDIPHASWETYPRPTKEDVYVVGTVLRYRCHPG

YKPTTDEPTTVICQKNLRWTPYQGCEALCCPEPKLNNGEITQHRKSRPAN

HCVYFYGDEISFSCHETSRFSAICQGDGTWSPRTPSCGDICNFPPKIAHG

-continued
HYKQSSSYSFFKEEIIYECDKGYILVGQAKLSCSYSHWSAPAPQCKALAA

AGGEPRGPTIKPCPPCKCPAPNLLGGPSVFIFPPPKIKDVLMISLSPIVTC

VVVDVSEDDPDVQISWFVNNVEVHTAQTQTHREDYNSTLRVVSALPIQHQ

DWMSGKEFKCKVNNKDLPAPIERTISKPKGSVRAPQVYVLPPPEEEMTKK

QVTLTCMVTDFMPEDIYVEWTNNGKTELNYKNTEPVLDSDGSYFMYSKLR

VEKKNWVERNSYSCSVVHEGLHNHHTTKSFSRTPGK

Fc Modules

The mouse and human immunoglobulin (IgG) heavy chain has four Ig-like domains termed $V_H$ (Variable heavy) and $C_{H1}$ (Constant heavy 1) to $C_{H3}$ (Constant heavy 3). A "hinge" region separates the $C_{H1}$ and $C_{H2}$ domains. The hinge region contains a variable number of cysteine residues (three in the mouse $IgG_{2a}$) that can form covalent interchain bonds between two identical immunoglobulin heavy chains. The portion of an immunoglobulin comprising the hinge region plus the domains $C_{H2}$ and $C_{H3}$ is called fragment crystallizable (Fc). There are several different human and other mammalian (e.g., murine) IgG molecules. For example, the human equivalent of mouse IgG2a is the IgG1. Several immunotherapeutic agents for human therapy include the human IgG1 Fc portion. A portion of the Fc molecules is used to prepare the Fc portion of the chimeric API molecules described herein.

The APIs can contain sequences from the same species or from different species. For example, an interspecies hybrid API can contain a murine Fc region and a human sequence from a TLR protein. The APIs described herein also include those that are made entirely from murine-derived sequences (i.e., a murine TLR extracellular domain and a murine Fc region) or fully human (i.e., a human TLR extracellular domain and a human Fc region). In general, both the pathogen recognition module and the Fc region of an API for use in a specific animal species are derived from that animal species. Thus, a human TLR:human Fc tollbody is generally used in humans. However, interspecies APIs can be used (e.g., for local administration) provided they do not provide unacceptable levels of deleterious effects; typically, after the first treatment organisms will mount an immune response against the xenochimera, which limits the usefulness of such molecules, unless they are co-administered with immune suppressive treatments.

General methods of preparing immunoadhesins are known in the art (Ashkenazi, A. and S. M. Chamow (1997), "Immunoadhesins as research tools and therapeutic agents," Curr. Opin. Immunol. 9(2): 195-200, Chamow, S. M. and A. Ashkenazi (1996). "Immunoadhesins: principles and applications," Trends Biotechnol. 14(2):52-60). In general, to generate an API, the sequences encoding the hinge region of an Ig are retained and a region coding for a short (e.g., about 5 amino acid) linker is added between the pathogen recognition module coding region and the region coding for the Fc (n-terminal to the hinge). The main effector region of the Fc (i.e., the region that binds complement and protein A, and the single glycosylation site that is required to stabilize an Fc dimer—the effector functions are C-terminal to the hinge region) should be included.

In one example, an API can be made by cloning into an expression vector such as pcDNA3 (Invitrogen) a nucleic acid sequence encoding a TLR ECD in-frame with a sequence encoding an Fc portion of an Ig (e.g., the Fc portion of an IgG such as an IgG2a).

In one embodiment, the Fc portion and a linker (in bold print below) has the murine sequence:

(SEQ ID NO: 34)
AAAGGEPRGPTIKPCPPCKCPAPNLLGGPSVFIFPPPKIKDVLMISLSPIV

TCVVVDVSEDDPDVQISWFVNNVEVHTAQTQTHREDYNSTLRVVSALPIQ

HQDWMSGKEFKCKVNNKDLPAPIERTISKPKGSVRAPQVYVLPPPEEEMT

KKQVTLTCMVTDFMPEDIYVEWTNNGKTELNYKNTEPVLDSDGSYFMYSK

LRVEKKNWVERNSYSCSVVHEGLHNHHTTKSFSRTPGK.

In other embodiments, the Fc portion can be derived from the human Ig gamma-1 chain C region (Swiss-Prot Accession No. P01857), in which the hinge starts from residue 99:

(SEQ ID NO: 35)
ASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVD

KKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTV

DKSRWQQGNVFSCSVMHEALHNHYTQKSLSLSPGK.

Linkers

In some embodiments, the API construct includes a linker, e.g., in the form of additional residues, e.g., alanine and/or glycine residues, between the pathogen recognition module and the Fc/Ig hinge region. The total number of linker residues (in addition to glycine residues that are naturally occurring in the Ig from which the hinge region is derived) can be, e.g., at least 2, 3, 4, 5, 6, or 7. To minimize the possibility of immunological rejection of the molecule and retain expression and proper folding other residues can be used. These include naturally occurring Ig hinge regions or part of non structured regions of human extracellular proteins. As a general rule, when designing a Tollbody hinge region, peptide sequences including small, slightly hydrophilic amino acids such as glycine, alanine, serine, threonine, methionine are preferred over charged, ring or aromatic residues. Thus, the total number of resides, e.g., alanine and/or glycine residues in the linker region can be, e.g., at least 2, 3, 4, 5, 6, 7, 8, or 9. Examples of linkers include GAAGG (SEQ ID NO:1) and AAAGG (SEQ ID NO:2). These examples are not to be construed as limiting and in general, a linker that results in an API that can bind to its cognate ligand is encompassed by the invention. In some embodiments, the nucleic acid sequence that encodes the linker includes a restriction enzyme recognition site, e.g., Not I, to facilitate generation of API constructs.

Anti-Pathogen Immunoadhesin (API) Proteins

The methods and compositions described herein can be used to make APIs that are highly purified. Such highly purified proteins can be used, e.g., in binding assays or competition assays to identify compounds that bind to a pathogen recognition protein (such as a TLR) and thus are candidate compounds for inhibiting or enhancing signaling through the protein (e.g., TLR signaling). The use of purified protein in binding assays has several advantages over the use of proteins that are in cellular lysates. For example, buffers can easily be changed allowing the use of a buffer system that is optimal for ligand binding or binding competition assays. Furthermore, certain components of lysis buffers such as detergents, ion chelating agents (e.g., EDTA), or protease inhibitors may adversely influence ligand binding or prevent potential interactors from interfering with binding to an API.

In addition, the use of a purified API protein (e.g., a tollbody) can reduce the number of steps used in an assay to detect binding events. This is because the Fc-portion of the protein can be detected directly using protein A or protein G conjugated to an enzyme (such as HRP or alkaline phosphatase). Alternatively, the Fc portion of an API can be detected using an enzyme-conjugated anti-mouse antibody.

Constructs encoding APIs can be transfected into a cell using methods known in the art. The cells can be cultured under conditions suitable for expression of the cloned API. Suitable cells include HEK293 (human), COS7 (monkey), and CHO (hamster) cells, although for production purposes, any eukaryotic cell type that can be engineered to produce a correctly folded and glycosylated API of interest can be used, including insect expression systems. In general, cells that produce antibodies (e.g., B cells) are not used.

The API vector or construct (a vector that encodes an API) can be further engineered such that a secretory signal is part of the API. Methods are known in the art for engineering a nucleic acid sequence to encode a secretory signal such that an API is secreted or embedded in the membrane. An inducible promoter can also be positioned to control the expression of the API so that expression of the API can be induced. Examples of such inducible promoters include a metallothionein promoter, a tetracycline sensitive promoter (tet-on tet-off), or a copper-inducible promoter. In addition, an API vector can have a retroviral backbone and/or include a gene that confers antibiotic resistance to a cell. Thus, transfected or transduced cells can be selected using the antibiotic to which the gene encodes a resistance protein to select for a stable transgene.

APIs can be detectably labeled for various uses such as those described herein. Labeled APIs (such as tollbodies) can be used, for example, as commercially produced reagents for use in assays of pathogen recognition proteins (such as TLRs) and in methods for identifying compounds that bind to the proteins (e.g., the TLRs).

Examples of detectable labels include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); examples of bioluminescent materials include luciferase (which oxidates luciferin or luminol, producing light as a byproduct), luciferin, luminol and aequorin, and examples of suitable radioactive material include $^{125}I$, $^{131}I$, $^{35}S$, $^{32}P$ or $^{3}H$. Methods of linking such molecules to a polypeptide are known in the art.

In some embodiments, an API is labeled by including an additional moiety such as a FLAG epitope in the hybrid protein (e.g., by engineering a vector that encodes desired API-FLAG hybrid protein), a fluorescent protein like the green fluorescent protein and its spectrum variants, or by coupling (e.g., covalently linking) a detectable moiety such as a fluorescent molecule to the API.

Assays for API Activity

The APIs described herein have one or more of the following activities: (1) inhibit bacterial proliferation, (2) trigger complement-mediated cytotoxicity, (3) function as an artificial opsonin, and/or (4) bind to and neutralize the proinflammatory activity of pathogens or soluble PAMP ligands, e.g., when they are shed by pathogens (e.g., after replication or death). For example, some APIs might bind to and kill bacteria, but not activate complement deposition; other APIs might enhance phagocytosis, but not activate complement, and vice-versa. Methods are described herein that can be used, e.g., to evaluate an API to measure the efficiency with which the API neutralizes the pathogens to which it binds, e.g., by these three modes of action.

Ligand Binding Assays

In one example of a binding assay, an API is bound to a solid substrate such as a microtiter plate, the bound API is incubated with a PAMP ligand for the protein from which the ECD portion of the API is derived, the substrate is washed to remove unbound ligand, and the ligand is detected. Samples can also be assayed in which a test compound is included with the ligand. The amount of binding of ligand to the API in the presence and absence of the test compound is assayed and a test compound that decreases the amount of ligand binding is a candidate compound for modulating signaling of the API. In such assays, a purified API can be used and such a purified protein can be attached to the substrate using a non-specific means. For example, the API can be immobilized via adsorption of the protein to high protein binding microtiter plates or via binding to protein A (or protein G, anti-mouse) coated plastic. Alternatively, an assay can be performed in which the ligand is bound to the solid substrate and the API is incubated with the bound ligand in the presence and absence of the test compound. After incubating for a suitable amount of time to permit binding of the API to the ligand, the samples are washed and the amount of API bound to the ligand is detected, e.g., using methods that detect the Fc portion of the API or that physically detect a tag coupled to the immunoadhesin (see above). A difference in the amount of binding of the API in the presence of the test compound indicates that the test compound is a candidate compound for modulating signaling of the API.

Assays using purified APIs are an improvement over the use of cellular lysates containing pathogen recognition proteins, as cellular lysates may contain DNA binding proteins that can interact with the CpG-DNA used in certain ligand binding assays. Thus, the total amount of binding may be limited by the amount of non-specific, non-target binding to the ligand. Using purified recombinant protein in the ligand binding assay reduces the possibility of ligand masking by other ligand interactors.

An "isolated" or "purified" polypeptide or protein (e.g., an API or fragment thereof) is substantially free of cellular material or other contaminating proteins from the cell or tissue source from which the protein is derived, or substantially free from chemical precursors or other chemicals when chemically synthesized. The term "substantially free" means a preparation of an API having less than about 30% (by dry weight), of non-API protein (also referred to herein as a "contaminating protein"), or of chemical precursors. In some embodiments, the preparation has less than about 20%, 10%, or 5% of non-API protein by dry weight. When the API protein is recombinantly produced, it is also generally substantially free of culture medium, i.e., culture medium represents less than about 20% of the volume of the protein preparation. In some embodiments, the culture medium represents less than about 10%, or less than about 5% of the volume. An API as described herein includes isolated or purified preparations of at least 0.01 milligrams in dry weight; in some embodiments, the preparation is at least 0.1, 1.0, and/or 10 milligrams in dry weight. In general, when the API is a secreted protein, cells are maintained in protein free media, therefore such preparations are substantially free of contaminating protein.

The API or test compound with a label, e.g., a radioisotope or non-isotopic label, such that binding can be determined by detecting the labeled compound in a complex. For example, the API can be labeled with $^{125}$I, $^{35}$S, $^{14}$C, or $^{3}$H, either directly or indirectly, and the radioisotope detected by direct counting of radioemission or by scintillation counting. Alternatively, API or test compounds can be directly or indirectly enzymatically labeled with, for example, biotin, horseradish peroxidase, alkaline phosphatase, or luciferase, and the enzymatic label detected by determination of conversion of an appropriate substrate to product. For example, biotin-LPS can be detected using an avidin-HRP stain. See, e.g., Visintin et al., J. Biol. Chem. 278:48313 (2003).

The ability of an API to interact with a PAMP ligand with or without the labeling of any of the interactants can be evaluated. For example, a microphysiometer can be used. See, e.g., McConnell et al., Science 257:1906-1912 (1992). As used herein, a "microphysiometer" (e.g., Cytosensor®, Molecular Devices Corporation, Sunnyvale Calif.) is an analytical instrument that measures the rate at which a cell acidifies its environment using a light-addressable potentiometric sensor (LAPS). Changes in this acidification rate can be used as an indicator of an interaction.

Soluble forms of PAMP ligands will generally be used in the assays described herein. When less-soluble or non-soluble species are used (e.g., lipid A), it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, isotridecypoly(ethylene glycol ether)n, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In some embodiments, the assay is carried out in a defined solution containing human serum, human serum albumin, or other serum components.

In some embodiments, the methods described herein include applying an API to a test sample including a cell or living tissue or organ, and evaluating one or more activities of the API, e.g., the ability of the API to neutralize a PAMP ligand, to bind and/or activate complement, and/or to bind a pathogen and trigger opsonophagocytosis.

In some embodiments, the test sample is, or is derived from (e.g., a sample originally taken from) an in vivo model of a disorder as described herein. For example, an animal model, e.g., a rodent such as a rat, that is infected with a pathogen can be used, and the ability of the API to improve one or more symptoms of the disorder, e.g., clinically relevant symptoms, is evaluated.

Methods for evaluating each of these effects are known in the art; some are described herein.

A test compound that has been screened by a method described herein and determined to be active, e.g., to neutralize a PAMP ligand, to bind and activate complement, and/or to bind a pathogen and trigger opsonophagocytosis, can be considered a candidate compound. A candidate compound that has been screened, e.g., in an in vivo model of a disorder, e.g., an animal infected with a gram negative bacterium or administered a dose of LPS, and determined to have a desirable effect on the disorder, e.g., on one or more symptoms of the disorder, can be considered a candidate therapeutic agent.

Candidate therapeutic agents, once screened in a clinical setting and found to be effective, are therapeutic agents. Candidate compounds, candidate therapeutic agents, and therapeutic agents can be optionally optimized and/or derivatized, and formulated with physiologically acceptable excipients to form pharmaceutical compositions.

Compounds that interfere with binding of LPS and MD-2 or LPS and TLR4 can be identified using, e.g., cell-based or cell free assays, as are known in the art. Such compounds can also be further screened in animal models.

Opsonophagocytosis Assays

Phagocytosis is an important mechanism of bacteria killing and clearance from the site of infection. APIs might play an important role as opsonins in addition to their direct role in activating complement. APIs are chimeric proteins that contain the immunoglobulin Fc domain and preliminary studies demonstrated that they can bind Fc receptors on macrophages. When APIs coat bacteria, they will likely provide anchorage sites to the Fc receptors on the surface of phagocytes and promote the Fc receptor-mediated phagocytosis of the bacterial particles. These internalized API-coated particles would be decomposed intracellularly and the components would be directed to the antigen "presentation" machinery. In addition, shed API ligands might directly enter the presentation pathways via Fc receptor internalization, thus enhancing their presentation. Either outcome would be of pivotal importance for the healing process and the establishment of an immune memory.

API-mediated opsonization might trigger bacterial killing via MAC (membrane attack complex) deposition on their cell walls, while promoting phagocytosis and cell mediated killing by professional phagocytes. The efficiency of APIs as artificial opsonins can be measured by evaluating enhanced opsonophagocytosis and antigen internalization in vitro. For example, two mechanisms of bacterial entry into cells in vitro can be evaluated: 1) uptake by "non-professional" phagocytes such as the HEK293 human embryonic kidney cell line and 2) uptake by the macrophage-like cell lines THP-1 and RAW and by human macrophages. With "non-professional" phagocytes such as HEK293 cells, bacterial binding to cells that have been transfected with different fluorescence-tagged Fc receptors can be visually followed.

We have established stably transduced cell lines expressing CD36 tagged with yellow fluorescence protein (YFP) or CD16 tagged with cyan fluorescence protein (CFP). Both receptors can be visualized in living cells by confocal microscopy, e.g., using a Leica TCS SP2 AOBS inverted confocal microscope equipped with four laser beams (including a pulse laser for FLIM analysis) and a warmed stage. Confocal microscopy can be used to follow the formation of Fc receptor clusters around API-treated bacteria. The experiments can be conducted under protein-free conditions to minimize interference from serum components. Bacteria are expected to bind specifically to the Fc receptors only when they are coated with the Fc-containing APIs. With API bridging via their Fc portion, a fluorescent "cup" will form at the interface bacteria/cell membrane. HEK293 cells, which do not normally internalize bacteria, also might become internalization competent.

To establish whether APIs can enhance phagocytosis in professional phagocytes, similar experiments can be performed, e.g., with macrophage-like cell lines such as THP-1 and RAW, and with human macrophages purified from the blood of healthy donors. Cellular internalization of bacteria that have been coated with API can be measured, with uncoated bacteria serving as controls. Commercially available Fc receptor-blocking antibodies can be used to determine the contribution of API opsonization. It is expected that under protein-free conditions, non-professional phagocytes will efficiently internalize bacteria only if they are coated with API, whereas professional phagocytes will internalize both coated and uncoated bacteria but API coating will accelerate or enhance bacterial uptake. Bacterial internalization can be measured, e.g., quantitatively by flow cytometry of cells that have been with incubated with fluorescence-tagged bacteria.

Cell mediated killing can be measured by harvesting the cells used for the phagocytosis assay (or by lysing them directly on plastic after washing or killing the non adherent bacteria with antibiotics) and determining the number of colony forming units of bacteria from the lysates.

Animal Models

Also included herein are methods of screening compounds by administering an API to an animal model of a pathogen-associated disorder. Suitable animal models are known in the art, e.g., mammals, such as mice, rats, or monkeys, infected with a gram-negative bacterium such as *Escherichia coli, Helicobacter pylori*, or mammals administered a sub-lethal dose of purified LPS. In some embodiments, the animal is a model of gram-negative induced septic shock.

The methods include administering at least one dose of an API to the animal model, and monitoring the animal for an effect of the compound on the disorder in the animal, e.g., an effect on a clinically relevant parameter, e.g., a parameter that is related to a clinical symptom of the disease as described herein. Methods for selecting, evaluating and scoring such parameters are known in the art. In some embodiments, where the animal is given a sub-lethal dose of purified LPS, the animal is evaluated to see if administering an API rescues the animal.

The animal can be monitored for a change in the disorder, e.g., for an improvement in a parameter of the disorder, e.g., a parameter related to clinical outcome. In some embodiments, the parameter is fever (a trend towards or a return to normal, e.g., a decrease, would be an improvement); blood pressure (a return to normal, e.g., an increase, would be an improvement); heart rate (a trend towards or a return to normal, e.g., a decrease, would be an improvement); and respiration rate (a trend towards or a return to normal, e.g., a decrease, would be an improvement); levels of white blood cells (a trend towards or a return to normal would be an improvement); the level of oxygen (a trend towards or a return to normal, e.g., an increase, would be an improvement); the number of platelets (a trend towards or a return to normal, e.g., an increase, would be an improvement); lactic acid levels (a trend towards or a return to normal, e.g., a decrease, would be an improvement); and levels of metabolic waste products (a trend towards or a return to normal, e.g., a decrease, would be an improvement).

Pharmaceutical Compositions

An API can be incorporated into a pharmaceutical composition. Such compositions typically include the immunoadhesin and a pharmaceutically acceptable carrier. As used herein the language "pharmaceutically acceptable carrier" includes solvents, dispersion media, coatings, antibacterial and antifungal agents, isotonic and absorption delaying agents, and the like compatible with pharmaceutical administration. Supplementary active compounds can also be incorporated into the compositions.

A pharmaceutical composition is formulated to be compatible with its intended route of administration. Examples of routes of administration include oral or parenteral, e.g., intravenous, intradermal, subcutaneous, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, e.g., tromethamine; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifingal agents, for example, parabens, chlorobutanol, phenol, ascorbic acid, thimerosal, and the like. In many cases, it will be desirable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate, and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Such compositions can also be compounded to minimize exposure to gastric enzymes or to facilitate uptake by the intestinal tract.

For administration by inhalation, the compounds can be delivered in the form of an aerosol spray, e.g., from a pressurized container or dispenser that contains a suitable propellant, e.g., a gas such as carbon dioxide, or a nebulizer. Metered dose inhalers are known in the art and can be used. The administration by inhalation can also be used to treat more than one individual at a time, e.g., to treat an area or a number of people exposed to a pathogen.

Systemic administration can also be by transmucosal or transdermal means. For transmucosal or transdermal administration, penetrants appropriate to the barrier to be permeated can be used in the formulation. Such penetrants are generally known in the art, and include, for example, for transmucosal administration, detergents and liposomes. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery. Such preparations are particularly useful for treating conditions associated with pathogen invasion of the lower intestinal tract.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Oral or parenteral compositions can be provided in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of pharmaceutical compounds containing an API can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in to minimize potential damage to non-target cells (e.g., cells that are not undergoing an undesirable inflammatory reaction) and, thereby, reduce side effects. In general, the APIs described herein should be well-tolerated by an animal (e.g., mouse, non-human primate, or human).

The data obtained from the cell culture assays and animal studies can be used in formulating a range of dosage for use in humans. The dosage of such compounds lies generally within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models (e.g., of infection or inflammatory disease) to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography or ELISA.

As defined herein, a therapeutically effective amount of an API (i.e., an effective dosage) is an amount sufficient to exert a therapeutically beneficial effect. One in the art will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of an API can include a single treatment or can include a series of treatments.

Generally, partially and fully human APIs are expected to have a longer half-life within the human body are used for treatment of humans. Accordingly, lower dosages and less frequent administration is often possible. Modifications such as lipidation can be used to stabilize an API and to enhance uptake and tissue penetration (e.g., into the brain). A method for lipidation of antibodies is described by Cruikshank et al. (1997, J. Acquired Immune Deficiency Syndromes and Human Retrovirology 14:193) and can be adapted for use with APIs. Another method for increasing stability is to conjugate the API with human serum albumin The pharmaceutical compositions can be included in a container, pack, or dispenser together with instructions for administration.

Treatment Methods and Compositions

Provided herein are methods and compositions for both prophylactic and therapeutic methods of treating a subject at risk of (or susceptible to) a disorder or having a disorder associated with a pathogen, e.g., as described herein. Such disorders include inflammation, endotoxin-related diseases and conditions such as sepsis, and other pathogen-triggered chronic conditions and disorders (e.g., Crohn's disease and rheumatoid arthritis). Septic shock is usually preceded by sepsis, which is marked by shaking, chills, fever, weakness, confusion, nausea, vomiting, and diarrhea. Early signs of septic shock include confusion and decreased consciousness; shaking chills; a rapid rise in temperature; warm, flushed skin; a rapid, pounding pulse; excessively rapid breathing; and blood pressure that rises and falls. As the shock progresses the extremities become cool, pale, and bluish over time, and fever may give way to lower than normal temperatures. In some embodiments, the methods include administering a compound described herein, e.g., a TLR4:Fc, to a subject who is exhibiting one or more symptoms of sepsis, to prevent the development of septic shock.

Other symptoms of shock include rapid heartbeat, shallow, rapid respiration, decreased urination, and reddish patches in the skin. In some cases, septic shock progresses to "adult respiratory distress syndrome (ARDS)," in which fluid collects in the lungs, and respiration becomes very shallow and labored. ARDS may lead to ventilatory collapse, in which the subject can no longer breathe adequately without assistance.

Tollbodies described herein, e.g., TLR2:Fc and TLR4:Fc, can be used to treat sterile inflammation, in which immune cells release inflammatory chemicals in the absence of any infection. Sterile inflammation is a condition common to a number of different diseases, including, but not limited to, autoimmune diseases, e.g., rheumatoid arthritis. Symptoms of sterile inflammation include those listed in the American College of Rheumatology (ACR) response criteria, which include changes in number of swollen joints, tender joints, physician global assessment of disease, patient global assessment of disease, patient assessment of pain, C-reactive protein (CRP), erythrocyte sedimentation rate (ESR), and health assessment questionnaire (HAQ) score. In some embodiments, treating results in at least an $ACR_{20}$ response, in which the subject has a 20% reduction in the number of swollen and tender joints, and a reduction of 20% in three of the following five indices: physician global assessment of disease, patient global assessment of disease, pain, CRP/ESR and HAQ.

As antibiotics or bacteriostatics, APIs can be used to recognize pathogens and affect the ability of such pathogens to survive and reproduce. As anti-inflammatory drugs, APIs can bind and neutralize pathogen derived substances that are normally TLR ligands, i.e., PAMP ligands, including but not limited to LPS, lipoproteins, lipoteichoic acid (LTA), peptidoglycan (PGN), flagellin, CpG DNA and bacterial porins, which are all proinflammatory signals.

As used herein, the term "treatment" is defined as the application or administration of a therapeutic agent (e.g., an agent comprising an API) to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent can be an API, a recombinant nucleic acid encoding an API, or an API that has been modified as described herein.

Pathogens that can be targeted using the APIs described herein include microorganisms, e.g., gram-positive and gram-negative bacteria, including, but not limited to, *Pseudomonas aeruginosa, Streptococcus pneumoniae, Yersinia pestis, Escherichia coli, Salmonella typhimurium, Neisseria meningitidis, Neisseria gonorrhoeae, Haemophilus influenzae* and *Staphylococcus aureus*; fungi such as *Aspergillus fumigatus, Candida albicans*, and other zymosan-containing organisms (zymosan is a yeast cell-wall component that includes a PAMP); as well as viruses such as Herpes simplex virus 1 (HSV1), Herpes simplex virus 2 (HSV2), respiratory syncytial virus, measles virus (MV), human cytomegalovirus (HCMV), vaccinia virus, human immunodeficiency virus type 1 (HIV-1), hepatitis C virus (HCV); spirochetes including *Borrelia burgdorferi* or *Treponema pallidum*, and parasites including *Plasmodium* spp. *berghei* or *falciparum*. Any pathogen that expresses a PAMP recognizable by a pathogen recognition protein can be targeted with an API with the cognate pathogen recognition domain as described herein.

An API can be delivered to a subject at risk for developing a disorder (e.g., after exposure to a biological weapon such as anthrax or a bacterium that can cause illness, or before major surgery) or to treat an existing condition. APIs can be delivered using methods known in the art, for example, systemically, or by direct delivery to a desired site such as joint or other area of a subject's body in which it is desirable to inhibit a pathogen-related response such as inflammation, e.g., by injection or inhalation, e.g., of an aerosol; delivery by an aerosol may be particularly useful in the case of exposure to an airborne pathogen.

APIs can also be delivered using a recombinant particle such as a recombinant adenovirus containing an expressible nucleic acid sequence encoding the API. Such methods are known in the art (e.g., U.S. Pat. No. 5,998,598).

The APIs described herein can also be used for the preparation of a medicament for use in any of the methods of treatment described herein.

Liquid Purification Therapy

The methods of treating disorders associated with a pathogen as described herein include the use of liquid, e.g., blood, purification methods. These methods can include temporarily removing blood from a subject, treating the blood with an API to remove soluble PAMP ligands and pathogens, and returning the blood to the subject. General methods for performing such purifications (sometimes referred to as "apheresis") are known in the art, and typically involve passing the blood over a column or other device to extract a selected impurity, see, e.g., U.S. Pat. No. 6,569,112 (Strahilevitz); Asahi et al., Therapeutic Apheresis 7(1):74-77(5), 2003; Hout et al., ASAIO J., 46(6):702-206, 2000; Matsuo et al., Therapeutic Apheresis and Dialysis 8(3): 194, 2004. These methods can be adapted for use in the present method. For example, a column or solid substrate including the API can be constructed using methods known in the art, and the blood can be passed through it, removing a substantial amount of the PAMP ligands and/or pathogens present in the blood.

Alternatively, a collectible substrate, e.g., beads, e.g., magnetic beads, can be coated with the API, and the blood can be mixed with the beads, and the beads then extracted to removed the PAMP ligands and pathogens. In some embodiments, the blood is separated into its components before being passed over the column or contacted with the beads. In some embodiments, the methods can be used to remove PAMP ligands and pathogens from the blood, by using a column or other collectible substrate with covalently linked APIs, which will pull PAMP ligands and pathogens out of the blood. In some embodiments, more than one type of API is used, and more than one type of PAMP ligand or pathogen is removed.

One of skill in the art will appreciate that these methods and other known fluid, e.g., liquid or gas, collection and filtering methods can also be adapted to include the APIs described herein for use in purifying liquids other than blood, e.g., water or any beverage, or media for use in culturing cells, as well as gases, such as air.

Methods of Diagnosis

APIs as described herein can be used for diagnostic purposes. By selecting the proper pathogen recognition module, one can use the immunoadhesins to recognize pathogens and pathogen-derived ligands with specificity. For example, a tollbody that includes the ECD of a TLR3 is useful for detecting certain viruses, e.g., viral infection or contamination. TLR5 specifically recognizes bacterial flagellin; therefore, a tollbody that includes the ECD of a TLR5 can be used to detect bacteria expressing flagellin. There are few diagnostic tools for identifying lipopolysaccharide (LPS) contamination or infection in a sample such as a pharmaceutical product, food, or patient sample (e.g., blood, plasma, or a solid tissue sample). APIs that include a pathogen recognition module that binds to LPS (e.g., tollbodies with pathogen recognition modules derived from the ECD of TLR2 or TLR4) are useful for detecting bacterial infection sample in a subject or bacterial contamination of an environmental sample.

In particular, CD14:Fc immunoadhesins as described herein can be used to recognize molecular determinants in addition to or other than LPS, e.g., to test for lipoproteins. Such assays can be performed by immobilizing a sample (e.g., water or a body fluid such as saliva, blood, serum, plasma, CSF, or urine), contacting the sample with a detecting reagent that is a cocktail of labeled APIs, washing, and then detecting the bound immunoadhesins. By using different labels for each type of immunoadhesin in the cocktail, it can be determined which are binding to the sample and thereby determine the nature of the pathogen.

Thus, included herein are methods for diagnosing a disorder associated with a pathogen. The methods include obtaining a sample from a subject, contacting the sample with an API as described herein under conditions sufficient to allow the API and pathogen to form complexes, and evaluating the presence and/or level of a PAMP ligand or pathogen in the sample by detecting the complexes. The methods can also include comparing the presence and/or level with one or more references, e.g., a control reference that represents a normal level of PAMP ligand or pathogen, e.g., a level in an unaffected subject (typically non-detectable), and/or a disease reference that represents a level of PAMP ligand or pathogen, associated with the disorder, e.g., a level in a subject having a disorder associated with the pathogen. The presence and/or level of a protein can be evaluated using methods described herein, or other methods known in the art.

In some embodiments, the presence and/or level of PAMP ligand or pathogen is comparable to the presence and/or level PAMP ligand or pathogen in the disease reference, and if the subject also has one or more symptoms associated with a pathogen associated disorder, then the subject has a pathogen associated disorder. In some embodiments, the subject has no overt signs or symptoms of a pathogen associated disorder, but the presence and/or level of PAMP ligand or pathogen is comparable to the presence and/or level of PAMP ligand or pathogen in the disease reference, then the subject has a pathogen associated disorder. In some embodiments, the sample includes a biological fluid, e.g., blood, semen, urine, and/or cerebrospinal fluid. In some embodiments, once it has been determined that a person has a pathogen associated disorder, then a treatment, e.g., as known in the art or as described herein, can be administered.

Also included herein are methods for detecting a PAMP ligand or pathogen in biological or other samples, e.g., fluids such as blood, cell culture media, beverages, water, or air. The methods include obtaining a sample, and evaluating the presence and/or level of the PAMP ligand or pathogen in the sample using an assay described herein, e.g., an assay that detects the presence and/or level of PAMP ligand or pathogen in the sample by detecting the presence of an API/PAMP ligand complex. In some embodiments, the methods include comparing the presence and/or level with one or more references, e.g., a control reference that represents a preselected level, e.g., a level above which the fluid is unsafe to use. These methods can be used in place of, or in addition to, e.g., Limulus amoebocyte lysate assays, which have limited use in blood (see, e.g., Hurley, Clinical Microbiology Reviews, 8(2):268-292 (1995).

In some embodiments, the sample is from a subject, and the presence of PAMP ligand or pathogen in the sample indicates that the subject has a pathogen-associated disorder. These methods have the advantage that PAMP ligands or pathogens from a wide variety of pathogens may be detected, as opposed to methods such as PCR-based methods that may only detect one or a subset of pathogens. The methods can be used, e.g., to detect endotoxin in donated blood before transfusion, in liquids to be used for cell culture, or in drinking water. In some embodiments, the assay is a simple yes/no assay, and the results indicate that PAMP ligand or pathogen is present in an unacceptable level. In some embodiments, the assay indicates what level of PAMP ligand or pathogen is present. In one example, LPS levels, which are used as a measure of bacterial biomass in the marine environment, can be assayed using an API that binds to LPS.

Kits

Kits based on the API compounds described herein can be developed and used, e.g., to screen biological fluids from infected (septic) patients, body fluids, or water or food, to name few applications. The APIs described herein can be used to detect a broad range of microorganisms including mycobacteria and fungi and so can be provided as reagents in a kit for detecting the presence of such microorganisms.

A kit containing an API can include one or more types of APIs and a standard. The API can be packaged in a suitable container. The kit can also include instructions for using the kit to detect the presence of a pathogen, e.g., a microorganism or a class or microorganisms.

Additional Uses

In addition to uses described above, a molecule that is a fusion of a pathogen recognition module, e.g., a TLR extracellular domain and an Fc portion of an immunoglobulin (i.e., an API) permits production of large amounts of recombinant proteins containing the pathogen recognition module (e.g., the ECD of a TLR) along with providing a relatively easy means for protein purification and handling via the Fc portion of the recombinant protein. In addition, APIs can have improved serum stability (i.e., improved half-life in serum) relative to a non-chimeric pathogen recognition protein or recognition module (e.g., TLR extracellular domain). Therefore, APIs are useful for treatment regimes and for assays in biological samples in which a non-chimeric protein might degrade more quickly. Furthermore, the use of an Fc region in the API allows for dimerization of the immunoadhesin by means of covalent disulfide bridging of Fc region of the immunoadhesin, thus improving their affinity for the cognate ligands. The immunoadhesin structure also allows for Fc receptor-mediated binding of the chimeric constructs. The Fc portion of the API (e.g., from an IgG or IgM) may be able to act by fixing complement, thus killing the bound bacterium. If the fixation of complement fails when an API is used, then the API may induce opsonophagocytosis of API-coated bacteria by professional phagocytes.

Papain digestion of the hinge region releases the pathogen recognition module from the Fc portion of an API. The Fc region can be removed from these preparations using methods known in the art (e.g., using a protein A substrate to remove the Fc fragment). Therefore, APIs are useful reagents for crystallization studies. Crystallization permits elucidation of three-dimensional structure, a useful parameter for drug design. Thus, APIs are commercially valuable for drug discovery protocols involving drug design as well as the use of the APIs themselves in therapeutic protocols.

Another major commercial interest is the search for an effective antifungal therapy. At present, the most widely (and almost uniquely) used antifungal agent for systemic fungal infections in the intensive care units is Amphotericin B (AmpB). However, the use of AmpB is limited by its extensive undesired side effects, which can include death. Developing alternative antifungal agents is a major task in medicine. An API that interacts with a fungus is therefore useful for diagnosis and treatment of fungal disease. An example of such a an API is the tollbody TLR2:Fc.

The invention is further illustrated by the following examples. The examples are provided for illustrative purposes only. They are not to be construed as limiting the scope or content of the invention in any way.

EXAMPLES

Example 1

Generation of a Multipurpose Fc Cloning Cassette

This Example describes the cloning of a "standard" Fc cloning cassette.

Briefly, the mouse IgG2a Fc was inserted into the pcDNA3 vector polylinker using known molecular biological methods (e.g., see Sambrook et al., Molecular Cloning, 2nd Edition, Cold Spring Harbor Laboratory Press, 1989) to generate the following "acceptor" cloning site:

```
GGAATTCTGCAGATATCCATCACACTG|GCGGCCGCGGGGGGC|GAGCCCAGAGGGCCCACAAT
       pcDNA3 Polylinker     NotI/Linker      Mouse IgG2a Fc
```

(SEQ ID NO: 3) The NotI site (bold font) was used to allow the creation of a "linker," which provides spacing between the recognition module and the hinge of the immunoglobulin, where the intermolecular disulfide bridges occur.

The presence of a flexible linker (see FIG. 1) providing spacing between the two portions of the fusion protein is important, since the recognition of clustered antigens greatly depends of the "flexibility" of their hinge regions. In this case, the linker included the addition of two flanking glycine residues (in addition to the three that the Not I site encodes).

The entire Fc fragment was used for several reasons. First, it was desirable to maintain all of the effector functions related to the Fc (e.g., complement fixation, enhanced half life in the blood, and binding to the Fc receptors). Second, using the entire Fc region permits the generation of dimeric proteins, which have the advantage of binding the cognate ligands with higher affinity. Third, including the entire Fc region permits easy purification and handling of the protein while enhancing its solubility, while the Fc region and can be cleaved by papain treatment to generate pure dimeric TLRs extracellular domains for, e.g., competition studies and crystallization. APIs purified from the conditioned protein free supernatant are essentially devoid of detectable contaminants.

Example 2

Generation of TLR4:Fc Tollbodies

This Example describes the generation of a human TLR4: murine IgG$_{2a}$ Fc tollbody.

The cloning strategy for making this construct involved cloning the Fc portion of the murine IgG2a was cloned into the pcDNA3 vector (Invitrogen) as described in Example 1. At the DNA sequence level, the fusion of TLR4 and mouse Fc is as follows:

```
TCAGATGAATAAGACC----------------GAGCCCAGAGGGCCCACAAT (SEQ ID NOs: 4, 5)
TCAGATGAATAAGACC|GGGGCCGCGGGGGGC|GAGCCCAGAGGGCCCACAAT (SEQ ID NOs: 6(lkr), 7)
     TLR4            Linker            Fc
```

Other chimeric proteins were developed using the same strategy (note that in the case of T4:Fc the Not site was destroyed after ligation because of the use of a PspOM/NotI cloning strategy). The predicted translation of the hinge region is as follows:

```
T2: Fc    ECHRAAAGGEPRG    (SEQ ID NO: 8)
T4: Fc    MNKTGAAGGEPRG    (SEQ ID NO: 9)
T9: Fc    WDCFAAAGGEPRG    (SEQ ID NO: 10)
CD14: Fc  ACARAAAGGEPRG    (SEQ ID NO: 11)
```

Figure 2:
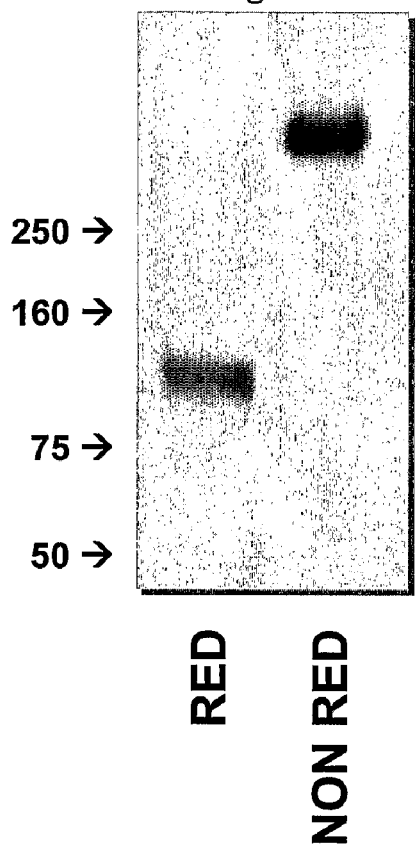
FIG. 2 is a Western immunoblot of TLR4:Fc API (anti mouse-HRP secondary reagent). Note that under non-reducing conditions (NON-RED) the apparent molecular weight is double.
Figure 9:
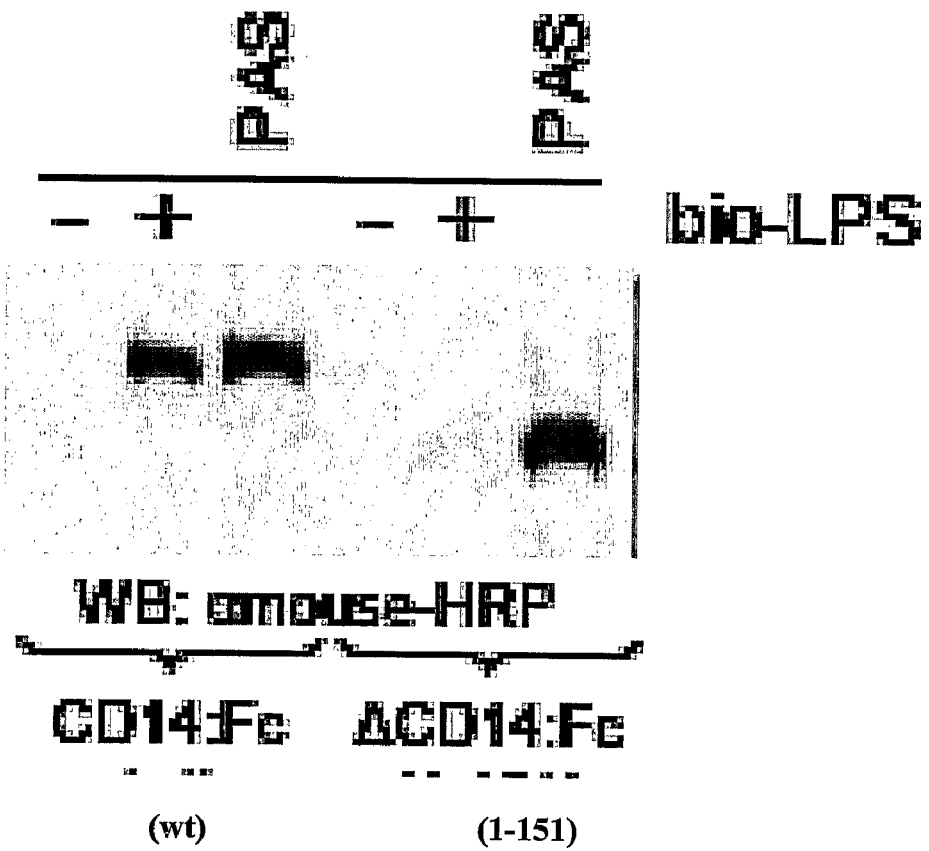
FIG. 9 is a Western Blot showing that CD14:Fc binds to LPS. CD14:Fc was captured from supernatants using avidin coated beads and biotin-LPS, and Western blotted with anti-mouse-HRP conjugated antibody followed by ECL detection. As a protein loading control, a protein A (PAS) precipitation is shown. Note that the 1-151 chimeric CD14:Fc was less efficient in binding to LPS.
Figures 10A, 10B, 10C, 10D:
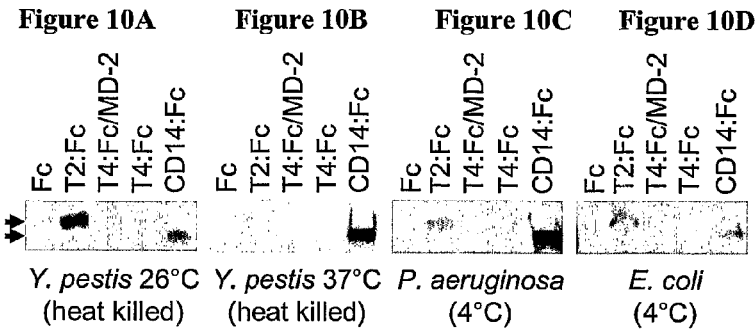
FIGS. 10A-10D are Western Blots showing that heat killed (*Y. pestis*, 26° C., 10A; *Y. pestis*, 37° C., 10B) and living (*P. aeruginosa*, 10C; *E. coli*, 10D) bacteria bind to Tollbodies. Bacteria were incubated in saline with a panel of APIs, as indicated. The cell pellets were electrophoresed and Western blotted with a HRP-conjugated anti mouse polyclonal antiserum. The two arrows indicate the apparent molecular weight of the tollbodies that were "copurified" with the bacteria. Note that different bacteria display a different binding profile.
Figures 11A, 11B, 11C:
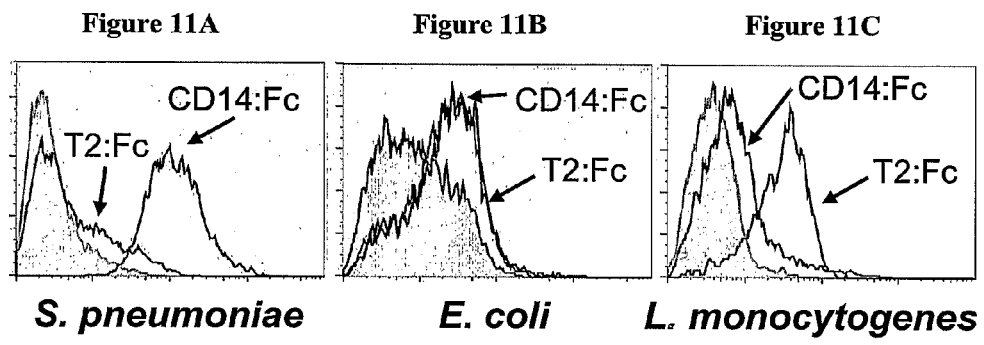
FIGS. 11A-G are flow cytometric profiles of bacteria coated with APIs.
Figures 11D, 11E, 11F, 11G:
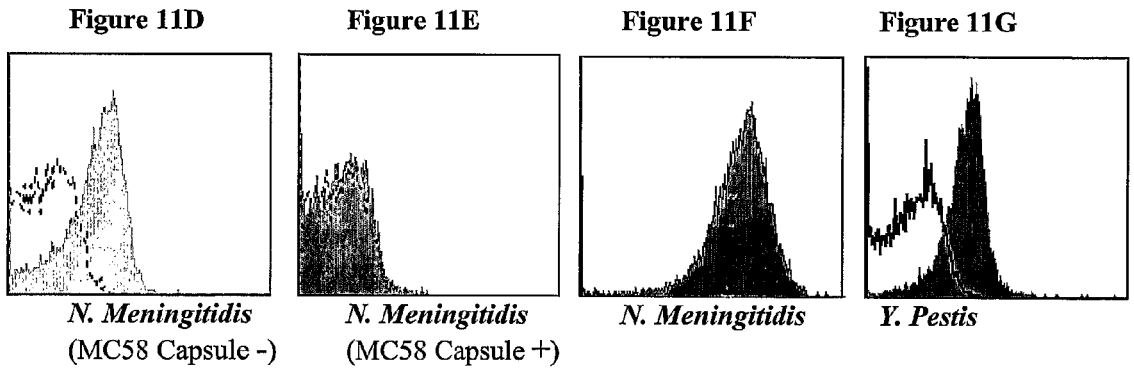

The molecule was secreted into the supernatant and displayed the expected molecular weight (see FIGS. 2 and 9). The TLR4 tollbody consists of the extracellular domain of TLR4 fused to the murine Fc portion of the IgG2a, and exists as a disulfide-linked homodimer, as demonstrated by electrophoresis on a gel run under reducing and non-reducing conditions, and blotted with a HRP conjugated anti mouse polyclonal antiserum; under nonreducing conditions, the construct ran at a molecular weight consistent with a dimmer, which dissociated under reducing conditions as expected.

TLR4 is the receptor for endotoxin (lipopolysaccharide, LPS) from Gram negative bacteria. LPS recognition by TLR4 is strictly dependent on a second molecule, MD-2. MD-2 associates with TLR4 on the extracellular side of the cell membrane and physically binds to LPS (Visintin et al., 2003, J. Biol. Chem. 278:48313-48320). Experiments were performed to determine whether TLR4:Fc had the same binding characteristics as native TLR4 (i.e., requires MD-2 to bind LPS). In these experiments, cells were allowed to grow and secrete T4:Fc in 5% fetal bovine, which provides the full complement of serum proteins required to optimally promote the interaction between endotoxin and TLR4 (i.e. LBP and CD14, Visintin et al., 278(48):48313-20 (2003)). Biotinylated-LPS was then added in the presence or absence of conditioned medium containing recombinant soluble FLAG tagged MD-2. Complexes of T4:Fc:MD-2:biotin-LPS were finally captured by using avidin linked to a solid support (agarose beads). The presence of T4:Fc and MD-2 in the captured complexes was assessed by anti-mouse and anti FLAG western analysis on the avidin pellets (see also example 6). The data demonstrated that TLR4:Fc does not bind to LPS in the absence of MD-2 (FIG. 3; protein loading was confirmed to be consistent by protein A precipitation, PAS). These experiments demonstrate that the TLR4:Fc retains the binding characteristics of native TLR4.

Example 3

Inhibition of Cellular Response to Lipopolysaccharide (LPS)

Since APIs can bind to purified bacterial products and intact bacteria, it is likely that they might exert a twofold action when injected in vivo. The first predicted action is to neutralize bacterial products shed during infection. These products, and in particular the lipopolysaccharides, are among the major causes of morbidity and mortality seen during septic conditions because of the induction of a systemic inflammatory state via soluble mediators and their pro-thrombotic effect. Neutralization of the aforementioned soluble effectors (namely TNFα and IL-1β) by using soluble decoy receptors or monoclonal antibodies, has proven to be a very effective strategy for alleviating the detrimental effects of both the systemic inflammatory state and some chronic inflammatory diseases (e.g. rheumatoid arthritis).

Analogously, neutralization of endotoxins (or any other pathogen-derived activator of a pathogen recognition protein) is expected to exert the same inhibitory effect, before the soluble proinflammatory mediators are even produced. APIs can function as soluble decoy receptors for microbial toxins, therefore attenuating paroxystic cellular responses. A second effect is bacterial killing by complement activation and opsonophagocytosis of the invading particles.

This Example describes experiments to determine whether the APIs described herein can be used to inhibit cellular responses to a pathogen. This was demonstrated using a TLR4:Fc tollbody. In these experiments, cells expressing TLR4 and MD-2, i.e., cells that can activate an NF-κB luciferase reporter upon LPS stimulation (responder cells), were co-cultured with increasing concentrations of cells secreting a TLR4:Fc or a TLR9:Fc. LPS, 10 ng/ml, was added to these cultures and the cultures were incubated for four hours. Luciferase activity was then assayed using standard reagents and procedures (see, e.g., Visintin et al., 278(48): 48313-20 (2003)).

Figure 4:
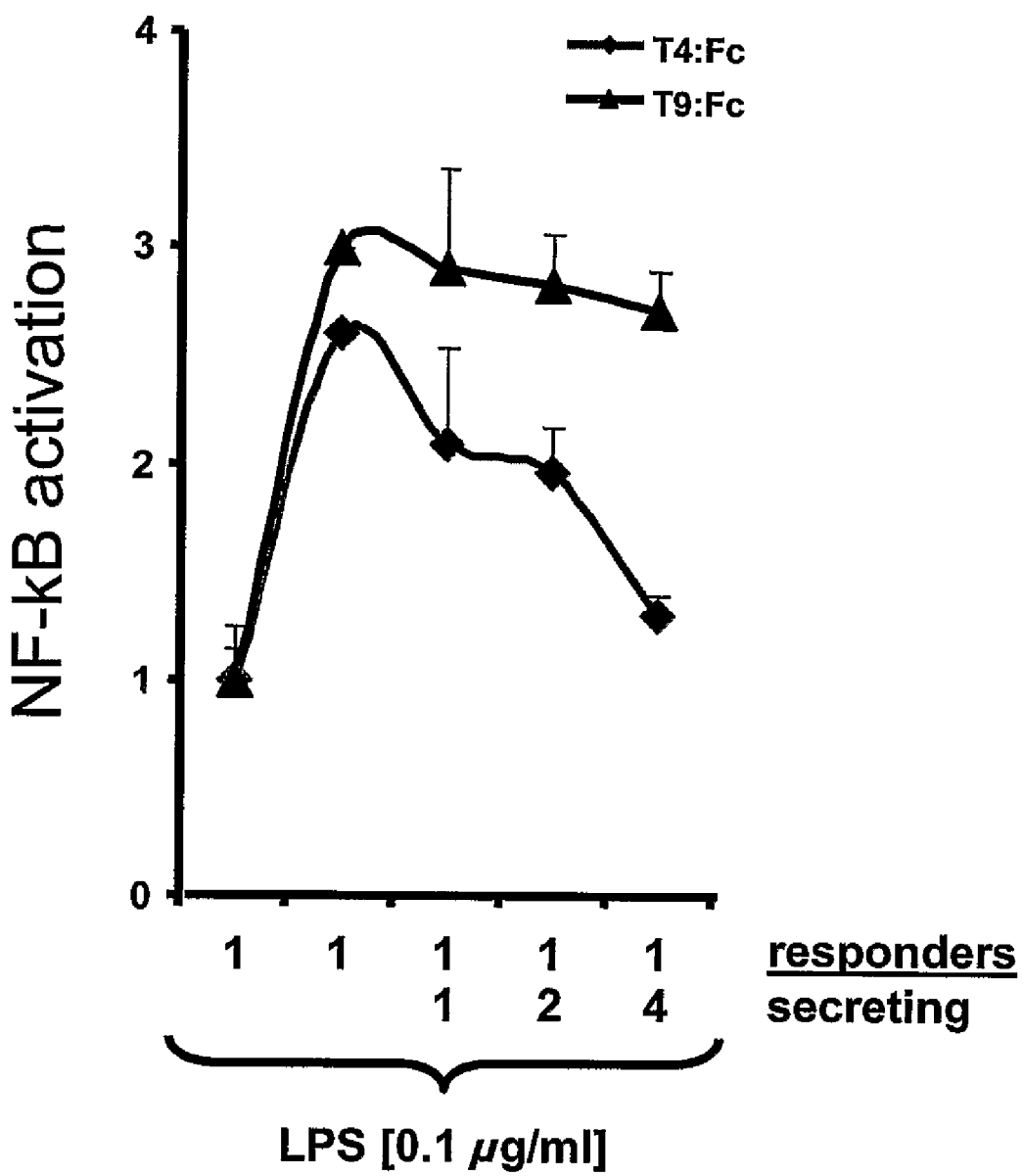
FIG. 4 is a line graph showing that the TLR4:Fc fusion protein inhibits LPS induced NF-κB activation in LPS responding cells. Responding cells (TLR4 and MD-2 expressing cells along with an NF-κB Luciferase reporter vector) were co-cultured with increasing amounts of TLR4: Fc secreting cells (gray line). At the highest concentration, there is a clear inhibition of LPS induced NF-κB response. The effect is specific, because a TLR9:Fc expressing cell line did not alter the LPS response (black line).

LPS stimulation of NF-κB expression, as measured by luciferase activity, was significantly reduced in the presence of TLR4:Fc in samples containing a ratio of 4:1 secreting cells:responder cells, as compared to cultures containing relatively fewer secreting cells (FIG. 4, gray squares). Responder cells that were incubated in the presence of TLR9:Fc did not show this decreased response (FIG. 4, black triangles). Therefore, in vitro, TLR4:Fc can attenuate the NF-κB activation induced by LPS in a system where responding cells (TLR4/md-2 stably transfected cells) were co-incubated with secreting cells. As shown in FIG. 13, treatment with TLR4:Fc inhibited the responses to LPS. Since TLR4 cannot bind to LPS without MD-2, it is likely that TLR4:Fc inhibits LPS responses by depleting the supernatant from MD-2 or sequestrating TLR4 bound MD-2. On the contrary, TLR9:Fc did not exert any effect on LPS responses.

These data demonstrate that the TLR4 tollbody (TLR4:Fc) can be used to specifically inhibit LPS responses and is therefore useful for preventing or ameliorating the effects of LPS in a cell, e.g., in an animal infected with a pathogen that produces LPS.

Without committing to any particular theory, it may be that the observed decrease in LPS stimulation of NF-κB expression in these experiments is due to competition by the soluble TLR4 ECD component of the TLR4:Fc tollbody with cell surface TLR4 for binding to MD-2. The TLR4:Fc/MD-2 complex binds LPS. The resulting TLR4:Fc/MD-2/LPS complex is unable to stimulate the TLR4 signaling pathway, thus inhibiting the induction of LPS-associated effects in the cell. These results indicate that the APIs described herein can be used to inhibit cellular responses to a pathogen.

Example 4

Generation of TLR9:Fc Tollbodies

This Example describes the generation of fusion proteins that include the extracellular domain of human toll-like receptor 9 (TLR9) and the fragment crystallizable (Fc) portion of a mouse immunoglobulin (Ig, isotype $G_{2a}$), which were generated essentially as described above in Example 1. The resulting chimeric (human-mouse) fusion protein is referred to as TLR9:Fc.

To identify the ECD of each toll like receptor, including TLR9, hydrophobicity profiling was performed on the primary sequence of the TLR using the ProfileScan program available at hits.isb-sib.ch/cgi-bin/PFSCAN. The regions corresponding to the putative transmembrane domain (TM) were identified as Ala813 to Trp856. Amino acids Met1 to Glu812 thus were assumed to define the putative extracellular domain of TLR9 (ECD9). To amplify ECD9 from the TLR9 sequence using PCR, a 25 nucleotide primer was used that introduced a BamH I restriction site before the ATG start codon of TLR9 (5'CGAGCTCGGATCCATGGGTTT CTGC3'; SEQ ID NO:12) and a 34 nucleotide primer (5'-CCAGCAGCGCGGCCGCGAA ACAGTCCCAGGAGAG-3'; SEQ ID NO:13)) was used that introduced a Not I restriction site that could be used to create an in-frame fusion with an Fc domain. After amplification of the ECD9 sequence, the resulting PCR fragment was digested with BamH I and Not I, which cleave the PCR fragment at their respective sites (shown in bold in the primer sequences, above). The digested fragment was subcloned into an Fc acceptor cassette as described infra.

A mouse $IgG_{2a}$ Fc sequence was prepared by PCR using a 44 nucleotide primer that introduced a Not I site and 7 additional bases to the 5' end of mouse $IgG_{2a}$ Fc (5'TCACCTGT-GCGGCCGCGGGGGGCGAGCCCAGAGGGC-CCACAATC-3'; SEQ ID NO:14)) and a 37 nucleotide primer that introduced a Sal I and a XhoI site after the TGA stop codon of the $IgG_{2a}$ sequence (5'-GGATATCTGCA-GAACTCGAGGTCGACTCAT TTACCCG-3'; SEQ ID NO:15)). The resulting PCR fragment was digested with the restriction enzymes Not I and Xho I, which cleave the PCR fragment at the sites shown in bold in the primer sequences supra. The 0.6 kDa fragment resulting from the cleavage was subcloned into the mammalian expression vector pcDNA3. This construct is termed the "acceptor cassette," which allowed the N-terminal in frame fusion of the ECD9 at the NotI site as described above. The NotI site (GC|GGCCGC; SEQ ID NO:16) and the seven additional bases introduced by the 5' PCR primer encode three alanine and two glycine residues. As a result, the ECD9 and Fc are separated by the pentapeptide linker Ala-Ala-Ala-Gly-Gly (SEQ ID NO:17).

Since TLR9:Fc possess an intact hinge region, the protein exists as a covalently bound homodimer of about 300 kDa. Mild reduction of the homodimer in 5 mM DTT (dithiothreitol) generates a single chain polypeptide of the expected molecular weight of about 150 kDa. The resulting TLR9:Fc is properly folded since it retains the ability to bind both DNA and protein A (which binds to the folded Fc).

Purification of TLR9:Fc

A human embryonic kidney (HEK293) cell line was generated that constitutively expressed TLR9:Fc. The cell line is referred to as 293rTLR9:Fc. 293rTLR9:Fc cells are maintained using in spinner flasks using routine culture methods under protein-free conditions in GIBCO's CD293 chemically defined protein free medium or the cells are grown in tissue culture flasks as adherent cells in the presence of 5% fetal calf serum. TLR9:Fc is synthesized by these cells but is not secreted in the culture medium and accumulates in the endoplasmic reticulum of 293rTLR9:Fc cells. Therefore, TLR9:Fc was purified from cell lysates for use in further experiments.

Briefly, the TLR9:Fc was purified by pelleting 293rTLR9:Fc cells and solubilizing them at a concentration of about $5\times10^8$ cells/ml in lysis buffer containing 0.5% TritonX-100, 20 mM Tris, 137 mM NaCl, 1 mM PMSF, 10 µg/ml aprotinin, and 10 µg/ml leupeptin. Cellular lysates were cleared by centrifugation and the post-nuclear supernatant was then passed through a Protein A affinity column (Amersham Pharmacia). Protein A binds to a single target sequence present in folded Fc, therefore the TLR9:Fc Tollbody is selectively retained by the column beads. The column is then washed with 10 column volumes of lysis buffer to eliminate contaminating proteins, and TLR9:Fc is eluted in 2 ml of 0.1 M glycine pH 2.2. The eluted fraction was immediately neutralized by the addition of 1/10 of the volume of 1 M Tris pH 8. This affinity purification step routinely yields a 95% pure protein preparation. As a secondary purification and polishing step TLR9:Fc was passed through an SX200 size fractionation column in Hanks balanced saline to eliminate small molecular weight contaminants and to exchange the buffer system.

The concentration of the tollbody in the first five 0.5 ml elution fractions is then assessed by either silver stain or Coomassie (Bradford) against a protein standard of known concentration (see also example 5 below).

Figure 7:
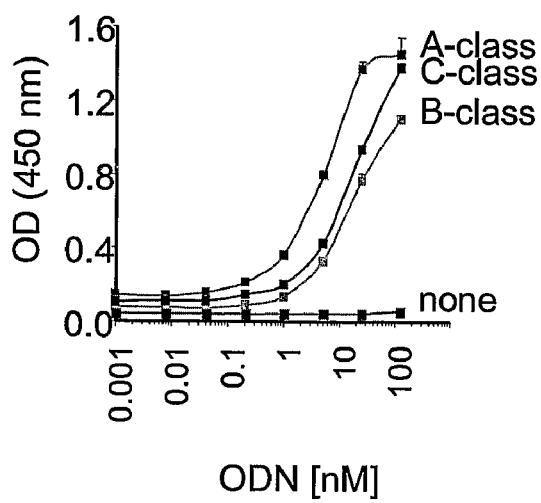
FIGS. 7 and 8 are line graphs illustrating the results of ELISA analysis of TLR9:Fc interaction with DNA. Oligonucleotides A, B, and C, representing three classes of DNA known to differently stimulate TLR9, were tested for binding to purified TLR9:Fc (FIG. 7) and for the ability to activate NF-κB in HEK 293 cells stably transfected with full-length TLR9 (FIG. 8).

To provide additional evidence that Tollbodies retain their ligand specificities, a series of binding assays were performed using purified TLR9:Fc, using the approach described herein for TLR2:Fc with slight modifications (e.g., by capturing the TLR9:Fc on protein A-coated plastic, followed by ligand addition in liquid phase. Avidin-HRP was used as the detection reagent). As noted above, TLR9:Fc including the full length of the extracellular domain is not secreted in the supernatant, therefore it was purified from cellular lysates. As shown in FIG. 7, TLR9:Fc is capable of binding to the three different classes of immunostimulatory CpG oligonucleotides known to elicit different type of responses in TLR9 expressing cells (Rothenfusser et al., Curr Opin Mol Ther, 2003. 5(2): p. 98-106). Despite almost identical binding, the three types of CpG rich DNA differentially activate NF-κB in TLR9-expressing cells (FIG. 8), revealing a discrepancy in binding/function relationship in these cells. This suggests that cell-specific responses to the same ligand depend on additional (unknown) triggering factors. The present inventors recently reported an extensive study on TLR9 and presented a detailed characterization of the binding and subcellular localization of TLR9 (Latz et al., Nat. Immunol. 5(2): 190-8 (2004)).

Example 5

TLR2:Fc Tollbodies

In the experiments described in this Example, a tollbody containing the ECD of TLR2 was prepared and tested, and it was demonstrated that TLR2:Fc can bind to TLR2 ligands using ELISA.

Figure 5:
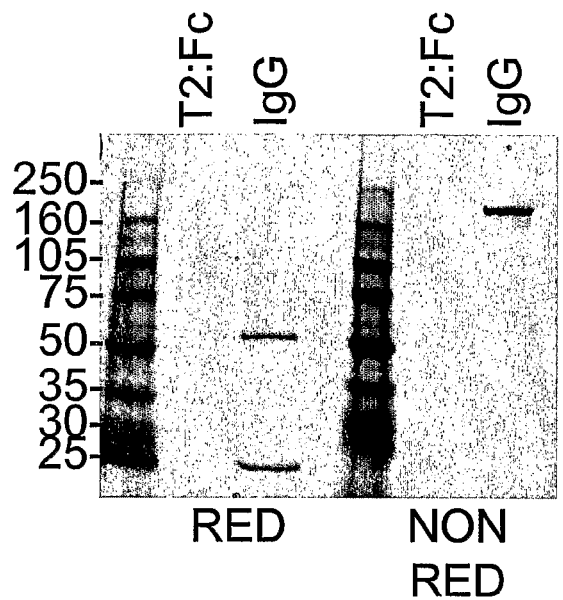
FIG. 5 is a representation of a gel showing the migration pattern of purified TLR2:Fc, affinity purified using a protein A column. After elution and desalting, the molecule was run under reducing (RED) and non reducing (NON RED) conditions in a 4-15% SDS-PAGE and stained with Coomassie™. As a comparison, an IgG$_1$, was run in parallel (anti FLAG, M2, Sigma). Molecular weight markers (MW) are also shown.

An example of the results of purification of TLR2:Fc is shown in FIG. 5. In this protocol, the purified protein was electrophoretically separated in 4-15% SDS-PAGE under reducing and non reducing conditions and the gel stained in Coomassie™ blue (Bio-Rad). An $IgG_{2a}$ (anti FLAG, clone M2, Sigma) is shown as a comparison. The non-reduced form of TLR2:Fc is predicted to be a covalently bound dimer linked via the hinge region of the Fc portion of the mouse IgG, which contains three cysteine residues.

As shown in FIG. 5, the dimeric form of TLR2:Fc shows an apparent molecular weight slightly higher than the one deduced from the reduced counterpart (about 200 kDa). The reason for this difference between the observed and predicted molecular weight may reflect a slightly aberrant migration due to the high degree of glycosylation and the non-globular nature of the highly disulfide bridged LRR (leucine-rich repeat)-rich extracellular domain of TLRs. To assess whether the TLR portion of the molecule is properly folded, ligand binding assays were performed using several different approaches.

Figure 6:
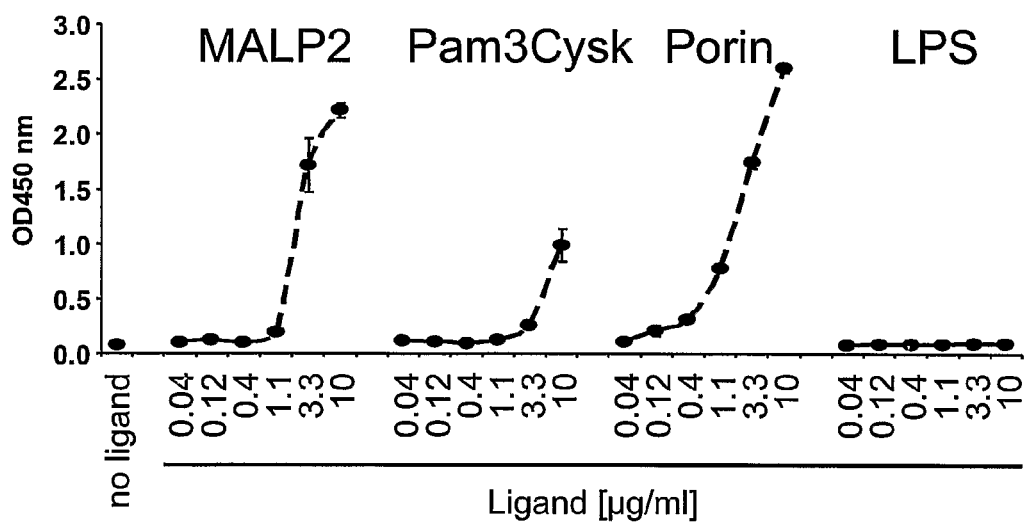
FIG. 6 is a set of four line graphs showing that TLR2:Fc binds to its cognate ligands, MALP2, Pam3Cysk, and porin, but does not significantly bind to LPS. ELISA plates were coated with titrated amounts of the indicated bacterial components and TLR2:Fc was added in constant amounts. After washing, bound TLR2:Fc was detected using an HRP-conjugated anti-mouse antiserum.

FIG. 6 illustrates representative binding data for TLR2:Fc. Titrated amounts of known TLR2 ligands were adsorbed on plastic (MALP2, Pam3CysK, *Neisseria* porin (porB), and repurified LPS as a negative control) in carbonate buffer, pH 9. After blocking (with Pierce SuperBlock®) a constant amount (0.1 µg/well) of TLR2:Fc was added and incubated for one hour at room temperature. Following extensive washing with PBS-Tween, the bound tollbody was detected using an HRP conjugated anti-mouse antibody followed by chromogenic substrate addition, incubation, and assay by reading the $OD_{450}$. As predicted, TLR2:Fc bound to the cognate purified ligands, but not to LPS, suggesting that the molecule is properly folded.

The recognition of purified bacterial products is not dependent on TLR2 interaction with other TLRs, as it was implied by studying TLR2-dependent signaling in mice (Takeuchi et al., 2001, Int. Immunol. 13:933-940; Takeuchi et al., 2002, J. Immunol. 169:10-14). As it is the case for TLR9, these data suggest that recognition and signaling are two separate events, the latter requiring ligand-dedicated accessory proteins providing the correct intracellular transducing units in place. Thus, at least two types of compounds that interfere with TLR2 activity can be identified; those that interfere with TLR2 interaction with other TLRs and those that interfere with the aspect of signaling that requires ligand-dedicated accessory proteins.

Example 6

TLR4:Fc and CD14:Fc Bind LPS

This Example describes the use of a biotin-LPS ligand precipitation assay (Visintin, A., et al., J Biol Chem, 2003. 278(48): p. 48313-20) to test whether TLR4:Fc and CD14:Fc interact with LPS.

Figure 3:
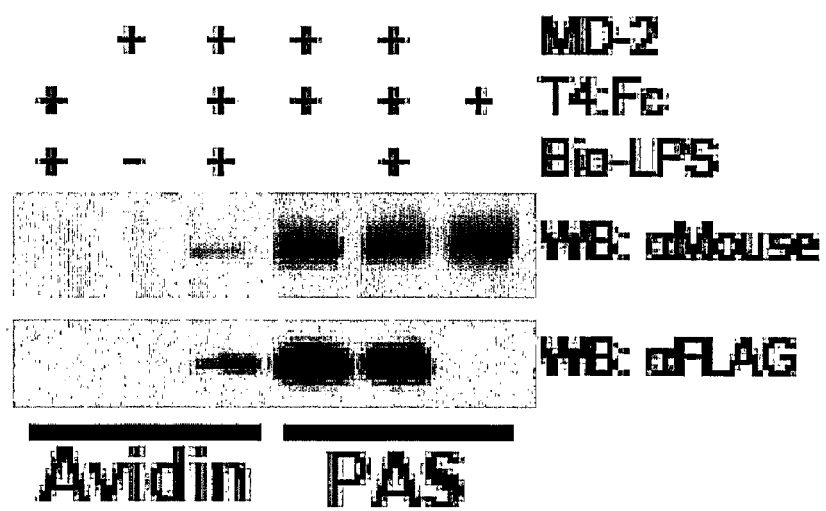
FIG. 3 is a Western immunoblot showing that TLR4:Fc API binds to LPS when MD-2 is present. Biotinylated LPS was used to capture LPS interacting proteins in the supernatant of transiently transfected cells. Avidin immobilized onto a solid support (Sepharose CL6B) was used to purify the LPS/TLR4: Fc complexes and an anti-mouse Western blotting was then performed to detect the LPS bound TLR4:Fc in the precipitate (aM-HRP). The lower part of the gel was probed for the FLAG epitope to assess the presence of MD-2 in the precipitate. Protein A Sepharose precipitates (PAS) are included to show the total amounts of API protein. TLR4:Fc was captured by the biotinylated LPS only when MD-2 was added to the mix.

Briefly, supernatants containing either TLR4:Fc or CD14:Fc were incubated in the presence of biotinylated LPS and avidin coated beads. The beads were then collected by centrifugation, washed three times and subjected to electrophoresis and western blot analysis with an HRP conjugated anti mouse antiserum, in order to assess the presence of captured TLR4:Fc and CD14:Fc. As shown in FIG. 3, TLR4:Fc binds to LPS only when in the presence of MD-2, thus confirming that TLR4 participates in the recognition of LPS in an etherocomplex formed by the extracellular domain of TLR4 and MD-2, as previously reported. In addition, the CD14:Fc, and a truncated variant comprising only the first 151 amino acids of CD14 (ΔCD14), both bind to LPS (FIG. 9). To provide additional evidence that APIs retain their ligand specificities, a series of binding assays were performed using purified TLR9:Fc using the approach presented for TLR2:Fc with slight modifications (i.e., by capturing the tollbody with plastic coated protein A followed by ligand addition in liquid phase-avidin-HRP was used as detection reagent). As previously noted, TLR9:Fc is not secreted in the supernatant, therefore it was purified from cellular lysates.

Figure 8:
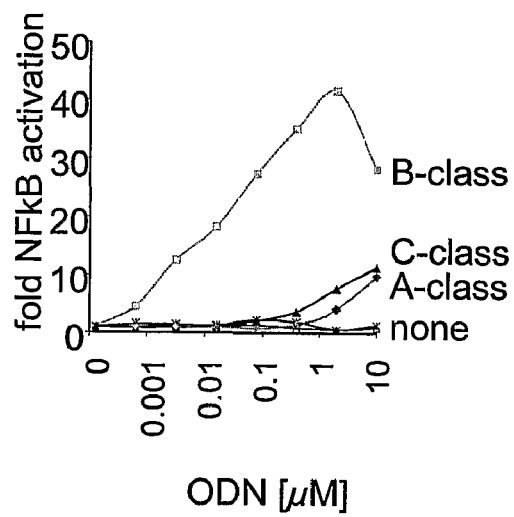

As shown in FIGS. 7 and 8, TLR9:Fc is capable of binding to the three different classes of immunostimulatory CpG oligonucleotides known to elicit different type of responses in TLR9 expressing cells (Rothenfusser et al., Curr Opin Mol Ther, 2003. 5(2): p. 98-106). Despite almost identical binding, the three types of CpG rich DNA can differently activate NF-κB in TLR9 expressing cells, revealing a discrepancy in binding/function relationship in these cells. These results suggests that cell-specific responses to the same ligand depend on additional (unknown) triggering factors.

Example 7

Anti-Pathogen Immunoadhesins can Bind to Bacteria

Since APIs can bind to purified bacterial products, they were tested for their ability to bind to whole bacteria, which is a desirable feature for diagnostic and treatment uses. To test this, a bacterial precipitation/western blot ("bacteria-IP") was developed. Briefly, whole heat-killed bacteria or intact bacteria were ice cooled during the log-growth phase, were washed in PBS and incubated with APIs. The amounts of bacteria are kept to a minimum (about $1 \times 10^8$ to minimize chromosomal DNA contamination during the lysis step). The APIs are added to the washed bacterial pellet as purified proteins (1 μg in 1 ml of HBSS final) or conditioned supernatants (10 ml). Note that when the APIs are added as conditioned supernatants, no serum components are present, since the cells are grown in protein free medium. After a period varying from one hour to an overnight incubation, the bacteria are collected by centrifugation, washed twice in PBS and the bacterial pellets are quickly lysed in boiling SDS sample buffer. The presence of bound APIs in the bacterial lysate is assessed by SDS-PAGE and a western blot analysis with an HRP-conjugated anti mouse antiserum.

In FIGS. 10A-D, a "bacteria-IP" is presented. Despite identical input, the pattern of binding of different APIs differs according to the bacteria used to perform the precipitation. For example, heat killed *Y. pestis* grown at 26° C. (FIG. 10A) binds substantially better to TLR2:Fc than the same bacterium grown at 37° C. (FIG. 10B) (which binds better to CD14:Fc). This might reflect the fact that the composition of the bacterial surface differs according to the different growing conditions. It is noteworthy to mention that the LPS of *Y. pestis* grown at 37° C. is substantially less immunostimulatory than the 26° C. counterpart. Also, *P. aeruginosa* (FIG. 10C) appears to bind better to CD14:Fc than to TLR2:Fc, whereas *E. coli* (0111:B4; FIG. 10D) binds equally well to both. In addition, the Factor H based immunoadhesin efficiently bound to capsulated live Meningococcus and the BPI:Fc bound to a non-virulent strain of *Yersinia pestis* (strain JG150/KIM5).

To obtain a quantitative readout of API binding to bacteria, a cytofluorimetric approach (FACS) was used. Briefly, bacteria were incubated with the APIs, washed and stained by incubation with FITC labeled anti mouse antiserum. In FIGS. 11A-G, typical FACS profiles are presented. Binding of APIs to bacteria can be therefore quantitatively monitored by FACS analysis and essentially reproduces the data acquired by bacterial-IP.

These data demonstrate that APIs can bind to intact bacteria in vitro and therefore should be able to fix complement and thereby trigger complement-mediated lysis of target pathogenic bacteria. Moreover, the fact that an API can bind to highly pathogenic bacteria, suggests that the API can be used to target potential deadly bioterroristic agents, such as *Y. pestis*, in vitro and in vivo. In addition, these methods can be used to detect the presence of bacteria in a sample, e.g., a sample of a liquid such as blood or blood products, cell culture media.

Example 8

APIs can Inhibit Cellular Responses to Bacterial Products

The observation that APIs can bind to purified bacterial products and intact bacteria suggests that they might exert a two-fold action when injected in vivo: neutralization of toxic bacterial products and pathogen killing. Bacterial products that are shed during the course of an infection, particularly lipopolysaccharides and lipoproteins, induce inflammation and coagulopathies, which are among the major causes of mortality during septicemia. Neutralization of pro-inflammatory soluble effectors such as TNFα and IL-1β by using soluble decoy receptors or monoclonal antibodies has proven to be a very effective strategy for alleviating the detrimental effects on cytokine driven diseases (Jit et al., Rheumatology (Oxford) 44:323 (2005); Goldbach-Mansky and Lipsky, Annu Rev Med 54:197 (2003)). Analogously, neutralization of bacterial endotoxins or other pathogen-derived TLR activators might exert the same inhibitory effect before the soluble proinflammatory mediators are even produced. TLR-based APIs might function as soluble decoy receptors for selected PAMPs.

As demonstrated herein, purified T4:Fc can greatly inhibit LPS responses in vitro. As shown in FIG. 12A, treatment with T4:Fc inhibited LPS-induced NF-κB activation in HEK293 cells expressing TLR4 and a NF-κB luciferase reporter gene. In the experiment illustrated in FIG. 7A, MD-2 was provided as conditioned medium from MD-2 secreting cells. Because TLR4 cannot bind to LPS without MD-2 (see Section C4a and (Visintin et al., J Biol Chem 278:4831 (2003)), one possible inhibition mechanism is that T4:Fc interacts with soluble MD-2, and limits LPS availability by functioning as a soluble decoy receptor (manuscript submitted for publication (Navia et al., Proc Natl Acad Sci USA 76:4071 (1979)) and (Kennedy et al., J Biol Chem 279:34698 (2004); Gioannini et al., Proc Natl Acad Sci USA 101:4186 (2004)). A similar inhibitory effect (as demonstrated by diminished IL-6 production) was observed in LPS stimulated human PBMC, FIG. 12B. The presented data show that APIs able to bind to at least one TLR ligand can exert an anti-inflammatory effect on immune cells, with beneficial outcomes in the treatment of inflammation.

Example 9

APIs Effectively Kill Pathogenic Organisms In Vitro

One of the most important effector functions linked to the immunoglobulins Fc region, is the activation of the lytic cascade of the complement system. As the APIs contain a pathogen recognition domain and the Fc, it was predicted they may be used to target bacteria and cause their death by MAC deposition. In order to prove the concept, an immunoadhesin was developed based on the bacteria recognition domain of human Factor H.

Factor H is a modular molecule composed of 20 complement control protein domains (CCP) and its physiological role is to inhibit complement activation in a complex enzymatic regulatory loop. CCP 6-20 are involved in binding to the surface of sialylated gonococci (Ram et al., J Exp Med 187:743 (1998)). A chimeric protein comprising the CCP 6-20 or CCP 18-20 of Factor H and the Fc portion of IgG2a was engineered (Factor H:Fc). A bactericidal assay was performed in the presence or the absence of the Factor H:Fc immunoadhesin to determine if this molecule bound to sialylated *Neisseria gonorrhoeae* and at the same time triggered the classical lytic complement pathway, thus killing the organism. Briefly, bacteria (~2,000 CFU) were suspended in Hanks and incubated with normal human serum (10% v/v) alone or NHS in the presence of the Factor H:Fc (CCP 18-20). Duplicate aliquots were plated out at 0 minutes and 30 minutes. Survival was expressed as the percentage of colonies surviving at the 0 point.

The results are shown in FIG. 14. The average of duplicates is shown. Unsialylated mutant gonococcus (strain F62) is susceptible to complement-mediated killing. The sialylated *Neisseria* strain (F62) was resistant to complement mediated lysis (third bar, ~90% survival after a 30 minute incubation in 10% human serum) by virtue of its ability of binding to Factor H, the complement inhibitor. However, the addition of the Factor H immunoadhesin reverted this phenotype, making the resistant strain susceptible to complement killing (fourth bar).

These results demonstrate that the APIs described herein can kill living bacteria, and suggest that the Fc portion of the APIs triggered the classic pathway of complement activation.

Example 10

API can Interfere with Cellular Activation by Hampering TLR Responses

Human peripheral blood mononuclear cells (PBMCs) and the macrophage-like cell lines THP-1 and RAW can be used to further explore the anti-inflammatory role of the APIs.

Cells are seeded in 96-well microtiter plates and stimulated in triplicate with serially diluted API ligands that are known to elicit a proinflammatory response (e.g., LPS, flagellin, PGN or porins) in the presence or the absence of titrated amounts of the relevant API. After an overnight incubation, secretion of IL-6, RANTES, TNFα and IL-8 are measured in the supernatants with commercial ELISA kits. Results can be plotted, e.g., in three-dimensional graphs depicting PAMP concentration on the X axis, API concentration on the Y axis and cytokine activation level on the Z axis. An API is considered anti-inflammatory if cytokine production is statistically significantly lower in the presence of the API than in the absence of the API.

Example 11

API Interference with Bacterial Proliferation

To evaluate the efficiency with which APIs interfere with bacterial proliferation, aliquots of each bacterial species are incubated at 37° C. with purified APIs over a wide range of concentrations (0.001-1 µg/sample). Aliquots are withdrawn after 30, 60 or 90 minutes and plated on agar plates; controls include aliquots plated immediately after addition of API (time 0 control). For each time and concentration points, bacterial viability is expressed as the number of CFUs divided by the number of CFUs of the untreated sample, multiplied by 100 (% viability). Should any of the APIs inhibit bacterial proliferation, these experiments produce dose-response curves from which one can calculate the minimal effective concentration (MEC) and the $EC_{50}$ of the API in vitro. In a second set of experiments, bacteria are incubated with combinations of APIs in order to determine whether they exert a synergistic effect. Ethanol treatment is used as a positive control (0% viability), and APIs that are not expected to bind to bacteria, such as T9:Fc, are used as negative controls (100% viability). These experiments reveal whether simple incubation of bacteria with these artificial antibody-like proteins results in bacteriostatic activity in vitro.

Example 12

API-triggered Complement-Mediated Killing

Example 9 demonstrated that the Factor H:Fc API can bind and kill a sialylated bacterium such as *Neisseria gonorrhoeae* in a complement-dependent manner. To further study the mechanism(s) of API killing—in particular, the contribution of the Fc portion of the API molecule—C-terminal (Fc) truncated forms of the chimeric API proteins are generated, and the ability of Fc-truncated and unaltered API reagents to kill a panel of clinically relevant pathogens such as *Staphylococcus aureus, Streptococcus pneumoniae, Pseudomonas aeruginosa, Salmonella enterocolitica* and *Yersinia pestis* is evaluated. Two strategies are used to measure API anti-bacterial activity: bacterial colony formation and flow cytometry.

(A) Bacterial viability is assessed by counting colony forming units (CFU) as described in Example 9. Briefly, bacteria are incubated with serial dilutions of individual APIs. Aliquots corresponding to 2000 CFU are withdrawn immediately (time 0) or after 30, 60, or 90 minutes and plated on appropriated agar plates. Colonies are counted and plotted as a function of API concentration at each time-point. A time-dependent and API concentration-dependent reduction of bacterial survival will indicate that the API is killing the bacteria. As in earlier experiments, positive controls consist of API treatment of ethanol-killed bacteria, and negative controls consist of test bacteria incubated with an API reagent such as T9:Fc, which binds intracellular compounds and is not cytotoxic against whole bacteria.

(B) Flow cytometry offers the advantage of allowing monitoring of API binding to the bacterial surface and characterization of the API-positive population. Living intact bacteria are impermeable to DNA intercalating drugs like propidium Iodide (PI). If API binds the bacteria and forms pores at the C6-C9 membrane attack complex, then PI will permeate the bacterial cell wall, bind the bacterial chromosome and be detectable by flow cytometry. Red fluorescence from intrabacterial PI are used as a measure of osmotic shock. A commercially available assay such as the Molecular Probes Live/Dead® BacLight™ Bacterial Viability and Counting Kit is used for flow cytometry.

Example 13

API-triggered Opsonophagocytosis

To evaluate the ability of an API to trigger opsonophagocytosis, two mechanisms of bacterial entry into cells in vitro are evaluated: 1) uptake by "non-professional" phagocytes such as the HEK293 human embryonic kidney cell line and 2) uptake by the macrophage-like cell lines THP-1 and RAW and by human macrophages. With "non-professional" phagocytes such as HEK293 cells, bacterial binding to cells that have been transfected with different fluorescence-tagged Fc receptors is followed visually. Stably transduced cell lines expressing CD36 tagged with yellow fluorescence protein (YFP) or CD16 tagged with cyan fluorescence protein (CFP) have been established. Both receptors are visualized in living cells by confocal microscopy. Confocal microscopy is used to monitor the formation of Fc receptor clusters around API-treated bacteria. The experiments are conducted under protein-free conditions to minimize interference from serum components. Bacteria should bind to the Fc receptors only when they are coated with the Fc-containing APIs. With API bridging via their Fc portion, a fluorescent "cup" should form at the interface bacteria/cell membrane. HEK293 cells, which do not normally internalize bacteria, also might become internalization competent.

In order to establish whether APIs can enhance phagocytosis in professional phagocytes, similar experiments are performed with macrophage-like cell lines THP-1 and RAW, and with human macrophages purified from the blood of healthy donors. Cellular internalization of bacteria that have been coated with API is measured, with uncoated bacteria serving as controls. Commercially available Fc receptor-blocking antibodies are used to determine the contribution of API opsonization. Under protein-free conditions, non-professional phagocytes should efficiently internalize bacteria only if they are coated with API, whereas professional phagocytes will internalize both coated and uncoated bacteria, but API coating will accelerate or enhance bacterial uptake. Bacterial internalization is measured quantitatively by flow cytometry of cells that have been with incubated with fluorescence-tagged bacteria, e.g., using DNA intercalating agents to tag permeabilized bacteria (Latz et al., J Endotoxin Res 9:375 (2003)).

Example 14

API Mediated Pathogen Neutralization In Vivo

To evaluate the ability of APIs to neutralize pathogens in vivo, an animal model of *Y. pestis* infection is used (Jarrett et al., Infection and Immunity 72:2052-56 (2004)). One or more doses of a BPI:Fc API is used, e.g., 5, 10, 20, 100, 200, 250, and/or 500 μg per mouse. The BPI:Fc is administered systemically, by subcutaneous administration. The animal model is then monitored for a change in symptoms of the disorder, and/or the level of pathogen present. Levels of pathogen present are determined by drawing 0.25 ml of blood from each mouse by retro-orbital bleeding, and determining the anti-F1 and anti-V titers in the sera by direct immunoglobulin G (IgG) enzyme-linked immunosorbent assay in which 96-well plates were coated with soluble F1 and V proteins, as previously described (Anderon et al., Infect. Immun. 64:4580-4585 (1996)). An API is considered to have neutralized the pathogen if the animal shows a significant improvement in one or more symptoms of the disorder, or a significant decrease in the level of pathogen present.

Example 15

Tollbodies as a Source of TLR Extracellular Domains (ECD)

Tollbodies can be used as source of TLR extracellular domains (ECD). Tollbodies are digested with Papain to release "pure" TLR ECD. The ECD is then deglycosylated using Endoglycosidase F and subjected to crystallization. Detailed structure information is obtained by standard X-ray diffraction methods. Crystallization of TLRs is a major task in the field, and there are seldom reports of successful high yield production of toll related proteins. The use of tollbodies provides material for these kind of studies.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a disorder associated with a pathogenic bacterium in a subject, the method comprising administering a therapeutically effective amount of an anti-pathogen immunoadhesin (API) to the subject, wherein the API comprises a polypeptide comprising
the amino acid sequence of SEQ ID NOs: 20, 21, 30, 31, 32, or 33, thereby treating the disorder associated with a pathogenic bacterium in the subject.

2. The method of claim 1, wherein the disorder is a pathogen-associated infection.

3. The method of claim 1, wherein the disorder is an inflammatory condition associated with infection with the bacterium.

4. The method of claim 1, wherein the bacterium is selected from the group consisting of *P. aeruginosa, S. pneumoniae, Y. pestis, E. coli, S. typhimurium, N. meningitidis, N. gonorrhoeae, H. influenzae*, and *S. aureus*.

5. A method of treating a disorder associated with a pathogenic bacterium in a subject, the method comprising administering a therapeutically effective amount of an API to the subject, wherein the API comprises a polypeptide comprising the amino acid sequence of SEQ ID NOs:18 or 19, thereby treating the disorder associated with a pathogenic bacterium in the subject.

6. The method of claim 5, wherein the disorder is a pathogen-associated infection.

7. The method of claim 5, wherein the disorder is an inflammatory condition associated with infection with the bacterium.

8. The method of claim 5, wherein the bacterium is selected from the group consisting of *P. aeruginosa, S. pneumoniae, Y. pestis, E. coli, S. typhimurium, N. meningitidis, N. gonorrhoeae, H. influenzae*, and *S. aureus*.

9. The method of claim 1, wherein the API comprises a polypeptide comprising the amino acid sequence of SEQ ID NO:20.

10. The method of claim 1, wherein the API comprises a polypeptide comprising the amino acid sequence of SEQ ID NO:21.

11. The method of claim 1, wherein the API comprises a polypeptide comprising the amino acid sequence of SEQ ID NO:30.

12. The method of claim 1, wherein the API comprises a polypeptide comprising the amino acid sequence of SEQ ID NO:31.

13. The method of claim 1, wherein the API comprises a polypeptide comprising the amino acid sequence of SEQ ID NO:32.

14. The method of claim 1, wherein the API comprises a polypeptide comprising the amino acid sequence of SEQ ID NO:33.

15. The method of claim 5, wherein the API comprises a polypeptide comprising the amino acid sequence of SEQ ID NO:18.

16. The method of claim 5, wherein the API comprises a polypeptide comprising the amino acid sequence of SEQ ID NO:19.

* * * * *

UNITED STATES PATENT AND TRADEMARK OFFICE
CERTIFICATE OF CORRECTION

| | | |
|---|---|---|
| PATENT NO. | : 8,080,245 B2 | Page 1 of 1 |
| APPLICATION NO. | : 11/659154 | |
| DATED | : December 20, 2011 | |
| INVENTOR(S) | : Alberto Visintin and Douglas T. Golenbock | |

It is certified that error appears in the above-identified patent and that said Letters Patent is hereby corrected as shown below:

Title Page, column 2 Item (56) References Cited, under (Other Publications), line 30:

Delete "Septice" and replace with -- Septic --.

In the Specifications:

Column 1, line 12:

Add:

STATEMENT AS TO FEDERALLY SPONSORED RESEARCH

This invention was made with government support under grant no. GM054060 awarded by the National Institutes of Health. The government has certain rights in the invention.

Signed and Sealed this
Twenty-seventh Day of March, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,080,245 B2 | Page 1 of 1 |
| APPLICATION NO. | : 11/659154 | |
| DATED | : December 20, 2011 | |
| INVENTOR(S) | : Visintin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 120 days.

Signed and Sealed this

Second Day of October, 2012

David J. Kappos
*Director of the United States Patent and Trademark Office*